(12) United States Patent
Frank et al.

(10) Patent No.: US 8,207,182 B2
(45) Date of Patent: Jun. 26, 2012

(54) SUBSTITUTED CYCLIC UREA DERIVATIVES AND THE USE THEREOF AS VANILLOID RECEPTOR 1 MODULATORS

(75) Inventors: Robert Frank, Aachen (DE); Bernd Sundermann, Aachen (DE); Hans Schick, Berlin (DE); Helmut Sonnenschein, Berlin (DE)

(73) Assignee: Gruenenthal GmbH, Aachen (DE)

( * ) Notice: Subject to any disclaimer, the term of this patent is extended or adjusted under 35 U.S.C. 154(b) by 349 days.

(21) Appl. No.: 11/875,570

(22) Filed: Oct. 19, 2007

(65) Prior Publication Data

US 2008/0090855 A1    Apr. 17, 2008

Related U.S. Application Data

(63) Continuation of application No. PCT/EP2006/003519, filed on Apr. 18, 2006.

(30) Foreign Application Priority Data

Apr. 19, 2005  (DE) .................. 10 2005 018 191

(51) Int. Cl.
| | |
|---|---|
| A61K 31/513 | (2006.01) |
| A61K 31/4164 | (2006.01) |
| A61K 31/4166 | (2006.01) |
| A61P 1/00 | (2006.01) |
| A61P 25/00 | (2006.01) |
| A61P 25/02 | (2006.01) |
| A61P 25/08 | (2006.01) |
| A61P 25/16 | (2006.01) |
| A61P 25/28 | (2006.01) |
| A61P 25/30 | (2006.01) |
| A61P 27/02 | (2006.01) |
| A61P 15/00 | (2006.01) |

(52) U.S. Cl. ........ 514/274; 514/386; 514/387; 544/316; 548/306.4; 548/307.1; 548/323.5

(58) Field of Classification Search .................. None
See application file for complete search history.

(56) References Cited

U.S. PATENT DOCUMENTS
| | | | |
|---|---|---|---|
| 4,216,284 A | 8/1980 | Sakai et al. | |
| 5,661,169 A | 8/1997 | Di Malta et al. | |

FOREIGN PATENT DOCUMENTS
| | | |
|---|---|---|
| DE | 43 00 912 A1 | 7/1994 |
| EP | 0 313 397 A1 | 4/1989 |
| EP | 0 694 536 A1 | 1/1996 |
| EP | 1 864 971 A1 | 12/2007 |
| GB | 1 130 904 | 10/1968 |
| JP | 58-203976 A | 11/1983 |
| JP | 63-170011 A | 7/1988 |
| WO | WO 96/38421 A1 | 12/1996 |
| WO | WO 97/08150 | 3/1997 |
| WO | WO 02/16318 A1 | 2/2002 |
| WO | WO 2004/103281 A2 | 12/2004 |

OTHER PUBLICATIONS

Newman et al., DDT vol. 8, Oct. 2003, p. 898-90.*
Chawla et al., CRIPS vol. 5, No. 1, Jan.-Mar. 2004, p. 9-12.*
Gunthorpe et al., The Journal of Pharmacology and Experimental Therapeutics, 321, 2007, 1183-1192.*
Alzheimer's Disease Treatment Phases, http://www.alzheimerstreatment.org/treatment/disease-treatment.htm.*
Alzheimer's Drugs, Consumer Reports Best Buy Drugs (p. 1-5).*
Fukushima et al, caplus an 2007:1110441, 2007.*
Walpole, Christopher S.J., et al., Analogues of Capsaicin with Agonist Activity as Novel Analgesic Agents; Structure-Activity Studies. 2. The Amide Bond "B-Region", J. Med. Chem., 1993, pp. 2373-2380, vol. 36.
Lee, Jeewoo, et al., "Analysis of Structure-Activity Relationships for the 'B-region' of N-(4-t-butylbenzyl)-N'[4-(methylsulfonylamino) benzyl]-thiourea analogues as TRPV1 antagonists", Bioorganic & Medicinal Chemistry Letters, 2005, pp. 4143-4150, vol. 15.
German Search Report dated Feb. 8, 2006 with English translation (nine (9) pages).
International Preliminary Report on Patentability and Form PCT/ISA/237 dated Aug. 30, 2006 with English translation (twenty-two (22) pages).
I.-J You et al., Society for Neuroscience. Abstract. vol. 912.22 (2007).
Donnerer J. et al., Pharmacology. Feb. 2005; vol. 73, Issue 2, pp. 97-101 (2005). E pub Oct. 18, 2004.
G. Ahern, Activation of TRPV1 by the Satiety Factor Oleoylethanolamide, The Journal of Biological Chemistry, vol. 278, No. 33, Aug. 15, pp. 30429-30434, 2003.
L.A. Birder et al., Altered urinary bladder function in mice lacking the vanilloid receptor TRPV1, Nature Neuroscience, vol. 5, No. 9, Sep. 2002, pp. 856-860.
E. Bodo et al., A Hot New Twist to Hair Biology: Involvement of Vanilloid Receptor-1 (VR1/TRPV1) Signaling in Human Hair Growth Control, American Journal of Pathology, vol. 166, No. 4, Apr. 2005, pp. 985-998.

(Continued)

Primary Examiner — Sun Jae Loewe
(74) Attorney, Agent, or Firm — Crowell & Moring LLP

(57) ABSTRACT

The present invention relates to substituted cyclic urea derivatives corresponding to formula I, to processes for the preparation thereof, to medicinal drugs containing such compounds, to the use of such compounds in the preparation of medicinal drugs and in related treatment methods.

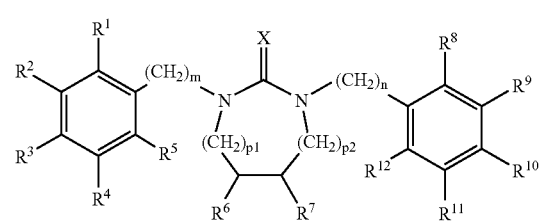

25 Claims, No Drawings

OTHER PUBLICATIONS

D. Dawbarn et al., Intranigral Injection of Capsaicin Enhances Motor Activity and Depletes Nigral 5-Hydroxytryptamine But Not Substance P, Neuropharmacology, vol. 20, pp. 341-346, 1981.
P. Geppetti et al., Activation and sensitisation of the vanilloid receptor: role in gastrointestinal inflammation and function, British Journal of Pharmacology, 2004, vol. 141, No. 8, pp. 1313-1320.
J. Ghilardi et al., Selective Blockade of the Capasicin Receptor TRPV1 Attenuates Bone Cancer Pain, The Jounral of Neuroscience, Mar. 23, 2005, vol. 25, No. 12, pp. 3126-3131.
P. Holzer, TRPV1 and the gut: from a tasty receptor for a painful vanilloid to a key player in hyperalgesia, European Journal of Pharmacology 500, 2004, pp. 231-241.
H. Rami et al., The therapeutic potential of TRPV1 (VRI) antagonists: clinical answers await, Drug Discover Today: Therapeutic Strategies, vol. 1, No. 1, 2004, pp. 97-104.
C. Maggi, Therapeutic Potential of Capsaicin-like Molecules: Studies in Animals and Humans, Life Sciences, vol. 51, pp. 1777-1781, 1992.
S. Marinelli et al., Presynaptic Facilitation of Glutamatergic Synapses to Dopaminergic Neurons of the Rat Substantia Nigra by Endogenous Stimulation of Vanilloid Receptors, The Journal of Neuroscience, Apr. 15, 2003, vol. 23, No. 8, pp. 3136-3144.
H. Pan et al., Sensing Tissue Ischemia: Another New Function for Capsaicin Receptors?, Circulation Journal of the American Heart Association, Circulation 2004, vol. 110, Issue 13, pp. 1826-1831.
H. Schultz, The spice of life is at the root of cardiac pain, Journal of Physiology (2003) 551.2, p. 400.
Y. Yaingou et al., Vanilloid receptor 1 immunoreactivity in inflamed human bowel, The Lancet, vol. 357, p. 1338-1339, Apr. 28, 2001.
M. Zahner et al., Cardiac vanilloid receptor 1-expressing afferent nerves and their role in the cardiogenic sympathetic reflex in rats, Journal of Physiology (2003) 551.2, pp. 515-523.
T. Sprenger et al., Migraine pathogenesis and state of pharmacological treatment options, BMC Medicine 2009, 7:71.
G.A. Lambert et al., The effects of the TRPV1 receptor antagonist SB-705498 on trigeminovascular sensitisation and neurotransmission, Nauyn-Schmied Arch Pharmacol (2009) vol. 380, pp. 311-325.
R. Planells-Cases et al., Functional aspects and mechanisms of TRPV1 involvement in neurogenic inflammation that leads to thermal hyperalgesia, Pflugers Arch—Eur J. Physiol (2005) vol. 451, pp. 151-159.
V. Micale et al., Altered responses of dopamine D3 receptor null mice to excitotoxic or anxiogenic stimuli: Possible involvement of the endocannabinoid and endovanilloid systems, Neurobiology of Disease 36 (2009), pp. 70-80.
M. Fu et al., TRPV1: A potential target for antiepileptogenesis, Medical Hypotheses 73 (2009), pp. 100-102.
F. Leung, Capsaicin-sensitive intestinal mucosal afferent mechanism and body fat distribution, Life Sciences 83 (2008), pp. 1-5.
A. Suri et al., The emerging role of TRPV1 in diabetes and obesity, Trends in Pharmacological Sciences, vol. 29, No. 1, pp. 29-36 (2007).
J. Li et al., Increased GFR and renal excretory function by activation of TRPV in the isolated prefused kidney, Pharmacological Research vol. 57, Issue 3 (2008), pp. 239-246.
M. Ghasemi et al., Effect of anandamide on nonadrenergic noncholinergic-mediated relaxation of rat corpus cavernosum, European Journal of Pharmacology vol. 544, Issues 1-3 (2006), pp. 138-145.
S. Mandadi et al., Locomotor Networks Are Targets of Modulation by Sensory Transient Receptor Potential Vanilloid 1 and Transient Receptor Potential Melastatin 8 Channels, Neuroscience 162 (2009) pp. 1377-1397.
R. Marsch et a., Reduced Anxiety, Conditioned Fear, and Hippocampal Long-Term Potentiation in Transient Receptor Potential Vanilloid Type 1 Receptor-Deficient Mice, The Journal of Neuroscience, Jan. 24, 2007, vol. 27, No. 4, pp. 832-839.
H. Eilers, Anesthetic Activation of Nociceptors: Adding Insult to Injury?, Molecular Interventions, Oct. 2008, vol. 8, Issue 5, pp. 226-229.
Won-Sik Shim et al., TRPV1 Mediates Histamine-Induced Itching via the Activation of Phospolipase $A_2$ and 12-Lipoxygenase, The Journal of Neuroscience, Feb. 28, 2007, vol. 27, No. 9, pp. 2331-2337.
W. Huang, Enhanced postmyocardial infarction fibrosis via stimulation of the transforming growth factor-B-Smad2 signaling pathway: role of transient receptor potential vanilloid type 1 channels, Journal of Hypertension vol. 27 (2009).
Yetkin Goek et al., Chalcogeno Ureas Derived from Bis(1,3-diazepan-2-Ylidene), Turk J. Chem., Department of Chemistry, Inoenil University, Malatya-Turkey, pp. 157-162.
J. Sandstrom et al., "Studies of Polarized Ethylenes—VIII Conformational Analysis of Twisted Ethylenes", Divison of Organic Chemistry I, Chemical Center, University of Luad, vol. 34, pp. 371-378.
Barbara Serafin et al., "Alkylation of Some Cyano Derivatives of Benzimidazoles", Institute of Organic Chemistry and Technolgy, Polytechnical University, Roczniki Chemii, Ann. Soc. Chim. Polonorum 51, (1977), pp. 2355-2368.
Arthur M. Felix et al., "Oxidation of 2,4-Benzodiazepin-3-ones", Chemical Research Departement, Hoffmann-La Roche Inc., Apr. 1968, pp. 291-293.
Robert L. Clark et al., "Synthesis of Some Substituted Benzimidazolones", Synthesis of Substituted Benzimidazolones, vol. 80, Contribution from the Merck Sharp & Dohme Research Laboratories, Apr. 5, 1958, pp. 1657-1662.

* cited by examiner

SUBSTITUTED CYCLIC UREA DERIVATIVES AND THE USE THEREOF AS VANILLOID RECEPTOR 1 MODULATORS

CROSS REFERENCE TO RELATED APPLICATIONS

This application is a continuation of PCT International Application No. PCT/EP2006/003519, filed Apr. 18, 2006, which claims priority under 35 U.S.C. §119 to German Patent Application No. 10 2005 018 191.0 filed Apr. 19, 2005, the entire disclosures of which are herein expressly incorporated by reference.

FIELD OF THE INVENTION

The present invention relates to substituted cyclic urea derivatives, to processes for the preparation thereof, to medicinal drugs containing these compounds and to the use of these compounds for the preparation of medicinal drugs.

BACKGROUND AND SUMMARY OF THE INVENTION

The treatment of pain, particularly neuropathic pain, is of great significance in the medical field. There is a global need for effective pain therapies. The urgent need for action to provide a patient-friendly and specific treatment for chronic and non-chronic states of pain, this being taken to mean the successful and satisfactory treatment of pain for patients, is documented by the large number of scientific papers which have recently appeared in the field of applied analgetics or in basic research concerning nociception.

A suitable starting point for the treatment of pain; particularly pain selected from the group consisting of acute pain, chronic pain, neuropathic pain, and visceral pain and more preferably neurophatic pain; is the vanilloid receptor of subtype 1 (VR1/TRPV1), which is frequently also referred to as the capsaicin receptor. This receptor is stimulated, inter alia, by vanilloids such as capsaicin, heat, and protons and plays a central part in the generation of pain. Furthermore, it is significant for a large number of other physiological and pathophysiological processes such as migraine; depression; neurodegenerative disorders; cognitive disorders; anxiety; epilepsy; coughing; diarrhoea; pruritus; cardiovascular disorders; food intake disorders; medicine addiction; medicine abuse and, in particular, urinary incontinence.

It is thus an object of the invention to provide novel compounds which are particularly suitable for use as pharmacological active substances in medicinal drugs, preferably in medicinal drugs for treatment of disorders or diseases that are at least partially mediated by vanilloid receptors 1 (VR1/TRPV1 receptors).

It has now been found, surprisingly, that substituted cyclic urea derivatives of the following general formula I have excellent affinity toward the vanilloid receptor of subtype 1 (VR1/TRPV1 receptor) and are therefore particularly suitable for the prophylaxis and/or treatment of disorders or diseases that are at least partially mediated by vanilloid receptors 1 (VR1/TRPV1).

The present invention therefore relates to substituted cyclic urea derivatives of the general formula I,

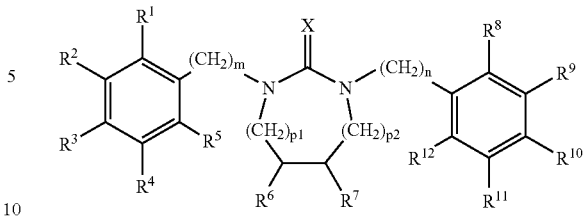

in which
X stands for O, S or N—C≡N;
m is equal to 1 or 2;
n is equal to 1 or 2;
p1 and p2 independently
stand for 0, 1, 2, or 3, the sum of p1 and p2 being 1, 2, or 3;
$R^1$, $R^2$, $R^3$, $R^4$, $R^5$, $R^8$, $R^9$, $R^{10}$, $R^{11}$ and $R^{12}$ independently stand for H; F; Cl; Br; I; —$SF_5$; —$NO_2$; —$NH_2$; —OH; —SH; —C(=O)—$NH_2$;
—S(=O)$_2$—$NH_2$;
—$NR^{13}R^{14}$; —NH—$R^{15}$; —$OR^{16}$; —$SR^{17}$; —O—$(CH_2)_a$—$R^{18}$; —O—$(CH_2)_b$—$OR^{19}$;
—$(CH_2)_c$—O—$(CH_2)_d$—$OR^{20}$;
—$(CH_2)_e$—O—C(=O)—$R^{21}$;
—$(CH_2)_f$—O—C(=O)—$OR^{22}$;
—$NR^{23}S(=O)_2R^{24}$;
—$(CH_2)_g$—C(=O)—$NR^{25}R^{26}$;
—$(CH_2)_h$—C(=O)—NH—$R^{27}$;
—S(=O)$_i$$R^{28}$;
—$(CH_2)_j$—S(=O)$_2$—$NR^{29}R^{30}$;
—$(CH_2)_k$—S(=O)$_2$—$NHR^{31}$;
—$(CH_2)_l$—$NR^{32}$—C(=O)$(CH_2)_q$—$OR^{33}$;
—$(CH_2)_r$—NH—C(=O)$(CH_2)_s$—$OR^{34}$;
—$(CH_2)_t$—$NR^{35}$—O—C(=O)—$OR^{36}$;
—$(CH_2)_u$—NH—O—C(=O)—$OR^{37}$;
—$(CH_2)_v$—O—S(=O)$_2$—$R^{38}$;
—$(CH_2)_w$—$NR^{39}$—C(=O)—$SR^{40}$;
—$(CH_2)_y$—C(=O)—NH—$OR^{41}$;
—P(=O)(O$R^{42}$)$_2$;
—$(CH_2)_z$—C(=S)—$NR^{43}R^{44}$;
—$(CH_2)_{aa}$—C(=S)—NH—$R^{45}$;
—$(CH_2)_{bb}$—$NR^{46}$—C(=O)—$R^{47}$;
—$(CH_2)_{cc}$—NH—C(=O)—$R^{48}$;
or —NH—C(=NH)—$NH_2$;
with a, b, c, d, q and s independently standing for 1, 2, 3, 4, or 5 and
e, f, g, h, j, k, l, r, t, u, v, w, x, y, z, aa, bb and cc independently standing for 0, 1, 2, 3, 4, or 5, and
i being equal to 1 or 2
for a linear or branched, saturated or unsaturated aliphatic $C_{1-10}$ radical, which can optionally be substituted by 1, 2, 3, 4, 5, 6, 7, 8, or 9 substituents independently selected from the group consisting of F, Cl, Br, I, —CN, —$NO_2$, —OH, —$NH_2$, —SH, —O($C_{1-5}$ alkyl), —S($C_{1-5}$ alkyl), —NH($C_{1-5}$ alkyl), —N($C_{1-5}$ alkyl)($C_{1-5}$ alkyl), —$OCF_3$ and —$SCF_3$;
or for an optionally substituted six-membered or ten-membered aryl radical, which can be bonded via a linear or branched, optionally substituted $C_{1-5}$ alkylene group;
or two adjacent radicals selected from the group consisting of $R^8$, $R^9$, $R^{10}$, $R^{11}$ and $R^{12}$ together stand for a methylenedioxy(—O—$CH_2$—O) group;
provided that at least one of the radicals $R^8$, $R^9$, $R^{10}$, $R^{11}$ and $R^{12}$ stands for —$NR^{23}S(=O)_2R^{24}$;
$R^6$ and $R^7$ each stand for a hydrogen radical or $R^6$ and $R^7$, together with the interconnecting C—C bridge, form an unsubstituted phenylene radical;

$R^{13}, R^{14}, R^{15}, R^{16}, R^{17}, R^{19}, R^{20}, R^{21}, R^{22}, R^{25}, R^{26}, R^{27}, R^{28}, R^{29}, R^{30}, R^{31}, R^{32}, R^{33}, R^{34}, R^{35}, R^{36}, R^{37}, R^{38}, R^{39}, R^{40}, R^{41}, R^{42}, R^{43}, R^{44}, R^{45}, R^{46}, R^{47}$ and $R^{48}$ independently stand for a linear or branched, saturated or unsaturated aliphatic $C_{1-10}$ radical, which can be optionally substituted by 1, 2, 3, 4, 5, 6, 7, 8, or 9 substituents independently selected from the group consisting of F, Cl, Br, I, —CN, —NO$_2$, —OH, —NH$_2$, —SH, —O(C$_{1-5}$ alkyl), —S(C$_{1-5}$ alkyl), —NH(C$_{1-5}$ alkyl), —N(C$_{1-5}$ alkyl)(C$_{1-5}$ alkyl), —OCF$_3$, and —SCF$_3$;

or for an unsaturated or saturated, optionally substituted three-membered, four-membered, five-membered, six-membered, seven-membered, eight-membered, or nine-membered cycloaliphatic radical or for an optionally substituted five-membered to fourteen-membered aryl radical or an optionally substituted five-membered to fourteen-membered heteroaryl radical, which can be condensed with a saturated or unsaturated, optionally substituted monocyclic or polycyclic ring system;

$R^{18}$ stands for an unsaturated or saturated, optionally substituted three-membered, four-membered, five-membered, six-membered, seven-membered, eight-membered, or nine-membered cycloaliphatic radical or for an optionally substituted five-membered to fourteen-membered aryl radical or an optionally substituted five-membered to fourteen-membered heteroaryl radical, which can be condensed with a saturated or unsaturated, optionally substituted monocyclic or polycyclic ring system;

$R^{23}$ stands for a hydrogen radical or for a linear or branched, saturated or unsaturated or aliphatic $C_{1-10}$ radical, which can optionally be substituted by 1, 2, 3, 4, 5, 6, 7, 8, or 9 substituents independently selected from the group consisting of F, Cl, Br, I, —CN, —NO$_2$, —OH, —NH$_2$, —SH, —O(C$_{1-5}$ alkyl), —S(C$_{1-5}$ alkyl), —NH(C$_{1-5}$ alkyl), —N(C$_{1-5}$ alkyl)(C$_{1-5}$ alkyl), —OCF$_3$, and —SCF$_3$;

and $R^{24}$ stands for a linear or branched, saturated or unsaturated or aliphatic $C_{1-10}$ radical, which can optionally be substituted by 1, 2, 3, 4, or 5 substituents independently selected from the group consisting of —CN, —NO$_2$, —OH, —NH$_2$, —SH, —O(C$_{1-5}$ alkyl), —S(C$_{1-5}$ alkyl), —NH(C$_{1-5}$ alkyl), and —N(C$_{1-5}$ alkyl)(C$_{1-5}$ alkyl), or for an optionally substituted 5-membered to 14-membered aryl or heteroaryl radical, which may be condensed with a saturated or unsaturated, optionally substituted mono-oder poly-cyclic ring system;

in each case optionally in the form of one of the pure stereoisomers thereof, particularly enantiomers or diastereoisomers, or the racemates thereof or in the form of a mixture of stereoisomers, particularly the enantiomers and/or diastereoisomers, in an arbitrary mixing ratio, or in each case in the form of corresponding salts, or in each case in the form of corresponding solvates.

Preferably, the aforementioned cycloaliphatic radicals can optionally in each case be substituted by 1, 2, 3, 4, or 5 substituents independently selected from the group consisting of oxo (═O), thioxo (═S), F, Cl, Br, I, —CN, —CF$_3$, —SF$_5$, —OH, —O—C$_{1-5}$ alkyl, —NH$_2$, —NO$_2$, —O—CF$_3$, —S—CF$_3$, —SH, —S—C$_{1-5}$ alkyl, —C$_{1-5}$ alkyl, —C(═O)—OH, —C(═O)—O—C$_{1-5}$ alkyl, —NH—C$_{1-5}$ alkyl, —N(C$_{1-5}$ alkyl)$_2$, —O-phenyl, —O-benzyl, phenyl, and benzyl, and in each case the cyclic moiety of the radicals —O-phenyl, —O-benzyl, phenyl, and benzyl can be substituted by 1, 2, 3, 4, or 5 substituents independently selected from the group consisting of F, Cl, Br, —OH, —CF$_3$, —SF$_5$, —CN, —NO$_2$, —C$_{1-5}$ alkyl, —O—C$_{1-5}$ alkyl, —O—CF$_3$, —S—CF$_3$, phenyl, and —O-benzyl, and in each case optionally exhibit 1, 2, 3, 4, or 5 heteroatom(s) independently selected from the group consisting of oxygen, nitrogen, and sulfur as ring member(s).

Preferably, the aforementioned $C_{1-5}$ alkylene group can optionally be substituted by 1, 2, 3, 4, or 5 substituents independently selected from the group consisting of F, Cl, Br, —OH, —SH, —NH$_2$, —CN, and NO$_2$.

In another preferred embodiment the rings of the aforementioned monocyclic or polycyclic ring systems can optionally in each case be substituted by 1, 2, 3, 4, or 5 substituents independently selected from the group consisting of oxo (═O), thioxo (═S), F, Cl, Br, I, —CN, —CF$_3$, —SF$_5$, —OH, —O—C$_{1-15}$ alkyl, —NH$_2$, —NO$_2$, —O—CF$_3$, —S—CF$_3$, —SH, —S—C$_{1-5}$ alkyl, —C$_{1-5}$ alkyl, —C(═O)—OH, —C(═O)—O—C$_{1-5}$ alkyl, —NH—C$_{1-5}$ alkyl, —N(C$_{1-5}$ alkyl)$_2$, —O-phenyl, —O-benzyl, phenyl, and benzyl, and in each case the cyclic moiety of the radicals —O-phenyl, —O-benzyl, phenyl, and benzyl can be substituted by 1, 2, 3, 4, or 5 substituents independently selected from the group consisting of F, Cl, Br, —OH, —CF$_3$, —SF$_5$, —CN, —NO$_2$, —C$_{1-5}$ alkyl, —O—C$_{1-5}$ alkyl, —O—CF$_3$, —S—CF$_3$, phenyl, and —O-benzyl.

Preferably, the rings of the aforementioned monocyclic or polycyclic ring systems are each five-membered, six-membered, or seven-membered and can in each case optionally exhibit 1, 2, 3, 4, or 5 heteroatom(s) as ring member(s), which are independently selected from the group consisting of oxygen, nitrogen, and sulfur.

In another preferred embodiment, the aforementioned aryl radicals or heteroaryl radicals can optionally in each case be substituted by 1, 2, 3, 4, or 5 substituents independently selected from the group consisting of F, Cl, Br, I, —CN, —CF$_3$, —SF$_5$, —OH, —O—C$_{1-5}$ alkyl, —NH$_2$, —NO$_2$, —O—CF$_3$, —S—CF$_3$, —SH, —S—C$_{1-5}$ alkyl, —C$_{1-5}$ alkyl, —C(═O)—OH, —C(═O)—O—C$_{1-5}$ alkyl, —NH—C$_{1-5}$ alkyl, —N(C$_{1-5}$ alkyl)$_2$, —NH—C(═O)—O—C$_{1-5}$ alkyl, —C(═O)—H, —C(═O)—C$_{1-5}$ alkyl, —C(═O)—NH$_2$, —C(═O)—NH—C$_{1-5}$ alkyl, —C(═O)—N—(C$_{1-5}$ alkyl)$_2$, —O-phenyl, —O-benzyl, phenyl, and benzyl, and in each case the cyclic moiety of the radicals —O-phenyl, —O-benzyl, phenyl, and benzyl can be substituted by 1, 2, 3, 4, or 5 substituents independently selected from the group consisting of F, Cl, Br, —OH, —CF$_2$, —SF$_{1-5}$, —CN, —NO$_{1-5}$, —C$_3$ alkyl, —O—C$_3$ alkyl, —O—CF$_3$, —S—CF$_3$, phenyl, and —O-benzyl.

In another preferred embodiment, the aforementioned heteroaryl radicals in each case comprise 1, 2, 3, 4, or 5 heteroatom(s) independently selected from the group consisting of oxygen, nitrogen, and sulfur as ring member(s).

If one or more of the substituents $R^1$ to $R^5$, $R^8$ to $R^{17}$, $R^{19}$ to $R^{23}$ and $R^{25}$ to $R^{48}$ stand for a saturated or unsaturated $C_{1-10}$ aliphatic radical, ie for a $C_{1-10}$ alkyl, $C_{2-10}$ alkenyl, or $C_{2-10}$ alkinyl radical, this can preferably be substituted by optionally 1, 2, 3, 4, 5, 6, 7, 8, or 9 substituents independently selected from the group consisting of F, Cl, Br, I, —CN, —NO$_2$, —OH, —NH$_2$, —SH, —O(C$_{1-5}$ alkyl), —S(C$_{1-5}$ alkyl), —NH(C$_{1-5}$ alkyl), —N(C$_{1-5}$ alkyl)(C$_{1-5}$ alkyl), —OCF$_3$, and —SCF$_3$. $C_{2-10}$ alkenyl radicals have at least one, preferably 1, 2, 3, or 4 C—C double bonds and $C_{2-10}$ alkinyl radicals have at least one, preferably 1, 2, 3, or 4 C—C triple bonds.

Preference is given to alkyl radicals selected from the group consisting of methyl, ethyl, n-propyl, isopropyl, n-butyl, sec-butyl, isobutyl, tert-butyl, n-pentyl, sec-pentyl, neopentyl, and n-hexyl, which can optionally be substituted by 1, 2, 3, 4, 5, 6, 7, 8, or 9 substituents independently selected from the group consisting of F, Cl, Br, I, —CN, —$NO_2$, —OH, —$NH_3$, —SH, —$OCH_5$, —O—$C_2H_5$, —$SCH_3$, —S—$C_2H_5$, —$OCF_3$, —$SCF_3$, —NH—$CH_3$, —N($CH_3$)$_2$, —N($C_2H_5$)$_2$, and —N($CH_3$)($C_2H_5$).

In another preferred embodiment, alkenyl radicals are selected from the group consisting of vinyl, 1-propenyl, 2-propenyl, 1-butenyl, 2-butenyl, 3-butenyl, 2-methylbuten-2-yl, 1-pentenyl, 2-pentenyl, 3-pentenyl, and 4-pentenyl, which can optionally be substituted by 1, 2, or 3 substituents independently selected from the group consisting of F, Cl, Br, I, —CN, —$NO_2$, —OH, —$NH_2$, —SH, —$OCH_5$, —O—$C_2H_5$, —$SCH_3$, —S—$C_2H_5$, —$OCF_3$, —$SCF_3$, —NH—$CH_3$, —N($CH_3$)$_2$, —N($C_2H_5$)$_2$, and —N($CH_3$)($C_2H_5$).

Preference is also given to alkinyl radicals selected from the group consisting of ethinyl, 1-propinyl, 2-propinyl, 1-butinyl, 2-butinyl, and 3-butinyl, which can optionally be substituted by 1, 2, or 3 substituents independently selected from the group consisting of F, Cl, Br, I, —CN, —$NO_2$, —OH, —$NH_2$, —SH, —$OCH_3$, —O—$C_2H_5$, —$SCH_3$, —S—$C_2H_5$, —$OCF_3$, —$SCF_3$, —NH—$CH_3$, —N($CH_3$)$_2$, —N($C_2H_5$)$_2$, and —N($CH_3$)($C_2H_5$).

Very preferred optionally substituted $C_{1-10}$ aliphatic radicals are selected from the group consisting of methyl, —$CF_3$, —$CCl_3$, —$CBr_3$, —$CH_2$—CN, —$CH_2$—O—$CH_3$, —$CH_2$—O—$CF_3$, —$CH_2$—$SF_3$, —$CH_2$—$NH_2$, —$CH_2$—OH, —$CH_2$—SH, —$CH_2$—NH—$CH_3$, —$CH_2$—N($CH_3$)$_2$, —$CH_2$—N($C_2H_5$)$_2$, —$CH_2$—N($CH_3$)($C_2H_5$), ethyl, —$CH_2$—$CH_2$—$NH_2$, —$CH_2$—$CH_2$—OH, —$CH_2$—$CH_2$—SH, —$CH_2$—$CH_2$—NH—$CH_3$, —$CH_2$—$CH_2$—N($CH_3$)$_2$, —$CH_2$—$CH_2$—N($C_2H_5$)$_2$, —$CH_2$—$CH_2$—N($CH_3$)($C_2H_5$), —$CH_2$—$CF_3$, —$C_2F_5$, —$CH_2$—$CCl_3$, —$CH_2$—$CBr_3$, —$CH_2$—$CH_2$—CN, n-propyl, —$CH_2$—$CH_2$—$CH_2$—OH, —$CH_2$—$CH_2$—$CH_2$—SH, —$CH_2$—$CH_2$—$CH_2$—$NH_2$, —$CH_2$—$CH_2$—$CH_2$—NH—$CH_3$, —$CH_2$—$CH_2$—$CH_2$—N($CH_3$)$_2$, —$CH_2$—$CH_2$—$CH_2$—N($C_2H_5$)$_2$, —$CH_2$—$CH_2$—$CH_2$—N($CH_3$)($C_2H_5$), —$CH_2$—$CH_2$—O—$CH_3$, —$CF_2$—$CF_2$—$CF_3$, —CF($CF_3$)$_2$, isopropyl, —$CH_2$—$CH_2$—$CH_2$—CN, —$CH_2$—O—$CH_2$—$CH_3$, —$CH_2$—$CH_2$—$SF_3$, —$CH_2$—$CH_2$—$OCF_3$, —CH($CH_3$)(O—$CH_3$), —CH($CH_3$)(S—$CH_3$), n-butyl, —$CF_2$—$CF_2$—$CF_2$—$CF_3$, —$CH_2$—$CH_2$—$CH_2$—$CH_2$—CN, sec-butyl, isobutyl, tert-butyl, n-pentyl, sec-pentyl, neopentyl, n-hexyl, vinyl, 1-propenyl, 2-propenyl, 1-butenyl, 2-butenyl, 3-butenyl, 2-methylbuten-2-yl, (1,1,2)-trifluoro-1-butenyl, 1-pentenyl, 2-pentenyl, 3-pentenyl, and 4-pentenyl.

If the substituent $R^{24}$ stands for a saturated or unsaturated $C_{1-10}$ aliphatic radical, ie for a $C_{1-10}$ alkyl, $C_{2-10}$ alkenyl, or $C_{2-10}$ alkinyl radical, this can preferably be substituted by optionally 1, 2, 3, 4, or 5 substituents independently selected from the group consisting of —CN, —$NO_2$, —OH, —$NH_2$, —SH, —O($C_{1-5}$ alkyl), —S($C_{1-5}$ alkyl), —NH($C_{1-5}$ alkyl), and —N($C_{1-5}$ alkyl)($C_{1-5}$ alkyl). $C_{2-10}$ alkenyl radicals exhibit at least one, preferably 1, 2, 3, or 4 C—C double bonds and $C_{2-10}$ alkinyl radicals at least one, preferably 1, 2, 3, or 4 C—C triple bonds.

Preferably, $R^{24}$ stands for an alkyl radical selected from the group consisting of methyl, ethyl, n-propyl, isopropyl, n-butyl, sec-butyl, isobutyl, tert-butyl, n-pentyl, sec-pentyl, neopentyl, and n-hexyl, which can optionally be substituted by 1, 2, 3, 4, or 5 substituents independently selected from the group consisting of —OH, —$NH_2$, —SH, —$NO_2$, —O—$CH_3$, —S—$CH_3$, —O—$C_2H_5$, —S—$C_2H_5$, —NH—$CH_3$, —N($CH_3$)$_2$, and —CN.

In another preferred embodiment, $R^{24}$ stands for an alkenyl radical selected from the group consisting of vinyl, 1-propenyl, 2-propenyl, 1-butenyl, 2-butenyl, 3-butenyl, 2-methylbuten-2-yl, 1-pentenyl, 2-pentenyl, 3-pentenyl, and 4-pentenyl, which can optionally be substituted by 1, 2, or 3 substituents independently selected from the group consisting of —OH, —$NH_2$, —SH, —$NO_2$, —O—$CH_3$, —S—$CH_3$, —O—$C_2H_5$, —S—$C_2H_5$, —NH—$CH_3$, —N($CH_3$)$_2$, and —CN.

In another preferred embodiment, $R^{24}$ stands for an alkinyl radical selected from the group consisting of ethinyl, 1-propinyl, 2-propinyl, 1-butinyl, 2-butinyl, and 3-butinyl, which can optionally be substituted by 1, 2, or 3 substituents independently selected from the group consisting of —OH, —$NH_2$, —SH, —$NO_2$, —O—$CH_3$, —S—$CH_3$, —O—$C_2H_5$, —S—$C_2H_5$, —NH—$CH_3$, —N($CH_3$)$_2$, and —CN.

More preferably, $R^{24}$ stands for an optionally substituted $C_{1-10}$ aliphatic radical selected from the group consisting of methyl, —$CH_2$—CN, —$CH_2$—O—$CH_3$, ethyl, —$CH_2$—$CH_3$—CN, n-propyl, —$CH_2$—$CH_2$—O—$CH_3$, isopropyl, —$CH_2$—$CH_2$—$CH_2$—CN, —$CH_2$—O—$CH_2$—$CH_3$, —CH($CH_3$)(O—$CH_3$), —CH($CH_3$)(S—$CH_3$), n-butyl, sec-butyl, isobutyl, tert-butyl, n-pentyl, sec-pentyl, neopentyl, n-hexyl, vinyl, 1-propenyl, 2-propenyl, 1-butenyl, 2-butenyl, 3-butenyl, 2-methylbuten-2-yl, 1-pentenyl, 2-pentenyl, 3-pentenyl, and 4-pentenyl.

If one or more of the substituents $R^{13}$ to $R^{22}$ and $R^{25}$ to $R^{48}$ stand for a (hetero)cycloaliphatic radical, this can preferably be selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl, and dithiolanyl.

More preferably, the (hetero)cycloaliphatic radicals can optionally in each case be substituted by 1, 2, 3, 4, or 5 substituents independently selected from the group consisting of oxo (=O), thioxo (=S), F, Cl, Br, I, —CN, —$CF_3$, —$SF_5$, —OH, —O—$CH_3$, —O—$C_2H_5$, —O—C($CH_3$)$_3$, —$NH_2$, —$NO_2$, —O—$CF_3$, —$SCF_3$, —SH, —S—$CH_3$, —S—$C_2H_5$, —S—C($CH_3$)$_3$, methyl, ethyl, n-propyl, isopropyl, n-butyl, sec-butyl, isobutyl, tert-butyl, n-pentyl, sec-pentyl, —C(=O)—OH, —C(=O)—O—$CH_3$, —C(=O)—O—$C_2H_5$, —N($CH_3$)$_2$, —N($C_2H_5$)$_2$, —N(H)($CH_3$), —N(H)($C_2H_5$), —O-phenyl, —O-benzyl, phenyl, and benzyl, and in each case the cyclic moiety of the radicals —O-phenyl, —O-benzyl, phenyl, and benzyl can be substituted by 1, 2, 3, 4, or 5 substituents independently selected from the group consisting of F, Cl, Br, —OH, —$CF_3$, —$SF_5$, —CN, —$NO_2$, methyl, ethyl, n-propyl, isopropyl, n-butyl, isobutyl, tert-butyl, —O—$CH_3$, —O—$C_2H_5$, —O—C($CH_3$)$_3$, —O—$CF_3$, —S—$CF_3$, phenyl, and —O-benzyl.

If one or more of the substituents $R^1$ to $R^5$, $R^8$ to $R^{22}$, and $R^{24}$ to $R^{48}$ stand for an aryl radical, this can preferably be selected from the group consisting of phenyl and naphthyl (1-naphthyl and 2-naphthyl).

If one or more of the substituents $R^{13}$ to $R^{22}$ and $R^{24}$ to $R^{48}$ stand for a heteroaryl radical, this can preferably be selected from the group consisting of thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinoxalinyl, quinolinyl, and isoquinolinyl.

More preferably, the aryl radicals or heteroaryl radicals can optionally in each case be substituted by 1, 2, 3, 4, or 5 substituents independently selected from the group consisting of F, Cl, Br, I, —CN, —CF$_3$, —SF$_5$, —OH, —O—CH$_3$, —O—C$_2$H$_5$, —O—C(CH$_3$)$_3$, —NH$_2$, —NO$_2$, —O—CF$_3$, —S—CF$_3$, —SH, —S—CH$_3$, —S—C$_2$H$_5$, —S—C(CH$_3$)$_3$, methyl, ethyl, n-propyl, isopropyl, n-butyl, sec-butyl, isobutyl, tert-butyl, —C(=O)—OH, —C(=O)—O—CH$_3$, —C(=O)—O—C$_2$H$_5$, —N(CH$_3$)$_2$, —N(C$_2$H$_5$)$_2$, —N(H)(CH$_3$), —N(H)(C$_2$H$_5$), —NH—C(=O)—O—CH$_3$, —NH—C(=O)—O—C$_2$H$_5$, —NH—C(=O)—O—C(CH$_3$)$_2$, —C(=O)—H, —C(=O)—CH$_3$, —C(=O)—C$_2$H$_5$, —C(=O)—NH$_2$, —C(=O)—NH—CH$_3$, —C(=O)-nH—C$_2$H$_5$, —C(=O)—N—(CH$_3$)$_2$, —C(=O)—N—(C$_2$H$_5$)$_2$, —O-phenyl, —O-benzyl, phenyl, and benzyl, and in each case the cyclic moiety of the radicals —O-phenyl, —O-benzyl, phenyl, and benzyl can be substituted by 1, 2, 3, 4, or 5 substituents independently selected from the group consisting of F, Cl, Br, —OH, —CF$_3$, —SF$_5$, —CN, —NO$_2$, methyl, ethyl, n-propyl, isopropyl, n-butyl, isobutyl, tert-butyl, —O—CH$_3$, —O—C$_2$H$_5$, —O—C(CH$_3$)$_3$, —O—CF$_3$, —S—CF$_3$, phenyl, and —O-benzyl.

For the purposes of the present invention, a monocyclic or polycyclic ring system is to be understood as meaning monocyclic or polycyclic hydrocarbon groups, which can be saturated or unsaturated and optionally comprise 1, 2, 3, 4, or 5 heteroatom(s) as ring member(s), which are independently selected from the group consisting of oxygen, nitrogen, and sulfur. Such a monocyclic or polycyclic ring system can, for example, be condensed (anellated) with an aryl radical or a heteroaryl radical.

If a polycyclic ring system such as a bicyclic ring system is present, the various rings can independently exhibit a different degree of saturation, ie be saturated or unsaturated. A polycyclic ring system is preferably a bicyclic ring system.

As examples of aryl radicals condensed with a monocyclic or polycyclic ring system mention may be made of (1,3)-benzodioxolyl and (1,4)-benzodioxanyl.

If one or more of the substituents $R^{13}$ to $R^{22}$ and $R^{24}$ to $R^{48}$ have a monocyclic or polycyclic ring system, this can preferably be substituted by 1, 2, 3, 4, or 5 substituents independently selected from the group consisting of oxo (=O), thioxo (=S), F, Cl, Br, I, —CN, —CF$_3$, —SF$_5$, —OH, —O—CH$_3$, —O—C$_2$H$_5$, —O—C(CH$_3$)$_3$, —NH$_2$, —NO$_2$, —O—CF$_3$, —SCF$_3$, —SH, —S—CH$_3$, —S—C$_2$H$_5$, —S—C(CH$_3$)$_3$, methyl, ethyl, n-propyl, isopropyl, n-butyl, sec-butyl, isobutyl, tert-butyl, n-pentyl, sec-pentyl, —C(=O)—OH, —C(=O)—O—CH$_3$, —C(=O)—O—C$_2$H$_5$, —N(CH$_3$)$_2$, —N(C$_2$H$_5$)$_2$, —N(H)(CH$_3$), —N(H)(C$_2$H$_5$), —O-phenyl, —O-benzyl, phenyl, and benzyl, and in each case the cyclic moiety of the radicals —O-phenyl, —O-benzyl, phenyl, and benzyl can be substituted by 1, 2, 3, 4, or 5 substituents independently selected from the group consisting of F, Cl, Br, —OH, —CF$_3$, —SF$_5$, —CN, —NO$_2$, methyl, ethyl, n-propyl, isopropyl, n-butyl, isobutyl, tert-butyl, —O—CH$_3$, —O—C$_2$H$_5$, —O—C(CH$_3$)$_3$, —O—CF$_3$, —S—CF$_3$, phenyl, and —O-benzyl.

If one or more of the substituents $R^1$ to $R^5$ and $R^8$ to $R^{12}$ comprise a linear or branched $C_{1-5}$ alkylene group, this can preferably be selected from the group consisting of —(CH$_2$)—, —(CH$_2$)$_2$—, —C(H)(CH$_3$)—, —(CH$_2$)$_3$—, —(CH$_2$)$_4$—, —(CH$_2$)$_5$—, —C(H)(C(H)(CH$_3$)$_2$)—, and —C(C$_2$H$_5$)(H)—.

Preference is given to substituted cyclic urea derivatives of the above general formula I, in which
$R^1$, $R^2$, $R^4$, and $R^5$ each independently
stand for H; F; Cl; Br; I; —SF$_5$; —NO$_2$; —NH$_2$; —OH; —SH; —C(=O)—NH$_2$;
—S(=O)$_2$—NH$_2$;
—NR$^{13}$R$^{14}$; —NH—R$^{15}$; —OR$^{16}$; —SR$^{17}$; —O—(CH$_2$)$_a$—R$^{18}$; —O—(CH$_2$)$_b$—OR$^{19}$;
—(CH$_2$)$_c$—O—(CH$_2$)$_d$—OR$^{20}$;
—(CH$_2$)$_e$—O—C(=O)—R$^{21}$;
—(CH$_2$)$_f$O—C(=O)—OR$^{22}$;
—NR$^{23}$S(=O)$_2$R$^{24}$;
—(CH$_2$)$_g$—C(=O)—NR$^{25}$R$^{26}$;
(CH$_2$)$_h$—C(=O)—NH—R$^{27}$;
—S(=O)$_i$R$^{28}$;
—(CH$_2$)$_j$—S(=O)$_2$—NR$^{29}$R$^{30}$;
—(CH$_2$)$_k$—S(=O)$_2$—NHR$^{31}$;
—(CH$_2$)$_l$—NR$^{32}$—C(=O)(CH$_2$)$_q$—OR$^{33}$;
—(CH$_2$)$_r$—NH—C(=O)(CH$_2$)$_s$—OR$^{34}$;
—(CH$_2$)$_t$—NR$^{35}$—O—C(=O)—OR$^{36}$;
—(CH$_2$)$_u$—NH—O—C(=O)—OR$^{37}$;
—(CH$_2$)$_v$—O—S(=O)$_2$—R$^{38}$;
—(CH$_2$)$_w$—NR$^{39}$—C(=O)—SR$^{40}$;
—(CH$_2$)$_y$—C(=O)—NH—OR$^{41}$;
—P(=O)(OR$^{42}$)$_2$;
—(CH$_2$)$_z$—C(=S)—NR$^{43}$R$^{44}$;
—(CH$_2$)$_{aa}$—C(=S)—NH—R$^{45}$;
—(CH$_2$)$_{bb}$—NR$^{46}$—C(=O)—R$^{47}$;
—(CH$_2$)$_{cc}$—NH—C(=O)—R$^{48}$;
or —NH—C(=NH)—NH$_2$;
with a, b, and c, d, q and s each being independently equal to 1, 2, 3, 4, or 5,
e, f, and g, h, j, k, l, r, t, u, v, w, x, y, and z, aa, bb and cc each being independently equal to 1, 1, 2, 3, 4, or 5 and
i being equal to 1 or 2;
or for a radical selected from the group consisting of methyl, —CF$_3$, —CCl$_3$, —CBr$_3$, —CH$_2$—CN, —CH$_2$—O—CH$_3$, —CH$_2$—O—CF$_3$, —CH$_2$—SF$_3$, —CH$_2$—NH$_2$, —CH$_2$—OH, —CH$_2$—SH, —CH$_2$—NH—CH$_3$, —CH$_2$—N(CH$_3$)$_2$, —CH$_2$—N(C$_2$H$_5$)$_2$, —CH$_2$—N(CH$_3$)(C$_2$H$_5$), ethyl, —CH$_2$—CH$_2$—NH$_2$, —CH$_2$—CH$_2$—OH, —CH$_2$—CH$_2$—SH, —CH$_2$—CH$_2$—NH—CH$_3$, —CH$_2$—CH$_2$—N(CH$_3$)$_2$, —CH$_2$—CH$_2$—N(C$_2$H$_5$)$_2$, —CH$_2$—CH$_2$—N(CH$_3$)(C$_2$H$_5$), —CH$_2$—CF$_3$, —C$_2$F$_5$, —CH$_2$—CCl$_3$, —CH$_2$—CBr$_3$, —CH$_2$—CH$_2$—CN, n-propyl, —CH$_2$—CH$_2$—CH$_2$—OH, —CH$_2$—CH$_2$—CH$_2$—SH, —CH$_2$—CH$_2$—CH$_2$—NH$_2$, —CH$_2$—CH$_2$—CH$_2$—NH—CH$_3$, —CH$_2$—CH$_2$—CH$_2$—N(CH$_3$)$_2$, CH$_2$—CH$_2$—CH$_2$—N(C$_2$H$_5$)$_2$, —CH$_2$—CH$_2$—CH$_2$—N(CH$_3$)(C$_2$H$_5$), —CH$_2$—CH$_2$—O—CH$_3$, —CF$_2$—CF$_2$—CF$_3$, —CF(CF$_3$)$_2$, isopropyl, —CH$_2$—CH$_2$—CH$_2$—CN, —CH$_2$—O—CH$_2$—CH$_3$, —CH$_2$—CH$_2$—SF$_3$, —CH$_2$—CH$_2$—OCF$_3$, —CH(CH$_3$)(O—CH$_3$), —CH(CH$_3$)(S—CH$_3$), n-butyl, —CF$_2$—CF$_2$—CF$_2$—CF$_3$, —CH$_2$—CH$_2$—CH$_2$—CH$_2$—CN, sec-butyl, isobutyl, tert-butyl, n-pentyl, sec-pentyl, neopentyl, n-hexyl, vinyl, 1-propenyl, 2-propenyl, 1-butenyl, 2-butenyl, 3-butenyl, 2-methylbuten-2-yl, (1,1,2)-trifluoro-1-butenyl, 1-pentenyl, 2-pentenyl, 3-pentenyl, and 4-pentenyl;
or for an aryl radical selected from the group consisting of phenyl and naphthyl, wherein the aryl radical can be substituted by 1, 2, 3, 4, or 5 substituents independently selected from the group consisting of F, Cl, Br, I, —CN, —NO$_2$, —OH, —SH, methyl, ethyl, —CF$_3$, —O—CF$_3$, —S—CF$_3$, —SF$_5$, —O—CH$_3$, —O—C$_2$H$_5$, —NH$_2$, —N(CH$_3$)$_2$, —N(C$_2$H$_5$)$_2$, —N(H)(CH$_3$), and —N(H)(C$_2$H$_5$);

and

R$^3$ stands for F; Cl; Br; I; —SF$_5$; —NO$_2$; —NH$_2$; —OH; —SH; —C(=O)—NH$_2$; —S(=O)$_2$—NH$_2$; —NR$^{13}$R$^{14}$; —NH—R$^{15}$; —OR$^{16}$; —SR$^{17}$; —O—(CH$_2$)$_a$—R$^{18}$, —O—(CH$_2$)$_b$—OR$^{19}$, or —NR$^{23}$S(=O)$_2$R$^{24}$;

wherein a and b are each independently equal to 1, 2, 3, 4, or 5;

or for a radical selected from the group consisting of methyl, —CF$_3$, —CCl$_3$, —CBr$_3$, —CH$_2$—CN, —CH$_2$—O—CH$_3$, —CH$_2$—O—CF$_3$, —CH$_2$—SF$_3$, —CH$_2$—NH$_2$, —CH$_2$—OH, —CH$_2$—SH, —CH$_2$—NH—CH$_3$, —CH$_2$—N(CH$_3$)$_2$, —CH$_2$—N(C$_2$H$_5$)$_2$, —CH$_2$—N(CH$_3$)(C$_2$H$_5$), ethyl, —CH$_2$—CH$_2$—NH$_2$, —CH$_2$—CH$_2$—OH, —CH$_2$—CH$_2$—SH, —CH$_2$—CH$_2$—NH—CH$_3$, —CH$_2$—CH$_2$—N(CH$_3$)$_2$, —CH$_2$—CH$_2$—N(C$_2$H$_5$)$_2$, —CH$_2$—CH$_2$—N(CH$_3$)(C$_2$H$_5$), —CH$_2$—CF$_3$, —C$_2$F$_5$, —CH$_2$—CCl$_3$, —CH$_2$—CBr$_3$, —CH$_2$—CH$_2$—CN, n-propyl, —CH$_2$—CH$_2$—CH$_2$—OH, —CH$_2$—CH$_2$—CH$_2$—SH, —CH$_2$—CH$_2$—CH$_2$—NH$_2$, —CH$_2$—CH$_2$—CH$_2$—NH—CH$_3$, —CH$_2$—CH$_2$—CH$_2$—N(CH$_3$)$_2$, —CH$_2$—CH$_2$—CH$_2$—N(C$_2$H$_5$)$_2$, —CH$_2$—CH$_2$—CH$_2$—N(CH$_3$)(C$_2$H$_5$), —CH$_2$—CH$_2$—O—CH$_3$, —CF$_2$—CF$_2$—CF$_3$, —CF(CF$_3$)$_2$, isopropyl, —CH$_2$—CH$_2$—CH$_2$—CN, —CH$_2$—O—CH$_2$—CH$_3$, —CH$_2$—CH$_2$—SF$_3$, —CH$_2$—CH$_2$—OCF$_3$, —CH(CH$_3$)(O—CH$_3$), —CH(CH$_3$)(S—CH$_3$), n-butyl, —CF$_2$—CF$_2$—CF$_2$—CF$_3$, —CH$_2$—CH$_2$—CH$_2$—CH$_2$—CN, sec-butyl, isobutyl, tert-butyl, n-pentyl, sec-pentyl, neopentyl, n-hexyl, vinyl, 1-propenyl, 2-propenyl, 1-butenyl, 2-butenyl, 3-butenyl, 2-methylbuten-2-yl, (1,1,2)-trifluoro-1-butenyl, 1-pentenyl, 2-pentenyl, 3-pentenyl, and 4-pentenyl;

and X, m, n, p1, p2, and R$^6$ to R$^{48}$ each have the meanings stated above, in each case optionally in the form of one of the pure stereoisomers thereof, particularly enantiomers or diastereoisomers, the racemates thereof or in the form of a mixture of stereoisomers, particularly the enantiomers and/or diastereoisomers, in an arbitrary mixing ratio, or in each case in the form of corresponding salts, or in each case in the form of corresponding solvates.

Preference is also given to substituted cyclic urea derivatives of the above general formula I, in which R$^1$, R$^2$, R$^4$, and R$^5$ each independently stand for H; F; Cl; I; Br; —NO$_2$; —NH$_2$; —OH; and —SH; —NR$^{13}$R$^{14}$; —NH—R$^{15}$; —OR$^{16}$; —SR$^{17}$; —NR$^{23}$S(=O)$_2$R$^{24}$;

or for a radical selected from the group consisting of methyl, —CF$_3$, ethyl, —CH$_2$—CF$_3$, —C$_2$F$_5$, n-propyl, isopropyl, n-butyl, sec-butyl, isobutyl, tert-butyl, or n-pentyl and R$^3$ stands for F; Cl; Br; I; —OR$^2$; —NR$^{23}$S(=O)$_2$R$^{24}$;

or for a radical selected from the group consisting of —SF$_5$, —CF$_3$, —C$_2$F$_5$, —CH$_2$—CF$_3$, —CF(CF$_3$)$_2$, isopropyl, —CH(CH$_3$)(O—CH$_3$), —CH(CH$_3$)(S—CH$_3$), sec-butyl, isobutyl, and tert-butyl;

and X, m, n, p1, p2, and R$^6$ to R$^{48}$ each have the meanings stated above, in each case optionally in the form of one of the pure stereoisomers thereof, particularly enantiomers or diastereoisomers, the racemates thereof or in the form of a mixture of stereoisomers, particularly the enantiomers and/or diastereoisomers, in an arbitrary mixing ratio, or in each case in the form of corresponding salts, or in each case in the form of corresponding solvates.

Preference is also given to substituted cyclic urea derivatives of the above general formula I, in which R$^8$, R$^9$, R$^{11}$, and R$^{12}$ each independently stand for H; F; Cl; Br; I; —SF$_5$; —NO$_2$; —NH$_2$; —OH; —SH;

—C(=O)—NH$_2$; —S(=O)$_2$—NH$_2$;

—NR$^{13}$R$^{14}$; —NH—R$^{15}$; —OR$^{16}$; —SR$^{17}$; —O—(CH$_2$)$_a$—R$^{18}$; —O—(CH$_2$)$_b$—OR$^{19}$;

—(CH$_2$)$_c$—O—(CH$_2$)$_d$—OR$^{20}$;

—(CH$_2$)$_e$—O—C(=O)—R$^{21}$;

—(CH$_2$)$_f$—O—C(=O)—OR$^{22}$;

—NR$^{23}$S(=O)$_2$R$^{24}$;

—(CH$_2$)$_g$—C(=O)—NR$^{25}$R$^{26}$;

—(CH$_2$)$_h$—C(=O)—NH—R$^{27}$;

—S(=O)$_i$R$^{28}$;

—(CH$_2$)$_j$—S(=O)$_2$—NR$^{29}$R$^{30}$;

—(CH$_2$)$_k$—S(=O)$_2$—NHR$^{31}$;

—(CH$_2$)$_l$—NR$^{32}$—C(=O)(CH$_2$)$_q$—OR$^{33}$;

—(CH$_2$)$_r$—NH—C(=O)(CH$_2$)$_s$—OR$^{34}$;

—(CH$_2$)$_t$—NR$^{35}$—O—C(=O)—OR$^{36}$;

—(CH$_2$)$_u$—NH—O—C(=O)—OR$^{37}$;

—(CH$_2$)$_v$—O—S(=O)$_2$—R$^{38}$;

—(CH$_2$)$_w$—NR$^{39}$—C(=O)—SR$^{40}$;

—(CH$_2$)$_y$—C(=O)—NH—OR$^{41}$;

—P(=O)(OR$^{42}$)$_2$;

—(CH$_2$)$_z$—C(=S)—NR$^{43}$R$^{44}$;

(CH$_2$)$_{aa}$—C(=S)—NH—R$^{45}$;

—(CH$_2$)$_{bb}$—NR$^{46}$—C(=O)—R$^{47}$;

—(CH$_2$)$_{cc}$—NH—C(=O)—R$^{48}$;

oder —NH—C(=NH)—NH$_2$;

with a, b, and c, d, q, and s each being independently equal to 1, 2, 3, 4, or 5, e, f, and g, h, j, k, l, r, t, u, v, w, x, y, and z, aa, bb and cc, each being independently equal to 0, 1, 2, 3, 4, or 5, and i being equal to 1 or 2;

or for a radical selected from the group consisting of methyl, —CF$_3$, —CCl$_3$, —CBr$_3$, —CH$_2$—CN, —CH$_2$—O—CH$_3$, —CH$_2$—O—CF$_3$, —CH$_2$—SF$_3$, —CH$_2$—NH$_2$, —CH$_2$—OH, —CH$_2$—SH, —CH$_2$—NH—CH$_3$, —CH$_2$—N(CH$_3$)$_2$, —CH$_2$—N(C$_2$H$_5$)$_2$, —CH$_2$—N(CH$_3$)(C$_2$H$_5$), ethyl, —CH$_2$—CH$_2$—NH$_2$, —CH$_2$—CH$_2$—OH, —CH$_2$—CH$_2$—SH, —CH$_2$—CH$_2$—NH—CH$_3$, —CH$_2$—CH$_2$—N(CH$_3$)$_2$, —CH$_2$—CH$_2$—N(C$_2$H$_5$)$_2$, —CH$_2$—CH$_2$—N(CH$_3$)(C$_2$H$_5$), —CH$_2$—CF$_3$, —C$_2$F$_5$, —CH$_2$—CCl$_3$, —CH$_2$—CBr$_3$, —CH$_2$—CH$_2$—CN, n-propyl, —CH$_2$—CH$_2$—CH$_2$—OH, —CH$_2$—CH$_2$—CH$_2$—SH, —CH$_2$—CH$_2$—CH$_2$—NH$_2$, —CH$_2$—CH$_2$—CH$_2$—NH—CH$_3$, —CH$_2$—CH$_2$—CH$_2$—N(CH$_3$)$_2$, —CH$_2$—CH$_2$—CH$_2$—N(C$_2$H$_5$)$_2$, —CH$_2$—CH$_2$—CH$_2$—N(CH$_3$)(C$_2$H$_5$), —CH$_2$—CH$_2$—O—CH$_3$, —CF$_2$—CF$_2$—CF$_3$, —CF(CF$_3$)$_2$, isopropyl, —CH$_2$—CH$_2$—CH$_2$—CN, —CH$_2$—O—CH$_2$—CH$_3$, —CH$_2$—CH$_2$—SF$_3$, —CH$_2$—CH$_2$—OCF$_3$, —CH(CH$_3$)(O—CH$_3$), —CH(CH$_3$)(S—CH$_3$), n-butyl, —CF$_2$—CF$_2$—CF$_2$—CF$_3$, —CH$_2$—CH$_2$—CH$_2$—CH$_2$—CN, sec-butyl, isobutyl, tert-butyl, n-pentyl, sec-pentyl, neopentyl, n-hexyl, vinyl, 1-propenyl, 2-propenyl, 1-butenyl, 2-butenyl, 3-butenyl, 2-methylbuten-2-yl, (1,1,2)-trifluoro-1-butenyl, 1-pentenyl, 2-pentenyl, 3-pentenyl, and 4-pentenyl;

or for an aryl radical selected from the group consisting of phenyl and naphthyl, wherein the aryl radical can be substituted by 1, 2, 3, 4, or 5 substituents independently selected from the group consisting of F, Cl, Br, I, —CN, —NO$_2$, —OH, —SH, methyl, ethyl, —CF$_3$, —O—CF$_3$, —S—CF$_3$, —SF$_5$, —O—CH$_3$, —O—C$_2$H$_5$, —NH$_2$, —N(CH$_3$)$_2$, —N(C$_2$H$_5$)$_2$, —N(H)(CH$_3$), and —N(H)(C$_2$H$_5$);

and

R$^{10}$ stands for —NR$^{23}$S(=O)$_2$R$^{24}$;

and X, m, n, p1, and p2, R$^1$ to R$^7$ and R$^{13}$ to R$^{48}$ each have the aforementioned meanings, in each case optionally in the form of one of the pure stereoisomers thereof, particularly enantiomers or diastereoisomers, the racemates thereof or in the form of a mixture of stereoisomers, particularly the enantiomers and/or diastereoisomers, in an arbitrary mixing ratio, or in each case in the form of corresponding salts, or in each case in the form of corresponding solvates.

Preference is also given to substituted cyclic urea derivatives of the above general formula I, in which R$^8$, R$^9$, R$^{11}$, and R$^{12}$ each independently stand for H; F; Cl; Br; I; —NO$_2$; —NH$_2$; —OH; —SH; —NR$^{13}$R$^{14}$; —NH—R$^{15}$; —OR$^{16}$; —SR$^{17}$; or —NR$^{23}$S(=O)$_2$R$^{24}$;

or for a radical selected from the group consisting of methyl, —CF$_3$, ethyl, —CH$_2$—CF$_3$, —C$_2$F$_5$, n-propyl, isopropyl, n-butyl, sec-butyl, isobutyl, tert-butyl, or n-pentyl and R$^{10}$ stands for —NR$^{23}$S(=O)$_2$R$^{24}$;

and X, m, n, p1, and p2, R$^1$ to R$^7$ and R$^{13}$ to R$^{48}$ each have the meanings stated above, in each case optionally in the form of one of the pure stereoisomers thereof, particularly enantiomers or diastereoisomers, the racemates thereof or in the form of a mixture of stereoisomers, particularly the enantiomers and/or diastereoisomers, in an arbitrary mixing ratio, or in each case in the form of corresponding salts, or in each case in the form of corresponding solvates.

Preference is also given to substituted cyclic urea derivatives of the above general formula I, in which the radical R$^{10}$ stands for —NR$^{23}$S(=O)$_2$R$^{24}$ and the radicals R$^8$, R$^9$, R$^{11}$, and R$^{12}$ in each case stand for H;

and X, m, n, p1, and p2, R$^1$ to R$^7$ and R$^{13}$ to R$^{48}$ each have the meanings stated above, in each case optionally in the form of one of the pure stereoisomers thereof, particularly enantiomers or diastereoisomers, the racemates thereof or in the form of a mixture of stereoisomers, particularly the enantiomers and/or diastereoisomers, in an arbitrary mixing ratio, or in each case in the form of corresponding salts, or in each case in the form of corresponding solvates.

Preference is also given to substituted cyclic urea derivatives of the above general formula I, in which the radical R$^3$ stands for —OR$^{16}$; —NR$^{23}$S(=O)$_2$R$^{24}$; or for a radical selected from the group consisting of isopropyl, sec-butyl, isobutyl, and tert-butyl; and the radicals R$^1$, R$^2$, R$^4$, and R$^5$ in each case stand for H;

and X, m, n, p1, p2, R$^5$ bis R$^{48}$ each have the meanings stated above, in each case optionally in the form of one of the pure stereoisomers thereof, particularly enantiomers or diastereoisomers, the racemates thereof or in the form of a mixture of stereoisomers, particularly the enantiomers and/or diastereoisomers, in an arbitrary mixing ratio, or in each case in the form of corresponding salts, or in each case in the form of corresponding solvates.

Preference is also given to substituted cyclic urea derivatives of the above general formula I, in which R$^{13}$, R$^{14}$, R$^{15}$, R$^{16}$, R$^{17}$, R$^{19}$, R$^{20}$, R$^{21}$, R$^{22}$, R$^{25}$, R$^{26}$, R$^{27}$, R$^{28}$, R$^{29}$, R$^{30}$, R$^{31}$, R$^{32}$, R$^{33}$, R$^{34}$, R$^{35}$, R$^{36}$, R$^{37}$, R$^{38}$, R$^{39}$, R$^{40}$, R$^{41}$, R$^{42}$, R$^{43}$, R$^{44}$, R$^{45}$, R$^{46}$, R$^{47}$, and R$^{48}$ independently stand for a radical selected from the group consisting of methyl, —CF$_3$, —CCl$_3$, —CBr$_3$, —CH$_2$—CN, —CH$_2$—O—CH$_3$, —CH$_2$—O—CF$_3$, —CH$_2$—SF$_3$, —CH$_2$—NH$_2$, —CH$_2$—OH, —CH$_2$—SH, —CH$_2$—NH—CH$_3$, —CH$_2$—N(CH$_3$)$_2$, —CH$_2$—N(C$_2$H$_5$)$_2$, —CH$_2$—N(CH$_3$)(C$_2$H$_5$), ethyl, —CH$_2$—CH$_2$—NH$_2$, —CH$_2$—CH$_2$—OH, —CH$_2$—CH$_2$—SH, —CH$_2$—CH$_2$—NH—CH$_3$, —CH$_2$—CH$_2$—N(CH$_3$)$_2$, —CH$_2$—CH$_2$—N(C$_2$H$_5$)$_2$, —CH$_2$—CH$_2$—N(CH$_3$)(C$_2$H$_5$), —CH$_2$—CF$_3$, —C$_2$F$_5$, —CH$_2$—CCl$_3$, —CH$_2$—CBr$_3$, —CH$_2$—CH$_2$—CN, n-propyl, —CH$_2$—CH$_2$—CH$_2$—OH, —CH$_2$—CH$_2$—CH$_2$—SH, —CH$_2$—CH$_2$—CH$_2$—NH$_2$, —CH$_2$—CH$_2$—CH$_2$—NH—CH$_3$, —CH$_2$—CH$_2$—CH$_2$—N(CH$_3$)$_2$, —CH$_2$—CH$_2$—CH$_2$—N(C$_2$H$_5$)$_2$, —CH$_2$—CH$_2$—CH$_2$—N(CH$_3$)(C$_2$H$_5$), —CH$_2$—CH$_2$—O—CH$_3$, —CF$_2$—CF$_2$—CF$_3$, —CF(CF$_3$)$_2$, isopropyl, —CH$_2$—CH$_2$—CH$_2$—CN, —CH$_2$—O—CH$_2$—CH$_3$, —CH$_2$—CH$_2$—SF$_3$, —CH$_2$—CH$_2$—OCF$_3$, —CH(CH$_3$)(O—CH$_3$), —CH(CH$_3$)(S—CH$_3$), n-butyl, —CF$_2$—CF$_2$—CF$_2$—CF$_3$, —CH$_2$—CH$_2$—CH$_2$—CH$_2$—CN, sec-butyl, isobutyl, tert-butyl, n-pentyl, sec-pentyl, neopentyl, n-hexyl, vinyl, 1-propenyl, 2-propenyl, 1-butenyl, 2-butenyl, 3-butenyl, 2-methylbuten-2-yl, (1,1,2)-trifluoro-1-butenyl, 1-pentenyl, 2-pentenyl, 3-pentenyl, and 4-pentenyl;

or for a (hetero)cycloaliphatic radical selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl, and dithiolanyl, wherein the (hetero)cycloaliphatic radical can in each case be optionally substituted by 1, 2, 3, 4, or 5 substituents independently selected from the group consisting of thioxo (=S), F, Cl, Br, I, —CN, —CF$_3$, —SF$_5$, —OH, —NH$_2$, —O—CF$_3$, —SH, —O—CH$_3$, —O—C$_2$H$_5$, methyl, ethyl, n-propyl, isopropyl, n-butyl, sec-butyl, isobutyl, tert-butyl, —S—CH$_3$, —S—C$_2$H$_5$, —C(=O)—O—CH$_3$, —C(=O)—O—C$_2$H$_5$, Oxo (=O), —N(CH$_3$)$_2$, —N(C$_2$H$_5$)$_2$, —N(H)(CH$_3$), —N(H)(C$_2$H$_5$), —NO$_2$, —SCF$_3$, —C(=O)—OH, —O-phenyl, —O-benzyl, phenyl, and benzyl, or for a radical selected from the group consisting of phenyl, naphthyl, (1,3)-benzodioxolyl, (1,4)-benzodioxanyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinoxalinyl, quinolinyl, and isoquinolinyl, wherein the radical can in each case be optionally substituted by 1, 2, 3, 4, or 5 substituents independently selected from the group consisting of F, Cl, Br, I, —CN, —NO$_2$, —OH, —SH, methyl, ethyl, n-propyl, isopropyl, n-butyl, sec-butyl, isobutyl, tert-butyl, —CF$_3$, —O—CF$_3$, —S—CF$_3$, —SF$_5$, —O—CH$_3$, —O—C$_2$H$_5$, —O-phenyl, —O-benzyl, —NH$_2$, —N(CH$_3$)$_2$, —N(C$_2$H$_5$)$_2$, —N(H)(CH$_3$) and —N(H)(C$_2$H$_5$);

and X, m, n, p1, p2, R$^1$ bis R$^{12}$, R$^{18}$, R$^{23}$ and R$^{24}$ each have the meanings stated above, in each case optionally in the form of one of the pure stereoisomers thereof, particularly enantiomers or diastereoisomers, the racemates thereof or in the form of a mixture of stereoisomers, particularly the enantiomers and/or diastereoisomers, in an arbitrary mixing ratio, or in each case in the form of corresponding salts, or in each case in the form of corresponding solvates.

Preference is also given to substituted cyclic urea derivatives of the above general formula I, in which $R^{18}$ stands for a (hetero)cycloaliphatic radical selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl, and dithiolanyl, wherein the (hetero)cycloaliphatic radical can in each case be optionally substituted by 1, 2, 3, 4, or 5 substituents independently selected from the group consisting of thioxo (=S), F, Cl, Br, I, —CN, —$CF_3$, —$SF_5$, —OH, —$NH_2$, —O—$CF_3$, —SH, —O—$CH_2$, —O—$C_2H_5$, methyl, ethyl, n-propyl, isopropyl, n-butyl, sec-butyl, isobutyl, tert-butyl, —S—$CH_3$, —S—$C_2H_5$, —C(=O)—O—$CH_3$, —C(=O)—O—$C_2H_5$, Oxo (=O), —N($CH_3$)$_2$, —N($C_2H_5$)$_2$, —N(H)($CH_3$), —N(H)($C_2H_5$), —$NO_2$, —$SCF_3$, —C(=O)—OH, —O-phenyl, —O-benzyl, phenyl, and benzyl, or for a radical selected from the group consisting of phenyl, naphthyl, (1,3)-benzodioxolyl, (1,4)-benzodioxanyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinolinyl, quinoxalinyl, and isoquinolinyl, wherein the radical can in each case be optionally substituted by 1, 2, 3, 4, or 5 substituents independently selected from the group consisting of F, Cl, Br, I, —CN, —$NO_2$, —OH, —SH, methyl, ethyl, n-propyl, isopropyl, n-butyl, sec-butyl, isobutyl, tert-butyl, —$CF_3$, —O—$CF_3$, —S—$CF_3$, —$SF_5$, —O—$CH_3$, —O—$C_2H_5$, —O-phenyl, —O-benzyl, —$NH_2$, —N($CH_3$)$_2$, —N($C_2H_5$)$_2$, —N(H)($CH_3$) and —N(H)($C_2H_5$);

and X, m, n, p1, and p2, $R^1$ bis $R^{17}$ and $R^{19}$ bis $R^{48}$ each have the meanings stated above, in each case optionally in the form of one of the pure stereoisomers thereof, particularly enantiomers or diastereoisomers, the racemates thereof or in the form of a mixture of stereoisomers, particularly the enantiomers and/or diastereoisomers, in an arbitrary mixing ratio, or in each case in the form of corresponding salts, or in each case in the form of corresponding solvates.

Preference is also given to substituted cyclic urea derivatives of the above general formula I, in which
$R^{23}$ stands for a hydrogen radical
or for a radical selected from the group consisting of methyl, ethyl, n-propyl, isopropyl, n-butyl, sec-butyl, isobutyl, tert-butyl, n-pentyl, sec-pentyl, neopentyl, and n-hexyl;
and X, m, n, p1, and p2, $R^1$ to $R^{22}$ and $R^{24}$ to $R^{48}$ each have the meanings stated above, in each case optionally in the form of one of the pure stereoisomers thereof, particularly enantiomers or diastereoisomers, the racemates thereof or in the form of a mixture of stereoisomers, particularly the enantiomers and/or diastereoisomers, in an arbitrary mixing ratio, or in each case in the form of corresponding salts, or in each case in the form of corresponding solvates.

Preference is also given to substituted cyclic urea derivatives of the above general formula I, in which
$R^{24}$ stands for a radical selected from the group consisting of methyl, —$CH_2$—CN, ethyl, —$CH_2$—$CH_2$—CN, n-propyl, isopropyl, n-butyl, sec-butyl, isobutyl, tert-butyl, n-pentyl, sec-pentyl, neopentyl, and n-hexyl;
and X, m, n, p1, and p2, $R^1$ to $R^{23}$ and $R^{25}$ to $R^{48}$ each have the meanings stated above, in each case optionally in the form of one of the pure stereoisomers thereof, particularly enantiomers or diastereoisomers, the racemates thereof or in the form of a mixture of stereoisomers, particularly the enantiomers and/or diastereoisomers, in an arbitrary mixing ratio, or in each case in the form of corresponding salts, or in each case in the form of corresponding solvates.

Preference is also given to substituted cyclic urea derivatives of the above general formula I, in which
p1 and p2 each independently
stand for 0 or 1, the sum of p1 and p2 being 0 or 1;
and X, m, n, and $R^1$ bis $R^{48}$ each have the meanings stated above, in each case optionally in the form of one of the pure stereoisomers thereof, particularly enantiomers or diastereoisomers, the racemates thereof or in the form of a mixture of stereoisomers, particularly the enantiomers and/or diastereoisomers, in an arbitrary mixing ratio, or in each case in the form of corresponding salts, or in each case in the form of corresponding solvates.

It will be clear to the person skilled in the art that the situation in which p1 and p2 are each equal to 0 will result in a compound of the general formula Ic:

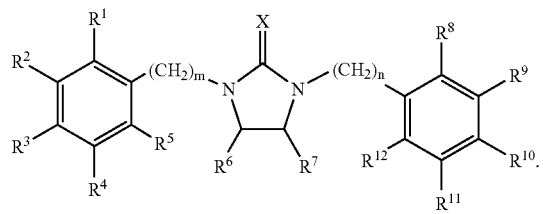

It will likewise be clear to the person skilled in the art that the situation in which p1 is equal to 0 and p2 is equal to 1 will result in the general formula Id:

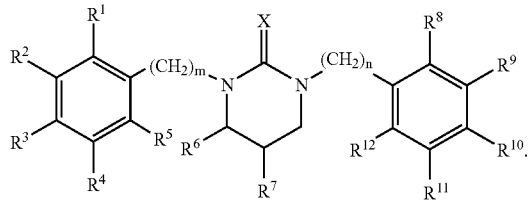

It will also be clear to the person skilled in the art that the situation in which p1 is equal to 1 and p2 is equal to 0 will result in a compound of the general formula Ie:

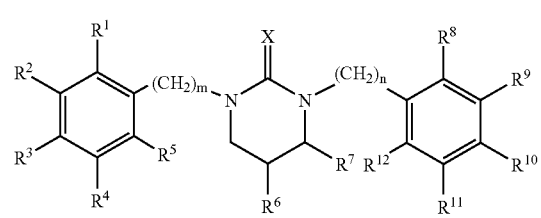

It will likewise be clear to the person skilled in the art that the situation in which $R^6$ and $R^7$ together with the interconnecting C—C bridge form an unsubstituted phenylene radical will result in a compound of the general formula If:

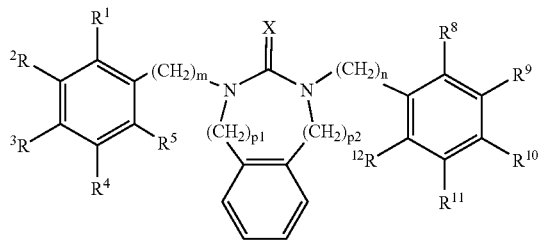

Special preference is given to substituted cyclic urea derivatives of the above general formula I in which X stands for O, S or N—C≡N;
m is equal to 1;
n is equal to 1;
p1 and p2 each independently
  stand for 0 or 1, the sum of p1 and p2 being 0 or 1;
$R^1$, $R^2$, $R^4$, $R^5$, $R^8$, $R^9$, $R^{11}$, and $R^{12}$ each independently
  stand for H; F; Cl; I; Br; —$NO_2$; —$NH_2$; —OH; —SH; —$NR^{13}R^{14}$; —NH—$R^{15}$; —$OR^{16}$; —$SR^{17}$; or —$NR^{23}S(═O)_2R^{24}$;
  or for a radical selected from the group consisting of methyl, —$CF_3$, ethyl, —$CH_2$—$CF_3$, —$C_2F_5$, n-propyl, isopropyl, n-butyl, sec-butyl, isobutyl, tert-butyl, or n-pentyl;
$R^3$ stands for F; Cl; Br; I; —O—$R^{16}$; —$NR^{23}S(═O)_2R^{24}$;
  or for a radical selected from the group consisting of —$SF_5$, —$CF_3$, —$C_2F_5$, —$CH_2$—$CF_3$, —$CF(CF_3)_2$, isopropyl, —$CH(CH_3)(O$—$CH_3)$, —$CH(CH_3)(S$—$CH_3)$, sec-butyl, isobutyl, and tert-butyl;
$R^6$ and $R^7$ each stand for a hydrogen radical
or
$R^6$ and $R^7$, together with the interconnecting C—C bridge, form an unsubstituted phenylene radical;
$R^{10}$ stands for —$NR^{23}S(═O)_2R^{24}$;
$R^{13}$, $R^{14}$, $R^{15}$, $R^{16}$, and $R^{17}$ each independently
  stand for a radical selected from the group consisting of —$CF_3$, —$C_2F_5$, —$CH_2$—$CF_3$, methyl, ethyl, n-propyl, isopropyl, n-butyl, sec-butyl, isobutyl, tert-butyl, n-pentyl, sec-pentyl, neopentyl, and n-hexyl;
  or for a radical selected from the group consisting of phenyl, thiophenyl, furanyl, and pyridinyl, wherein the radical can in each case be optionally substituted by 1, 2, 3, 4, or 5 substituents independently selected from the group consisting of F, Cl, Br, I, —CN, —$NO_2$, —OH, —SH, methyl, ethyl, n-propyl, isopropyl, n-butyl, sec-butyl, isobutyl, tert-butyl, —$CF_3$, —O—$CF_3$, —S—$CF_3$, —$SF_5$, —O—$CH_3$, and —O—$C_2H_5$;
$R^{23}$ stands for a hydrogen radical
and
$R^{24}$ stands for a radical selected from the group consisting of methyl, —$CH_2$—CN, ethyl, —$CH_2$—$CH_2$—CN, n-propyl, isopropyl, n-butyl, sec-butyl, isobutyl, tert-butyl, n-pentyl, sec-pentyl, neopentyl, and n-hexyl;
in each case optionally in the form of one of the pure stereoisomers thereof, particularly enantiomers or diastereoisomers, or the racemates thereof or in the form of a mixture of stereoisomers, particularly the enantiomers and/or diastereoisomers, in an arbitrary mixing ratio, or in each case in the form of corresponding salts, or in each case in the form of corresponding solvates.

Likewise, special preference is given to substituted cyclic urea derivatives of the above general formula I, in which X stands for O, S or N—C≡N;
m is equal to 1;
n is equal to 1;
p1 and p2 each independently
  stand for 0 or 1, the sum of p1 and p2 being 0 or 1;
$R^1$, $R^2$, $R^4$, $R^8$, $R^{11}$, and $R^{12}$ each stand for H;
$R^3$ stands for F; Cl; Br, I; —$OR^{16}$; —$NR^{23}S(═O)_2R^{24}$;
  or for a radical selected from the group consisting of —$CF_3$, —$C_2F_5$, —$CH_2$—$CF_3$, isopropyl, sec-butyl, isobutyl, and tert-butyl;
$R^5$ stands for H; F; Cl; Br or I;
$R^6$ and $R^7$ each stand for a hydrogen radical
or
$R^6$ and $R^7$, together with the interconnecting C—C bridge, form an unsubstituted phenylene radical;
$R^9$ stands for H; F; Cl; Br; I or for a radical selected from the group consisting of methyl, ethyl, n-propyl, isopropyl, n-butyl, isobutyl, and tert-butyl;
$R^{10}$ stands for —$NR^{23}S(═O)_2R^{24}$;
$R^{16}$ stands for a radical selected from the group consisting of —$CF_3$, —$C_2F_5$, and —$CH_2$—$CF_3$;
$R^{23}$ stands for a hydrogen radical
and
$R^{24}$ stands for a radical selected from the group consisting of methyl, ethyl, n-propyl, isopropyl, n-butyl, sec-butyl, isobutyl, tert-butyl, n-pentyl, sec-pentyl, neopentyl, and n-hexyl;
in each case optionally in the form of one of the pure stereoisomers thereof, particularly enantiomers or diastereoisomers, or the racemates thereof or in the form of a mixture of stereoisomers, particularly the enantiomers and/or diastereoisomers, in an arbitrary mixing ratio, or in each case in the form of corresponding salts, or in each case in the form of corresponding solvates.

Very special preference is given to substituted cyclic urea derivatives of the above general formula I, in which X stands for O, S or N—C≡N;
m is equal to 1;
n is equal to 1;
p1 and p2 each independently
  stand for 0 or 1, the sum of p1 and p2 being 0 or 1;
$R^1$, $R^2$, $R^4$, $R^5$, $R^8$, $R^9$, $R^{11}$, and $R^{12}$ in each case stand for H;
$R^3$ stands for —$OR^{16}$; —$NR^{23}S(═O)_2R^{24}$;
  or for a radical selected from the group consisting of —$CF_3$, isopropyl, sec-butyl, isobutyl, and tert-butyl;
$R^6$ and $R^7$ each stand for a hydrogen radical
or
$R^6$ and $R^7$, together with the interconnecting C—C bridge, form an unsubstituted phenylene radical;
$R^{10}$ stands for —$NR^{23}S(═O)_2R^{24}$;
$R^{16}$ stands for a radical selected from the group consisting of —$CF_3$, —$C_2F_5$, and —$CH_2$—$CF_3$;
$R^{23}$ stands for a hydrogen radical
and
$R^{24}$ stands for a radical selected from the group consisting of methyl, ethyl, n-propyl, isopropyl, n-butyl, sec-butyl, isobutyl, tert-butyl, n-pentyl, sec-pentyl, neopentyl, and n-hexyl;
in each case optionally in the form of one of the pure stereoisomers thereof, particularly enantiomers or diastereoisomers, or the racemates thereof or in the form of a mixture of stereoisomers, particularly the enantiomers and/or diastereoisomers, in an arbitrary mixing ratio, or in each case in the form of corresponding salts, or in each case in the form of corresponding solvates.

Even more preference is given to substituted cyclic urea derivatives of the above general formula I selected from the group consisting of

[1] N-[4-[3-(4-tert-butylbenzyl)-2-thioxo-imidazolidinylmethyl]phenyl]methanesulfonamide,
[2] N-[4-[3-(4-tert-butylbenzyl)-2-thioxo-2,3-dihydrobenzoimidazol-1-ylmethyl]phenyl]methanesulfonamide,
[3] N-[4-[3-(4-tert-butylbenzyl)-2-thioxotetrahydropyrimidin-1-ylmethyl]phenyl]methanesulfonamide,
[4] N-[4-[3-(4-tert-butylbenzyl)-2-oxo-imidazolidin-1-ylmethyl]phenyl]methanesulfonamide,
[5] N-[4-[3-(4-tert-butyl benzyl)-2-oxotetrahydropyrimidin-1-ylmethyl]phenyl]methanesulfonamide,
[6] N-[4-[3-(4-tert-butylbenzyl)-2-oxo-2,3-dihydrobenzoimidazol-1-ylmethyl]phenyl]methanesulfonamide,
[7] N-[4-[3-(4-trifluoromethoxybenzyl)-2-oxo-2,3-dihydrobenzimidazol-1-ylmethyl]phenyl]methanesulfonamide,
[8] N-[4-[3-(4-trifluoromethoxybenzyl)-2-thioxo-2,3-dihydrobenzimidazol-1-ylmethyl]phenyl]methanesulfonamide,
[9] N-[4-[3-(4-methanesulfonylaminobenzyl)-2-oxo-2,3-dihydrobenzimidazol-1-ylmethyl]phenyl]methanesulfonamide, and
[10] N-{4-[2-oxo-3-(4-trifluoromethylbenzyl)-2,3-dihydrobenzimidazol-1-ylmethyl] phenyl}methanesulfonamide;
in each case optionally in the form of corresponding salts, or in the form of corresponding solvates.

The invention further relates to a process for the preparation of compounds of the above general formula I, according to which at least one compound of the general formula II,

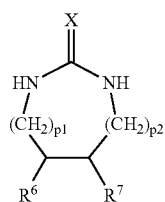

II in which $R^6$, $R^7$, X, p1, and p2 have the meanings stated above, in a reaction medium, preferably in a reaction medium selected from the group consisting of diethyl ether, tetrahydrofuran, dichloromethane, dimethylformamide, acetonitrile, pyridine, dimethyl sulfoxide, toluene and appropriate mixtures, optionally in the presence of at least one base, preferably in the presence of at least one metal hydride salt, more preferably in the presence of potassium and/or sodium hydride, or in the presence of at least one alkali metal carbonate salt, preferably in the presence of potassium and/or sodium carbonate, and at least one alkali metal iodide, preferably potassium and/or sodium iodide, is caused to react with at least one compound of the general formula III,

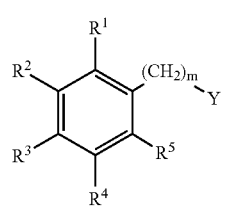

III in which $R^1$ to $R^5$ and m have the meanings stated above and Y stands for a leaving group, preferably for a halogen radical, more preferably for a bromium atom or chlorine atom, to produce at least one compound of the general formula IV,

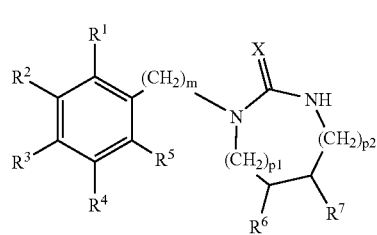

IV in which $R^1$ to $R^7$, X, p1, p2 and m have the meanings stated above, and this is optionally purified and/or isolated, or at least one compound of the general formula V,

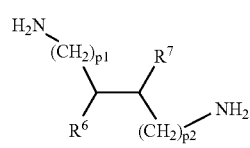

V in which $R^6$, $R^7$, p1, and p2 have the meanings stated above, in a reaction medium, preferably in a reaction medium selected from the group consisting of diethyl ether, tetrahydrofuran, acetonitrile, methanol, ethanol, dimethylformamide, dichloromethane and appropriate mixtures, optionally in the presence of at least one base, preferably in the presence of at least one base selected from the group consisting of pyridine, triethylamine, and diisopropylethylamine, is caused to react with at least one compound of the general formula III to form at least one compound of the general formula VI,

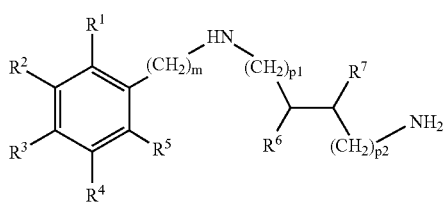

VI in which $R^1$ bis $R^7$, m, p1, and p2 have the meanings stated above, and this is optionally purified and/or isolated, and at least one compound of the general formula VI is caused to react, in a reaction medium, preferably in a reaction medium selected from the group consisting of diethyl ether, tetrahydrofuran, acetonitrile, methanol, ethanol, dimethylformamide, dichloromethane and appropriate mixtures, optionally in the presence of at least one base, preferably in the presence of at least one base selected from the group consisting of pyridine, triethylamine, and diisopropylethylamine, with at least one compound of the general formula Z—C(=X)—Z in which X stands for an oxygen atom or sulfur atom and Z in each case for a leaving group, preferably in each case for a halogen radical, more preferably in each case for a chlorine atom, to form at least one compound of the general formula IV and this is optionally purified and/or isolated, or
at least one compound of the general formula VII,

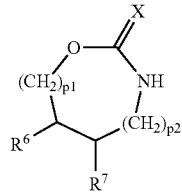

VII in which $R^6$, $R^7$, X, p1, and p2 have the meanings stated above, is caused to react, in a reaction medium, preferably in a reaction medium selected from the group consisting of diethyl ether, tetrahydrofuran, acetonitrile, methanol, ethanol, dimethylformamide, dichloromethane and appropriate mixtures, with at least one compound of the general formula VIII,

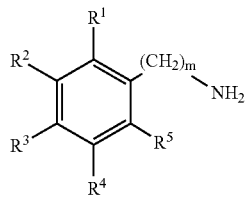

VIII in which $R^1$ to $R^5$ and m have the meanings stated above, to produce at least one compound of the general formula IV, and this is optionally purified and/or isolated,
and at least one compound of the general formula IV is caused to react, in a reaction medium, preferably in a reaction medium selected from the group consisting of diethyl ether, tetrahydrofuran, dichloromethane, dimethylformamide, acetonitrile, pyridine, dimethyl sulfoxide, toluene and corresponding mixtures, in the presence of at least one base, preferably in the presence of at least one metal hydride salt, more preferably in the presence of potassium and/or sodium hydride, or in the presence of at least one alkali metal carbonate salt, preferably in the presence of potassium and/or sodium carbonate, and at least one alkali metal iodide, preferably potassium and/or sodium iodide, with at least one compound of the general formula IX,

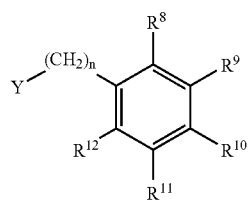

IX in which $R^8$ to $R^{12}$ and n have the meanings stated above, provided that at least one of the substituents $R^8$ to $R^{12}$ stands for an $-N(PG)_2$ group, wherein PG stands in each case for a protective group, preferably for a tert-butoxycarbonyl group or benzyloxycarbonyl group, or $(PG)_2$ together with the interconnecting nitrogen atom form a cyclic protective group, preferably a phthalimide group, and Y stands for a leaving group, preferably for a halogen atom, more preferably for a chlorine or bromine atom, to produce at least one compound of the general formula XI,

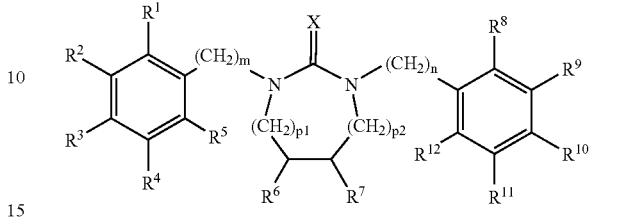

XI in which $R^1$ to $R^{12}$, X, m, n, p1 and p2 have the meanings stated above, provided that at least one of the substituents $R^8$ to $R^{12}$ stands for an $-N(PG)_2$ group, in which PG has the meanings stated above, and this is optionally purified and/or isolated, and at least one compound of the general formula XI is converted, in a reaction medium, preferably in a reaction medium selected from the group consisting of methanol, ethanol, isopropanol, acetone, diethyl ether, tetrahydrofuran, dichloromethane, dimethylformamide, acetonitrile, pyridine, dimethyl sulfoxide, toluene and appropriate mixtures, in the presence of at least one base, preferably in the presence of at least one base selected from the group consisting of dimethylamine, triethylamine, diisopropylethylamine, sodium hydroxide, lithium hydroxide, potassium hydroxide, potassium carbonate, and cesium carbonate, more preferably in the presence of dimethylamine, or in the presence of at least one acid, preferably in the presence of at least one acid selected from the group consisting of hydrochloric acid, acetic acid, trifluoroacetic acid, citric acid, and sulfuric acid, or in the presence of hydrazine and/or phenylhydrazine or in the presence of at least one alkali metal boron hydride, preferably in the presence of sodium tetrahydridoborate, to form at least one compound of the general formula XII,

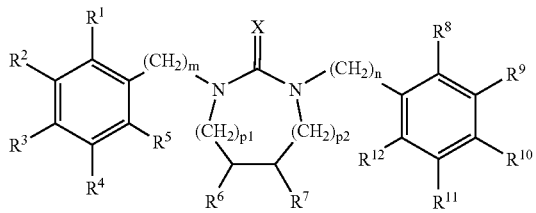

XII in which $R^1$ bis $R^{12}$, X, m, n, p1, and p2 have the meanings stated above, provided that at least one of the substituents $R^8$ to $R^{12}$ stands for an $-NH_2$ group, and this is optionally purified and/or isolated,
or
at least one compound of the general formula IV is caused to react, in a reaction medium, preferably in a reaction medium selected from the group consisting of diethyl ether, tetrahydrofuran, dichloromethane, dimethylformamide, acetonitrile, pyridine, dimethyl sulfoxide, toluene and appropriate mixtures, in the presence of at least one base, preferably in the presence of at least one metal hydride salt, more preferably in the presence of potassium and/or sodium hydride, or in the presence of at least one alkali metal carbonate salt, preferably in the presence of potassium and/or sodium carbonate, and at least one alkali metal iodide, preferably potassium and/or sodium iodide, with at least one compound of the general formula XIII,

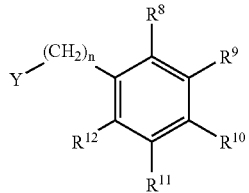

XIII in which $R^8$ to $R^{12}$ and n have the meanings stated above, provided that at least one of the substituents $R^8$ to $R^{12}$ stands for an —$NO_2$ group, and Y stands for a leaving group, preferably for a halogen radical, more preferably for a chlorine radical or bromine atom, to form at least one compound of the general formula XIV,

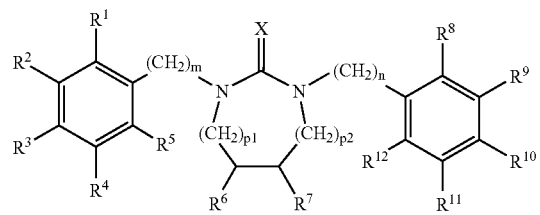

XIV in which $R^1$ bis $R^{12}$, X, m, n, p1, and p2 have the meanings stated above, provided that at least one of the substituents $R^8$ to $R^{12}$ stands for an —$NO_2$ group, and this is optionally purified and/or isolated, and at least one compound of the general formula XIV is converted, in a reaction medium, preferably in a reaction medium selected from the group consisting of methanol, ethanol, isopropanol, acetone, diethyl ether, tetrahydrofuran, dichloromethane, dimethylformamide, acetonitrile, pyridine, dimethyl sulfoxide, toluene and appropriate mixtures, in the presence of hydrogen and in the presence of a catalyst, preferably in the presence of a catalyst based on palladium and/or platinum, more preferably in the presence of palladium, to produce at least one compound of the general formula XII, in which $R^1$ bis $R^{12}$, X, m, n, p1, and p2 have the meanings stated above, provided that at least one of the substituents $R^8$ to $R^{12}$ stands for an —$NH_2$ group, and this is optionally purified and/or isolated, and at least one compound of the general formula XII is caused to react, in a reaction medium, preferably in a reaction medium selected from the group consisting of acetone, diethyl ether, tetrahydrofuran, dichloromethane, dimethylformamide, acetonitrile, pyridine, dimethyl sulfoxide, toluene and appropriate mixtures, optionally in the presence of at least one base, preferably in the presence of at least one base selected from the group consisting of pyridine, triethylamine, and diisopropylethylamine, with at least one compound of the general formula $R^{24}$—S(═O)$_2$—Z, in which $R^{24}$ has the meanings stated above and Z stands for a leaving group, preferably for a halogen atom, more preferably for a chlorine atom, to form at least one compound of the general formula Ia,

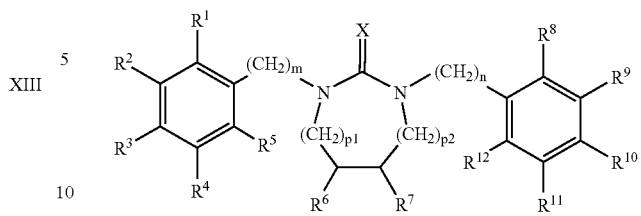

Ia in which $R^1$ bis $R^{12}$, X, m, n, p1, and p2 have the meanings stated above, provided that at least one of the substituents $R^8$ to $R^{12}$ stands for an —NH—S(═O)$_2$—$R^{24}$ group, in which $R^{24}$ has the meanings stated above, and this is optionally purified and/or isolated, or at least one compound of the general formula IV is caused to react, in a reaction medium, preferably in a reaction medium selected from the group consisting of diethyl ether, tetrahydrofuran, dichloromethane, dimethylformamide, acetonitrile, pyridine, dimethyl sulfoxide, toluene and appropriate mixtures, in the presence of at least one base, preferably in the presence of at least one metal hydride salt, more preferably in the presence of potassium and/or sodium hydride, or in the presence of at least one alkali metal carbonate salt, preferably in the presence of potassium and/or sodium carbonate, and at least one alkali metal iodide, preferably potassium and/or sodium iodide, with at least one compound of the general formula XV,

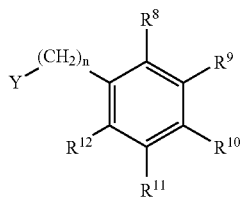

XV in which $R^8$ to $R^{12}$ and n have the meanings stated above, provided that at least one of the substituents $R^8$ to $R^{12}$ stands for an —NH—S(═O)$_2$—$R^{24}$ group, in which $R^{24}$ has the meanings stated above, to produce at least one compound of the general formula Ia, and this is optionally purified and/or isolated, and optionally at least one compound of the general formula Ia is caused to react, in a reaction medium, preferably in a reaction medium selected from the group consisting of diethyl ether, tetrahydrofuran, dichloromethane, dimethylformamide, acetonitrile, pyridine, dimethyl sulfoxide, toluene and appropriate mixtures, optionally in the presence of at least one base, preferably in the presence of at least one metal hydride salt, more preferably in the presence of potassium and/or sodium hydride, or in the presence of at least one alkali metal carbonate salt, preferably in the presence of potassium and/or sodium carbonate, and at least one alkali metal iodide, preferably potassium and/or sodium iodide, with at least one compound of the general formula $R^{23}$—Z, in which $R^{23}$ has the meanings stated above with the exception of hydrogen, and Z stands for a leaving group, preferably for a halogen atom, more preferably for a chlorine atom, to produce at least one compound of the general formula Ib,

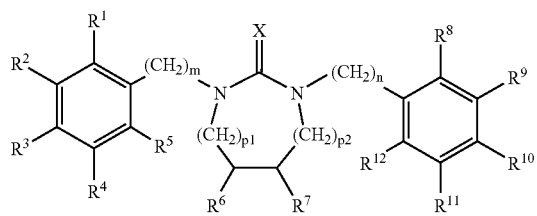

in which $R^1$ bis $R^{12}$, X, m, n, p1, and p2 have the meanings stated above, provided that at least one of the substituents $R^8$ to $R^{12}$ stands for an —$NR^{23}$—$S(=O)_2$—$R^{24}$ group, in which $R^{23}$ and $R^{24}$ have the meanings stated above, and this is optionally purified and/or isolated, and optionally at least one compound of the general formula Ib, in which $R^1$ bis $R^{12}$, m, n, p1, and p2 have the meanings stated above and X stands for an oxygen atom, provided that at least one of the substituents $R^8$ to $R^{12}$ stands for an —$NR^{23}$—$S(=O)_2$—$R^{24}$ group, in which $R^{23}$ and $R^{24}$ have the meanings stated above, is caused to react, in a reaction medium, preferably in a reaction medium selected from the group consisting of toluene, para-xylene, ortho-xylene, meta-xylene, dichloromethane, dimethylformamide, acetonitrile, and appropriate mixtures, with at least one compound of the general formula XVI

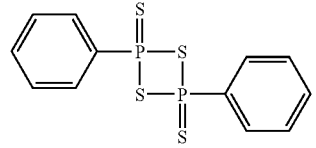

in which the phenyl radicals are each para-substituted by 1 or 2 substituents independently selected from the group consisting of methoxy, phenoxy, Cl, methyl, and Br, preferably by a phenoxy radical or methoxy radical, and more preferably by a methoxy radical, or with phosphorus pentasulfide, to produce at least one compound of the general formula Ib in which $R^1$ to $R^{12}$, m, n and p have the meanings stated above and X stands for or a sulfur atom, provided that at least one of the substituents $R^8$ to $R^{12}$ stands for an —$NR^{23}$—$S(=O)_2$—$R^{24}$ group, in which $R^{23}$ and $R^{24}$ have the meanings stated above, and this is optionally purified and/or isolated.

The invention further relates to a process for the preparation of compounds of the above general formula I, according to which at least one compound of the general formula II,

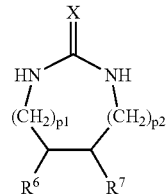

in which $R^6$, $R^7$, X, p1, and p2 have the meanings stated above, is caused to react, in a reaction medium, preferably in a reaction medium selected from the group consisting of diethyl ether, tetrahydrofuran, dichloromethane, dimethylformamide, acetonitrile, pyridine, dimethyl sulfoxide, toluene and corresponding mixtures, in the presence of at least one base, preferably in the presence of at least one metal hydride salt, more preferably in the presence of potassium and/or sodium hydride, or in the presence of at least one alkali metal carbonate salt, preferably in the presence of potassium and/or sodium carbonate, and at least one alkali metal iodide, preferably potassium and/or sodium iodide, with at least one compound of the general formula XVII,

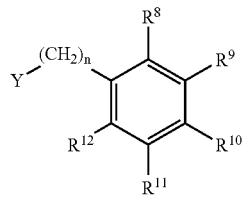

in which $R^8$ to $R^{12}$ and n have the meanings stated above, provided that at least one of the substituents $R^8$ to $R^{12}$ stands for an —$N(PG)_2$ group, wherein PG in each case stands for a protective group, preferably for a tert-butoxycarbonyl group or benzyloxycarbonyl group, or two PG groups together with the interconnecting nitrogen atom form a cyclic protective group, preferably together with the interconnecting nitrogen atom a phthalimide group, or at least one of the substituents $R^8$ to $R^{12}$ stands for an —$NO_2$ group, and Y stands for a leaving group, preferably for a halogen atom, more preferably for a chlorine radical or bromine atom, to produce at least one compound of the general formula XVIII,

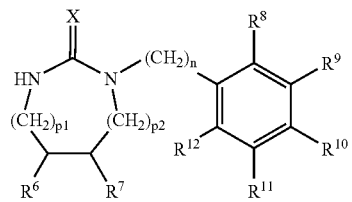

in which $R^6$ to $R^{12}$, p1, p2 and n have the meanings stated above, provided that at least one of the substituents $R^8$ to $R^{12}$ stands for an —$N(PG)_2$ group or an —$NO_2$ group, and this is optionally purified and/or isolated, or at least one compound of the general formula XIX,

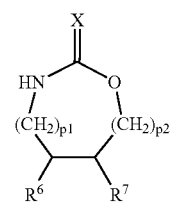

in which $R^6$, $R^7$, X, p1, and p2 have the meanings stated above, is caused to react, in a reaction medium, preferably in a reaction medium selected from the group consisting of diethyl ether, tetrahydrofuran, acetonitrile, methanol, ethanol, dimethylformamide, dichloromethane, and appropriate mixtures, with at least one compound of the general formula XX,

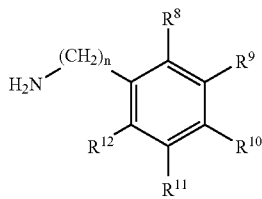

in which $R^8$ to $R^{12}$ and n have the meanings stated above, provided that at least one of the substituents $R^8$ to $R^{12}$ stands for an —$N(PG)_2$ group, in which PG in each case stands for a protective group, preferably for a tert-butoxycarbonyl group or benzyloxycarbonyl group, or $(PG)_2$ together with the interconnecting nitrogen atom form a cyclic protective group, preferably a phthalimide group, or at least one of the substituents $R^8$ to $R^{12}$ stand for an —$NO_2$ group, to produce at least one compound of the general formula XVIII and this is optionally purified and/or isolated,
or at least one compound of the general formula V,

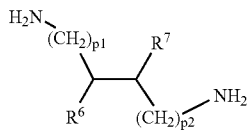

in which $R^6$, $R^7$, p1, and p2 have the meanings stated above, is caused to react, in a reaction medium, preferably in a reaction medium selected from the group consisting of diethyl ether, tetrahydrofuran, acetonitrile, methanol, ethanol, dimethylformamide, dichloromethane and corresponding mixtures, optionally in the presence of at least one base, preferably in the presence of at least one base selected from the group consisting of pyridine, triethylamine, and diisopropylethylamine, with at least one compound of the general formula XVII to produce at least one compound of the general formula XXI,

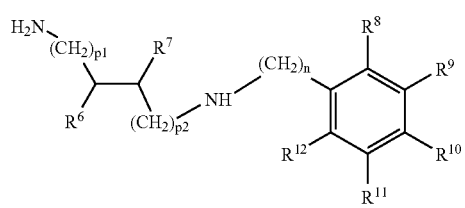

in which $R^6$ to $R^{12}$, p1, p2 and n have the meanings stated above, provided that at least one of the substituents $R^8$ to $R^{12}$ stands for an —$N(PG)_2$ group or an —$NO_2$ group, and this is optionally purified and/or isolated, and at least one compound of the general formula XXI is caused to react, in a reaction medium, preferably in a reaction medium selected from the group consisting of diethyl ether, tetrahydrofuran, acetonitrile, methanol, ethanol, dimethylformamide, dichloromethane, and appropriate mixtures, optionally in the presence of at least one base, preferably in the presence of at least one base selected from the group consisting of pyridine, triethylamine, and diisopropylethylamine, with at least one compound of the general formula Z—C(=X)—Z, in which X stands for an oxygen atom or sulfur atom and Z stands for a leaving group, preferably for a halogen radical, more preferably for a chlorine atom, to produce at least one compound of the general formula XVIII, and this is optionally purified and/or isolated, and at least one compound of the general formula XVIII is caused to react, in a reaction medium, preferably in a reaction medium selected from the group consisting of diethyl ether, tetrahydrofuran, dichloromethane, dimethylformamide, acetonitrile, pyridine, dimethyl sulfoxide, toluene and corresponding mixtures, in the presence of at least one base, preferably in the presence of at least one metal hydride salt, more preferably in the presence of potassium and/or sodium hydride, or in the presence of at least one alkali metal carbonate salt, preferably in the presence of potassium and/or sodium carbonate, and at least one alkali metal iodide, preferably potassium and/or sodium iodide, with at least one compound of the general formula III,

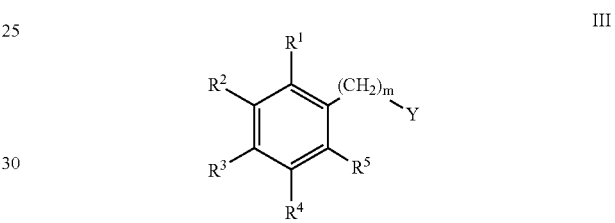

in which $R^1$ to $R^5$ and m have the meanings stated above and Y stands for a leaving group, preferably for a halogen radical, more preferably for a chlorine radical or bromine atom, to produce at least one compound of the general formula XXII,

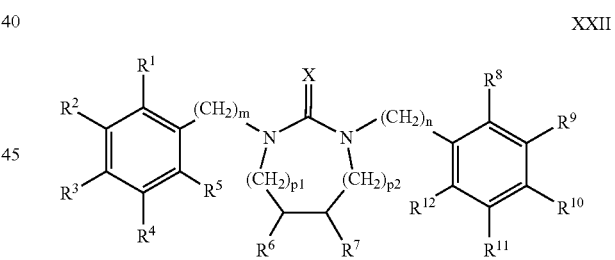

in which $R^1$ bis $R^{12}$, X, m, n, p1, and p2 have the meanings stated above, provided that at least one of the substituents $R^8$ to $R^{12}$ stands for an —$N(PG)_2$ group or —$NO_2$ group, and this is optionally purified and/or isolated and at least one compound of the general formula XXII is caused to react, in a reaction medium, preferably in a reaction medium selected from the group consisting of methanol, ethanol, isopropanol, acetone, diethyl ether, tetrahydrofuran, dichloromethane, dimethylformamide, acetonitrile, pyridine, dimethyl sulfoxide, toluene, and appropriate mixtures, in the presence of at least one base, preferably in the presence of at least one base selected from the group consisting of dimethylamine, triethylamine, diisopropylethylamine, sodium hydroxide, lithium hydroxide, potassium hydroxide, potassium carbonate, and cesium carbonate, more preferably in the presence of dimethylamine, or in the presence of at least one acid, preferably in the presence of at least one acid selected from the group consisting of hydrochloric acid, acetic acid, trifluoroacetic acid, citric acid, and sulfuric acid, or in the presence of hydrazine and/or phenylhydrazine or in the presence of at least one alkali metal boron hydride, preferably in the presence of sodium tetrahydridoborate, or in the presence of hydrogen and a catalyst, preferably a catalyst based on palladium and/or platinum, more preferably palladium, to produce at least one compound of the general formula XII,

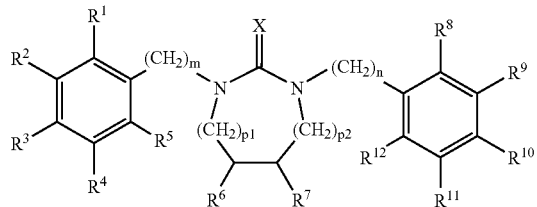

XII in which $R^1$ bis $R^{12}$, X, m, n, p1, and p2 have the meanings stated above, provided that at least one of the substituents $R^8$ to $R^{12}$ stands for an —$NH_2$ group, and this is optionally purified and/or isolated, and at least one compound of the general formula XII is caused to react, in a reaction medium, preferably in a reaction medium selected from the group consisting of acetone, diethyl ether, tetrahydrofuran, dichloromethane, dimethylformamide, acetonitrile, pyridine, dimethyl sulfoxide, toluene, and appropriate mixtures, optionally in the presence of at least one base, preferably in the presence of at least one base selected from the group consisting of pyridine, triethylamine, and diisopropylethylamine, with at least one compound of the general formula $R^{24}$—S($=$O)$_2$—Z, in which $R^{24}$ has the meanings stated above and Z stands for a leaving group, preferably for a halogen atom, more preferably for a chlorine atom, to produce at least one compound of the general formula Ia,

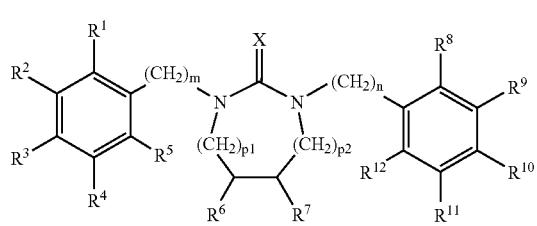

Ia in which $R^1$ bis $R^{12}$, X, m, n, p1, and p2 have the meanings stated above, provided that at least one of the substituents $R^8$ to $R^{12}$ stands for an —NH—S($=$O)$_2$—$R^{24}$ group, in which $R^{24}$ has the meanings stated above, and this is optionally purified and/or isolated, and optionally at least one compound of the general formula Ia is caused to react, in a reaction medium, preferably in a reaction medium selected from the group consisting of diethyl ether, tetrahydrofuran, dichloromethane, dimethylformamide, acetonitrile, pyridine, dimethyl sulfoxide, toluene and corresponding mixtures, optionally in the presence of at least one base, preferably in the presence of at least one metal hydride salt, more preferably in the presence of potassium and/or sodium hydride, or in the presence of at least one alkali metal carbonate salt, preferably in the presence of potassium and/or sodium carbonate, and at least one alkali metal iodide, preferably potassium and/or sodium iodide, with at least one compound of the general formula $R^{23}$—Z in which $R^{23}$ has the meanings stated above with the exception of hydrogen and Z stands for a leaving group, preferably for a halogen atom, more preferably for a chlorine atom, to produce at least one compound of the general formula Ib,

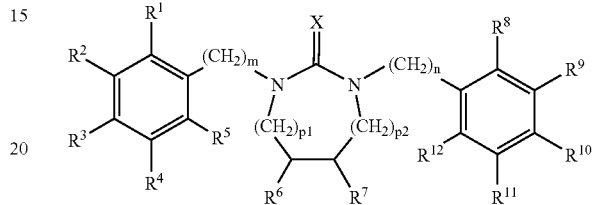

Ib in which $R^1$ bis $R^{12}$, X, m, n, p1, and p2 have the meanings stated above, provided that at least one of the substituents $R^8$ to $R^{12}$ stands for an —$NR^{23}$—S($=$O)$_2$—$R^{24}$ group, in which $R^{23}$ and $R^{24}$ have the meanings stated above, and this is optionally purified and/or isolated, and optionally at least one compound of the general formula Ib in which $R^1$ bis $R^{12}$ m, n, p1, and p2 have the meanings stated above and X stands for an oxygen atom, provided that at least one of the substituents $R^8$ to $R^{12}$ stands for an —$NR^{23}$—S($=$O)$_2$—$R^{24}$ group, in which $R^{23}$ and $R^{24}$ have the meanings stated above, is caused to react, in a reaction medium, preferably in a reaction medium selected from the group consisting of toluene, para-xylene, meta-xylene, ortho-xylene, dichloromethane, dimethylformamide, acetonitrile, and appropriate mixtures, with at least one compound of the general formula XVI,

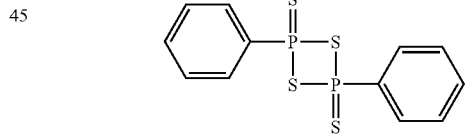

XVI in which the phenyl radicals are each para-substituted by 1 or 2 substituents independently selected from the group consisting of methoxy, phenoxy, Cl, methyl, and Br, preferably by a phenoxy radical or methoxy radical, and more preferably by a methoxy radical, or with phosphorus pentasulfide, to produce at least one compound of the general formula Ib in which $R^1$ to $R^{12}$, m, n and p have the meanings stated above and X stands for a sulfur atom, provided that at least one of the substituents $R^8$ to $R^{12}$ stands for an —$NR^{23}$—S($=$O)$_2$—$R^{24}$ group, in which $R^{23}$ and $R^{24}$ have the meanings stated above, and this is optionally purified and/or isolated.

The present invention further relates to a process for the preparation of compounds of the above general formula I, according to which at least one compound of the general formula II,

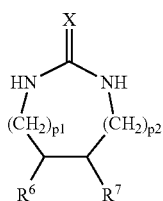

II in which $R^6$, $R^7$, X, p1, and p2 have the meanings stated above, is caused to react, in a reaction medium, preferably in a reaction medium selected from the group consisting of diethyl ether, tetrahydrofuran, dichloromethane, dimethylformamide, acetonitrile, pyridine, dimethyl sulfoxide, toluene, and appropriate mixtures, in the presence of at least one base, preferably in the presence of at least one metal hydride salt, more preferably in the presence of potassium and/or sodium hydride, or in the presence of at least one alkali metal carbonate salt, preferably in the presence of potassium and/or sodium carbonate, and at least one alkali metal iodide, preferably potassium and/or sodium iodide, with at least one compound of the general formula XXIII,

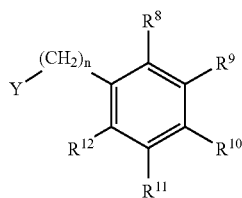

XXIII in which $R^8$ bis $R^{12}$, and n have the meanings stated above, provided that at least one of the substituents $R^8$ to $R^{12}$ stands for an —$NR^{23}$—$S(=O)_2$—$R^{24}$ group and Y stands for a leaving group, preferably for a halogen atom, more preferably for a chlorine radical or bromine atom, to produce at least one compound of the general formula XXIV,

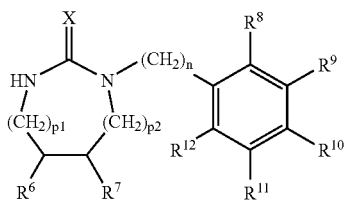

XXIV in which $R^6$ to $R^{12}$, p1, p2 and n the meanings stated above have provided that at least one of the substituents $R^8$ to $R^{12}$ stands for an —$NR^{23}$—$S(=O)_2$—$R^{24}$ group, and this optionally purified and/or isolated,
and at least one compound of the general formula XXIV is caused to react, in a reaction medium, preferably in a reaction medium selected from the group consisting of diethyl ether, tetrahydrofuran, dichloromethane, dimethylformamide, acetonitrile, pyridine, dimethyl sulfoxide, toluene, and appropriate mixtures, in the presence of at least one base, preferably in the presence of at least one metal hydride salt, more preferably in the presence of potassium and/or sodium hydride, or in the presence of at least one alkali metal carbonate salt, preferably in the presence of potassium and/or sodium carbonate, and at least one alkali metal iodide, preferably potassium and/or sodium iodide, with at least one compound of the general formula III,

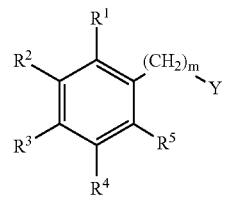

III in which $R^1$ to $R^5$ and m have the meanings stated above and Y stands for a leaving group, preferably for a halogen radical, more preferably for a chlorine or bromine atom, to produce at least one compound of the general formula Ib,

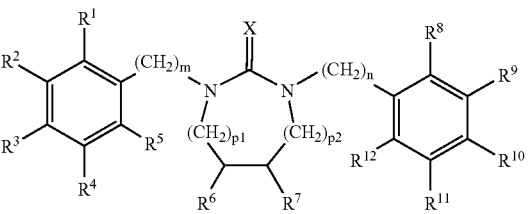

Ib in which $R^1$ bis $R^{12}$, X, m, n, p1, and p2 have the meanings stated above, provided that at least one of the substituents $R^8$ to $R^{12}$ stands for an —$NR^{23}$—$S(=O)_2$—$R^{24}$ group, in which $R^{23}$ and $R^{24}$ have the meanings stated above, and this is optionally purified and/or isolated,
and optionally at least one compound of the general formula Ib in which $R^1$ bis $R^{12}$ m, n, p1, and p2 have the meanings stated above and X stands for an oxygen atom, provided that at least one of the substituents $R^8$ to $R^{12}$ stands for an —$NR^{23}$—$S(=O)_2$—$R^{24}$ group, in which $R^{23}$ and $R^{24}$ have the meanings stated above, is caused to react, in a reaction medium, preferably in a reaction medium selected from the group consisting of toluene, para-xylene, ortho-xylene, meta-xylene, dichloromethane, dimethylformamide, acetonitrile, and appropriate mixtures thereof, with at least one compound of the general formula XVI,

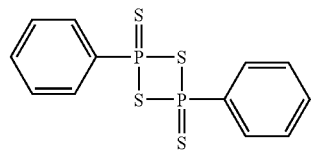

XVI in which the phenyl radicals are each para-substituted by 1 or 2 substituents independently selected from the group consisting of methoxy, phenoxy, Cl, methyl, and Br, preferably by a phenoxy radical or methoxy radical, and more preferably by a methoxy radical, or with phosphorus pentasulfide, to produce at least one compound of the general formula Ib in which $R^1$ to $R^{12}$, m, n, and p have the meanings stated above and X stands for a sulfur atom, provided that at least one of the substituents $R^8$ to $R^{12}$ stands for an —$NR^{23}$—$S(=O)_2$—$R^{24}$ group, in which $R^{23}$ and $R^{24}$ have the meanings stated above, and this is optionally purified and/or isolated.

The compounds of the above formulas II, III, V, VII, IX, XIII, XV, XVI, XVII, XIX, XX and XXIII, and also of the general formulas $R^{23}$—, $R^{24}$—S(=O)$_2$—Z and Z—C(=X)—Z are all commercially available and/or can be prepared by conventional methods known to the person skilled in the art.

The synthesis of compounds of the general formula II, in which X stands for N—C≡N, is also illustrated by the following scheme.

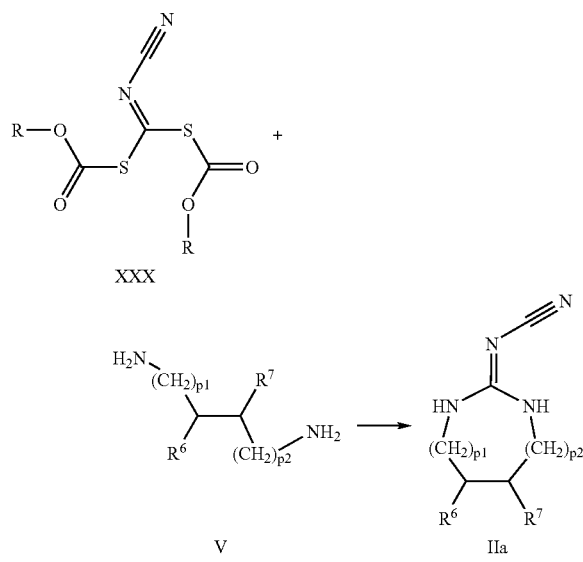

Compounds of the general formula XXX in which R stands for a $C_{1-10}$ alkyl radical and preferably for methyl, ethyl, or tert-butyl, are caused to react with compounds of the general formula V, in which $R^6$, $R^7$, p1, and p2 have the meanings stated above, in a reaction medium, preferably in chloroform at a temperature of from 20° to 50° C. or in n-propanol at a temperature of from 20 to 100° C., to produce compounds of the general formula IIa, in which $R^6$, $R^7$, p1, and p2 have the meanings stated above.

The reactions described above can be carried out in each case under usual conditions well-known to the person skilled in the art, for example, as regards pressure and the order of addition of the components. Optionally, the optimal procedure under the respective conditions can be determined by the person skilled in the art using simple preliminary tests.

The intermediates and end products obtained by the aforementioned reactions can in each case be isolated and/or purified by conventional methods known to the person skilled in the art, if desired and/or necessary. Suitable clean-up techniques are, for example, extraction processes and chromatographic processes such as column chromatography or preparative chromatography.

All of the process steps described above and also the respective purification and/or isolation of intermediates or end-products can be carried out partially or completely under an inert gas atmosphere, preferably under a blanket of nitrogen or argon.

The substituted cyclic urea derivatives of the invention of the aforementioned general formulas I and the corresponding stereoisomers can be isolated either in the form of the free bases thereof or the free acids thereof or in the form of corresponding salts, particularly physiologically acceptable salts.

The free bases of the respective cyclic urea derivatives of the invention of the aforementioned general formulas I and also corresponding stereoisomers can be converted, for example, by reaction with an inorganic or organic acid, preferably with hydrochloric acid, hydrobromic acid, sulfuric acid, phosphoric acid, methanesulfonic acid, p-toluene-sulfonic acid, carbonic acid, formic acid, acetic acid, oxalic acid, succinic acid, tartaric acid, mandelic acid, fumaric acid, lactic acid, citric acid, glutamic acid, or aspartic acid, to form the corresponding salts, preferably physiologically acceptable salts.

The free bases of the respective substituted cyclic urea derivatives of the aforementioned general formulas I and corresponding stereoisomers can likewise be caused to react with the free acid or a salt of a sugar substitute, such as saccharin, cyclamate or acesulfam, to form corresponding physiologically acceptable salts.

Similarly, the free acids of the substituted cyclic urea derivatives of the aforementioned general formulas I and corresponding stereoisomers can be converted to the corresponding physiologically acceptable salts by reaction with a suitable base. Mention may be made, for example, of the alkali-metal salts, alkaline earth metal salts, or ammonium salts $[NH_xR_{4-x}]^+$ in which x is equal to 0, 1, 2, 3, or 4 and R stands for a linear or branched $C_{1-4}$ alkyl radical.

The substituted cyclic urea derivatives of the invention of the aforementioned general formulas I and corresponding stereoisomers can, as well as the corresponding acids and the corresponding bases or salts of these compounds, optionally be obtained by conventional methods known to the person skilled in the art, also in the form of the solvates thereof, preferably in the form of the hydrates thereof.

If the substituted cyclic urea derivatives of the invention of the aforementioned general formulas I are obtained, following preparation thereof, in the form of a mixture of the stereoisomers thereof, preferably in the form of the racemates thereof or other mixtures of the various enantiomers and/or diastereoisomers thereof, these can be separated and optionally isolated by methods known to the person skilled in the art. Mention may be made, for example, of chromatographic separation methods, particularly liquid-chromatographic methods carried out under standard pressure or at elevated pressure, preferably MPLC and HPLC methods, and also methods of fractional crystallization. Particularly individual enantiomers can be separated from each other, eg, diastereoisomeric salts formed by means of HPLC on chiral stationary phase or by means of crystallization with chiral acids, say, (+)-tartaric acid, (−)-tartaric acid, or (+)-10-camphorsulfonic acid.

The substituted cyclic urea derivatives of the invention of the above general formula I and corresponding stereoisomers and also the corresponding acids, bases, salts, and solvates are toxicologically safe and are suitable therefore for use as pharmaceutical active substances in medicinal drugs.

The invention thus further relates to a medicinal drug containing at least one cyclic urea derivative of the invention of the above general formula I, in each case optionally in the form of any one of its pure stereoisomers, particularly enantiomers or diastereoisomers, its racemates or in the form of a mixture of stereoisomers, particularly the enantiomers and/or diastereoisomers, in an arbitrary mixing ratio, or in each case in the form of a corresponding salt, or in each case in the form of a corresponding solvate, and optionally one or more pharmaceutically compatible adjuvants.

These medicinal drugs of the invention are particularly suitable for vanilloid receptor 1-(VR1/TRPV1) regulation, preferably vanilloid receptor 1-(VR1/TRPV1) inhibition and/or vanilloid receptor 1-(VR1/TRPV1) stimulation.

In another preferred embodiment, the medicinal drugs of the invention are suitable for prophylaxis and/or treatment of disorders or diseases that are at least partially mediated by vanilloid receptors 1.

Preferably, the medicinal drug of the invention is suitable for treatment and/or prophylaxis of one or more disorders selected from the group consisting of pain, preferably pain selected from the group consisting of acute pain, chronic pain, neuropathic pain, and visceral pain; arthralgia; migraine; depression; nervous disorders; neurotraumas; neurodegenerative disorders, preferably selected from the group consisting of multiple sclerosis, Morbus Alzheimer, Morbus Parkinson, and Morbus Huntington; cognitive dysfunctions, preferably cognitive deficiency states, more preferably memory defects; epilepsy; respiratory tract diseases, preferably selected from the group consisting of asthma and pneumonia; coughing; urinary incontinence; an overactive bladder (OAB); gastric ulcers; colitis syndrome; apoplectic strokes; eye irritations; cutaneous irritations; neurotic skin conditions; inflammatory diseases, preferably inflammation of the intestine; diarrhoea; pruritus; food intake disorders, preferably selected from the group consisting of bulimia, cachexia, anorexia, and obesity; medicine addiction; medicine abuse; withdrawal phenomena following medicine addiction; tolerance development to pharmaceutical preparations, preferably to natural or synthetic opioids; drug addiction; drug abuse; withdrawal phenomena following drug addiction; alcohol addiction; alcohol abuse and withdrawal phenomena following alcohol addiction; diuresis; antinatriuresis; affection of the cardiovascular system; for vigilance enhancement; for libido enhancement; for modulation of movement activity; for anxiolysis; for local anaesthesia and/or for inhibition of undesirable side effects, preferably selected from the group consisting of hyperthermia, hypertension, and bronchial constriction, caused by the administration of vanilloid receptor 1 (VR1/TRPV1 receptor) agonists, preferably selected from the group consisting of capsaicin, resiniferatoxin, olvanil, arvanil, SDZ-249665, SDZ-249482, nuvanil and capsavanil.

The medicinal drug of the invention is more preferably suitable for treatment and/or prophylaxis of one or more disorders selected from the group consisting of pain, preferably pain selected from the group consisting of acute pain, chronic pain, neuropathic pain, and visceral pain; migraine; depression; neurodegenerative disorders, preferably selected from the group consisting of multiple sclerosis, Morbus Alzheimer, Morbus Parkinson, and Morbus Huntington; cognitive dysfunctions, preferably cognitive deficiency states, more preferably memory defects; urinary incontinence; overactive bladder (OAB); medicine addiction; medicine abuse; withdrawal phenomena following medicine addiction; tolerance development to pharmaceutical preparations, preferably tolerance development to natural or synthetic opioids; drug addiction; drug abuse; withdrawal phenomena following drug addiction; alcohol addiction; alcohol abuse and withdrawal phenomena following alcohol addiction.

The medicinal drug of the invention is most preferably suitable for treatment and/or prophylaxis of pain, preferably pain selected from the group consisting of acute pain, chronic pain, neuropathic pain, and visceral pain, and/or urinary incontinence.

The invention further relates to the use of at least one substituted cyclic urea derivative of the invention of the above general formula I, in each case optionally in the form of one of its pure stereoisomers, particularly enantiomers or diastereoisomers, its racemates or in the form of a mixture of stereoisomers, particularly the enantiomers and/or diastereoisomers, in an arbitrary mixing ratio, or in each case in the form of a corresponding salt, or in each case in the form of a corresponding solvate, and optionally one or more pharmaceutically compatible adjuvants, for the preparation of a medicinal drug for vanilloid receptor 1-(VR1/TRPV1) regulation, preferably for vanilloid receptor 1-(VR1/TRPV1) inhibition and/or for vanilloid receptor 1-(VR1/TRPV1) stimulation.

Preference is given to the use of at least one substituted cyclic urea derivative of the above general formula I, in each case optionally in the form of one of its pure stereoisomers, particularly enantiomers or diastereoisomers, its racemates or in the form of a mixture of stereoisomers, particularly the enantiomers and/or diastereoisomers, in an arbitrary mixing ratio, or in each case in the form of a corresponding salt, or in each case in the form of a corresponding solvate, and also optionally one or more pharmaceutically compatible adjuvants for the preparation of a medicinal drug for the prophylaxis and/or treatment of disorders or diseases at least partially mediated by vanilloid receptors 1.

Particular preference is given to the use of at least one substituted cyclic urea derivative of the above general formula I, in each case optionally in the form of one of its pure stereoisomers, particularly enantiomers or diastereoisomers, its racemates or in the form of a mixture of stereoisomers, particularly the enantiomers and/or diastereoisomers, in an arbitrary mixing ratio, or in each case in the form of a corresponding salt, or in each case in the form of a corresponding solvate, and also optionally one or more pharmaceutically compatible adjuvants, for the preparation of a medicinal drug for treatment and/or prophylaxis of one or more disorders selected from the group consisting of pain, preferably pain selected from the group consisting of acute pain, chronic pain, neuropathic pain, and visceral pain; arthralgia; migraine; depression; nervous disorders; neurotraumas; neurodegenerative disorders, preferably selected from the group consisting of multiple sclerosis, Morbus Alzheimer, Morbus Parkinson, and Morbus Huntington; cognitive dysfunctions, preferably cognitive deficiency states, more preferably memory defects; epilepsy; respiratory tract diseases, preferably selected from the group consisting of asthma and pneumonia; coughing; urinary incontinence; overactive bladder (OAB); gastric ulcers; colitis syndrome; apoplectic strokes; eye irritations; cutaneous irritations; neurotic skin conditions; inflammatory diseases, preferably inflammation of the intestine; diarrhoea; pruritus; food intake disorders, preferably selected from the group consisting of bulimia, cachexia, anorexia, and obesity; medicine addiction; medicine abuse; withdrawal phenomena following medicine addiction; tolerance development to pharmaceutical preparations, preferably to natural or synthetic opioids; drug addiction; drug abuse; withdrawal phenomena following drug addiction; alcohol addiction; alcohol abuse and withdrawal phenomena following alcohol addiction; for diuresis; for antinatriuresis; for affection of the cardiovascular system; for vigilance enhancement; for libido enhancement; for modulation of movement activity; for anxiolysis; for local anaesthesia and/or for inhibition of undesirable side effects, preferably selected from the group consisting of hyperthermia, hypertension, and bronchial constriction, caused by administration of vanilloid receptor 1, (VR1/TRPV1 receptor) agonists, preferably selected from the group consisting of capsaicin, resiniferatoxin, olvanil, arvanil, SDZ-249665, SDZ-249482, nuvanil, and capsavanil.

Very high preference is given to the use of at least one substituted cyclic urea derivative of the above general formula I, each optionally in the form of one of its pure stereoisomers, particularly enantiomers or diastereoisomers, its racemates or in the form of a mixture of stereoisomers, particularly the enantiomers and/or diastereoisomers, in an arbitrary mixing ratio, or each in the form of a corresponding salt, or each in the form of a corresponding solvate, and also optionally one or more pharmaceutically compatible adjuvants, for the preparation of a medicinal drug for treatment and/or prophylaxis of one or more disorders selected from the group consisting of pain, preferably pain selected from the group consisting of acute pain, chronic pain, neuropathic pain, and visceral pain; migraine; depression; neurodegenerative disorders, preferably selected from the group consisting of multiple sclerosis, Morbus Alzheimer, Morbus Parkinson, and Morbus Huntington; cognitive dysfunctions, preferably cognitive deficiency states, more preferably memory defects; urinary incontinence; an overactive bladder (OAB); medicine addiction; medicine abuse; withdrawal phenomena following medicine addiction; tolerance development to pharmaceutical preparations, preferably tolerance development to natural or synthetic opioids; drug addiction; drug abuse; withdrawal phenomena following drug addiction; alcohol addiction; alcohol abuse and withdrawal phenomena following alcohol addiction.

Even more preference is given to the use of at least one substituted cyclic urea derivative of the above general formula I, each optionally in the form of one of its pure stereoisomers, particularly enantiomers or diastereoisomers, its racemates or in the form of a mixture of stereoisomers, particularly the enantiomers and/or diastereoisomers, in an arbitrary mixing ratio, or each in the form of a corresponding salt, or each in the form of a corresponding solvate, and also optionally one or more pharmaceutically compatible adjuvants for the preparation of a medicinal drug for treatment and/or prophylaxis of pain, preferably selected from the group consisting of acute pain, chronic pain, neuropathic pain, and visceral pain, and/or urinary incontinence.

The medicinal drug of the invention is suitable for administration to adults and children including infants and babies.

The medicinal drug of the invention can exist as a liquid, semisolid, or solid pharmaceutical dosage form, for example, in the form of injection fluids, drops, juices, syrups, sprays, suspensions, tablets, patches, capsules, plasters, suppositories, ointments, creams, lotions, gels, emulsions, or aerosols, or in a multiparticular form, for example, in the form of pellets or granules, optionally compressed to tablets, filled into in capsules, or suspended in a liquid, and can be administered as such. In addition to at least one substituted cyclic urea derivative of the above general formula I, optionally in the form of one of its pure stereoisomers, particularly enantiomers or diastereoisomers, its racemates or in the form of mixtures of the stereoisomers, particularly the enantiomers or diastereoisomers, in an arbitrary mixing ratio, or optionally in the form of a corresponding salt or each in the form of a corresponding solvate, the medicinal drug of the invention usually contains further physiologically acceptable pharmaceutical adjuvants, preferably selected from the group consisting of support materials, fillers, solvents, diluents, surfactant, dyes, preservatives, blasting agents, slip agents, lubricants, flavors, and binding agents. The selection of the physiologically acceptable adjuvants and the amount thereof to be used depends on whether the medicinal drug is to be applied orally, subcutaneously, parenterally, intravenously, intraperitoneally, intradermally, intramuscularly, intranasally, buccally, rectally or locally, eg, to infected parts of the skin, the mucous membrane, or the eyes. Preparations suitable for oral administration are preferably in the form of tablets, dragees, capsules, granules, pellets, drops, juices, and syrups, and preparations suitable for parenteral, topical, and inhalative administration are solutions, suspensions, readily reconstitutable dry preparations, and sprays.

The substituted cyclic urea derivatives of the invention of the above general formula I present in the medicinal drug of the invention can exist as suitable percutane administration forms in a depot in dissolved form or in a plaster, optionally with the addition of skin penetration enhancing agents. Formulations suitable for oral or percutane application can be adapted for delayed release of the respective substituted cyclic urea derivatives of the invention of the above general formula I. The preparation of the medicinal drugs of the invention is carried out using conventional means, devices, methods and processes known in the prior art as described, for example, in "Remington's Pharmaceutical Sciences", Editor A. R. Gennaro, 17th Edition, Mack Publishing Company, Easton, Pa., 1985, particularly in Section 8, Chapter from 76 to 93. The corresponding description is incorporated herein by reference and is to be regarded as part of the disclosure.

The amount to be administered to the patients of the respective substituted cyclic urea derivatives of the invention of the above general formula I can vary and is, for example, dependent on the weight or age of the patient and also on the method of administration, the indication, and the severity of the disorder. Usually from 0.005 to 100 mg/kg, preferably from 0.05 to 75 mg/kg of body weight of the patient of at least one such compound of the invention are administered.

Pharmacological Methods:

I. Functional Investigation on the Vanilloid Receptor 1 (VR1/TRPV1 Receptor)

The agonistic or antagonistic action of the substances to be investigated on the vanilloid receptor 1 (VR1/TRPV1) of the species rat can be determined using the following assay. According to this assay, the $Ca^{2+}$ influx through the receptor channel is quantified with the aid of a $Ca^{2+}$-sensitive dye (Type Fluo-4, Molecular Probes Europe BV, Leiden Netherlands) in a fluorescent imaging plate reader (FLIPR, Molecular Devices, Sunnyvale, USA).

Method:

Complete medium: 50 mL of HAMS F12 Nutrient Mixture (Gibco Invitrogen GmbH, Karlsruhe, Germany) with 10% by volume of FCS (fetal calf serum, Gibco Invitrogen GmbH, Karlsruhe, Germany, heat-inactivated);

2 mM L-glutamine (Sigma, Munich, Germany);

1% by weight of AA solution (antibiotic/antimycotic solution, PAA, Pasching, Austria) and 25 ng/mL of Medium NGF (2.5 S, Gibco Invitrogen GmbH, Karlsruhe, Germany)

Cell culture plate: Poly-D-lysine-coated, black 96-hole plates with a clear bottom (96 well black/clear plate, BD Biosciences, Heidelberg, Germany) are additionally coated with laminin (Gibco Invitrogen GmbH, Karlsruhe, Germany) by diluting laminin to a concentration of 100 µg/mL with PBS (Ca—Mg-free PBS, Gibco Invitrogen GmbH, Karlsruhe, Germany). Aliquots having a concentration of 100 µg/mL of laminin are taken and stored at −20° C. The aliquots are diluted with PBS in the ratio 1:10 to 10 µg/mL of laminin and in each case 50 µL of the solution is pipetted into a hollow of the cell culture plate. The cell culture plates are incubated at 37° C. for at least two hours, the residual solution is aspirated and the hollows are in each case washed twice with PBS. The coated cell culture plates are stored with residual PBS and this is removed only directly before the addition of the cells.

Preparation of the Cells:

The vertebral column is removed from decapitated rats and this is laid directly in a cold, i.e. ice bath surrounded, HBSS buffer (Hank's buffered saline solution, Gibco Invitrogen GmbH, Karlsruhe, Germany) treated with 1% by volume (percent by volume) of an AA solution (antibiotic/antimycotic solution, PAA, Pasching, Austria). The vertebral column is cut in two longitudinally and the vertebral canal is removed together with fascias. Subsequently, the dorsal root ganglia (DRGs) is removed and in turn stored in cold HBSS buffer treated with 1% by volume of an AA solution. The DRGs completely freed from blood residues and spinal nerves are in each case transferred to 500 µL of cold collagenase Type 2 (PAA, Pasching, Austria) and incubated at 37° C. for 35 minutes. After addition of 2.5% by volume of trypsin (PAA, Pasching, Austria), the preparation is incubated at 37° C. for a further 10 minutes. On completion of incubation, the enzyme solution is carefully pipeted off and the DRGs are in each case treated with 500 µL of complete medium.

The DRGs are in each case repeatedly suspended, drawn through No. 1, No. 12 and No. 16 needles by means of a syringe and transferred to 50 mL Falcon tubes and these are filled to 15 mL with complete medium. The contents of each Falcon tube are in each case filtered through a 70 µm Falcon filter insert and centrifuged at 1200 revolutions and room temperature for 10 minutes. The resulting pellet is in each case taken up in 250 µL of complete medium and the cell count is determined.

The number of cells in the suspension is adjusted to 3 times $10^5$ per mL and in each case 150 µL of this suspension is added to a hollow of the cell culture plates coated as described above. The plates are allowed to stand at 37° C., 5% by volume of $CO_2$ and 95% relative humidity for two to three days in an incubator.

Subsequently, the cells are loaded with 2 µM Fluo-4 and 0.01% by volume of Pluronic F127 (Molecular Probes Europe BV, Leiden Netherlands) in HBSS buffer (Hank's buffered saline solution, Gibco Invitrogen GmbH, Karlsruhe, Germany) at 37° C. for 30 min, washed 3× with HBSS buffer and, after a further incubation of 15 minutes at room temperature, employed in the FLIPR assay for $Ca^{2+}$ measurement. The $Ca^{2+}$-dependent fluorescence is measured before and after addition of substances ($\lambda$ex=488 nm, $\lambda$em=540 nm). Quantification is carried out by the measurement of the highest fluorescence intensity (FC, fluorescence counts) over time.

FLIPR Assay:

The FLIPR protocol consists of 2 substance additions. Initially, the compounds to be tested (10 µM) are pipeted onto the cells and the $Ca^{2+}$ influx is compared with the control (capsaicin 10 µM). Information is gained therefrom in % activation relative to the $Ca^{2+}$ signal after addition of 10 µM capsaicin (CP). After incubation for 5 minutes, 100 nM of capsaicin are applied and the influx of $Ca^{2+}$ is likewise determined.

Desensitizing agonists and antagonists lead to suppression of the $Ca^{2+}$ influx. The % inhibition is calculated in comparison with the maximally achievable inhibition with 10 µM capsaicin.

Triplicate determinations (n=3) are carried out and these are repeated in at least 3 independent experiments (N=4).

Starting from the percentage of displacement by different concentrations of the compounds of the general formula I to be tested, $IC_{50}$ inhibitory concentrations are calculated which bring about a 50 percent displacement of the capsaicin.

II. Formalin Test on Mice

The investigation for the determination of the antinociceptive action of the substituted cyclic urea derivatives of the invention is carried out in the formalin test on male mice (NMRI, 20 to 30 g body weight, Iffa, Credo, Belgium).

In the formalin-test, the first (early) phase (0 to 15 minutes after the formalin injection) and the second (late) phase (15 to 60 minutes after the formalin injection) are distinguished according to D. Dubuisson et al., Pain 1977, 4, 161-174. The early phase, as a direct reaction to the formalin injection, is a model of acute pain, whereas the late phase is regarded as a model of persistent (chronic) pain (T. J. Coderre et al., Pain 1993, 52, 259-285). The corresponding descriptions in the literature are included herein by reference and are considered to be part of the disclosure.

The substituted cyclic urea derivatives of the invention are investigated in the second phase of the formalin test in order to obtain information about substance actions on chronic/inflammatory pain.

The point in time of administration of the substituted cyclic urea derivatives before the formalin injection is chosen depending on the type of administration of the compounds of the invention. The intravenous administration of 10 mg/kg of body weight of the test substances is carried out 5 minutes before the formalin injection. This is carried out by means of a single subcutaneous formalin injection (20 µL, 1% strength aqueous solution) into the dorsal side of the right hind paw, such that with freemoving experimental animals a nociceptive reaction is induced which is manifested in marked licking and biting of the paw concerned.

Subsequently, the nociceptive behavior is continuously recorded by observation of the animals for an investigation period of three minutes in the second (late) phase of the formalin test (21 to 24 minutes after the formalin injection). The quantification of the pain behavior is carried out by summation of the seconds in which the animals show licking and biting of the relevant paw during the investigation period.

The comparison is in each case carried out using control animals, which instead of the compounds of the invention receive vehicle (0.9% strength aqueous sodium chloride solution) before formalin administration.

Based on the quantification of the pain behavior, the substance action in the formalin test is determined as the percentage change compared with the corresponding control.

After injection of substances which are antinociceptivally active in the formalin test, the described behavioral patterns of the animals, i.e. licking and biting, decreases or ceases.

For simplicity and illustrative purposes, the principles of the present invention are described by referring to various examples. One of ordinary skill in the art will readily recognize that the same principles are equally applicable to, and can be implemented in other forms, and that any such variation would be within those modifications that do not part from the true spirit and scope of the present invention. The invention is not limited in its application to the details of any particular formulation shown, since the invention is capable of other embodiments. The following examples are provided for illustrative purposes and do not and should not be understood to limit the claims appended hereto. The terminology used herein is for the purpose of description and not of limitation.

EXAMPLES

The yields of the compounds prepared are not optimized. All temperatures are uncorrected.

| Abbreviations | |
|---|---|
| abs. | dehydrated |
| DCM | dichloromethane |
| DMF | dimethylformamide |
| DMSO | dimethyl sulfoxide |
| EtOH | ethanol |
| MeOH | methanol |
| THF | tetrahydrofuran |
| h | hours |
| min | minutes |
| NMR | NMR spectroscopy |
| RT | room temperature |
| mp | melting point |

The chemicals and solvents used were obtained commercially from the conventional suppliers (Acros, Avocado, Aldrich, Bachem, Fluka, Lancaster, Maybridge, Merck, Sigma, TCI, etc.) or synthesized by methods known to the person skilled in the art.

The stationary phase used for column chromatography was silica gel 60 (0.040-0.063 mm) supplied by E. Merck, Darmstadt.

The thin-layer chromatographic analyses were carried out using preformed HPTLC plates, Silica Gel 60 F 254, supplied by E. Merck, Darmstadt.

The mixing ratios of solvents, mobile solvents, including for chromatographic analyses are always given in vol/vol.

Chemical analysis was carried out by mass spectroscopy and NMR.

General synthesis scheme 1:

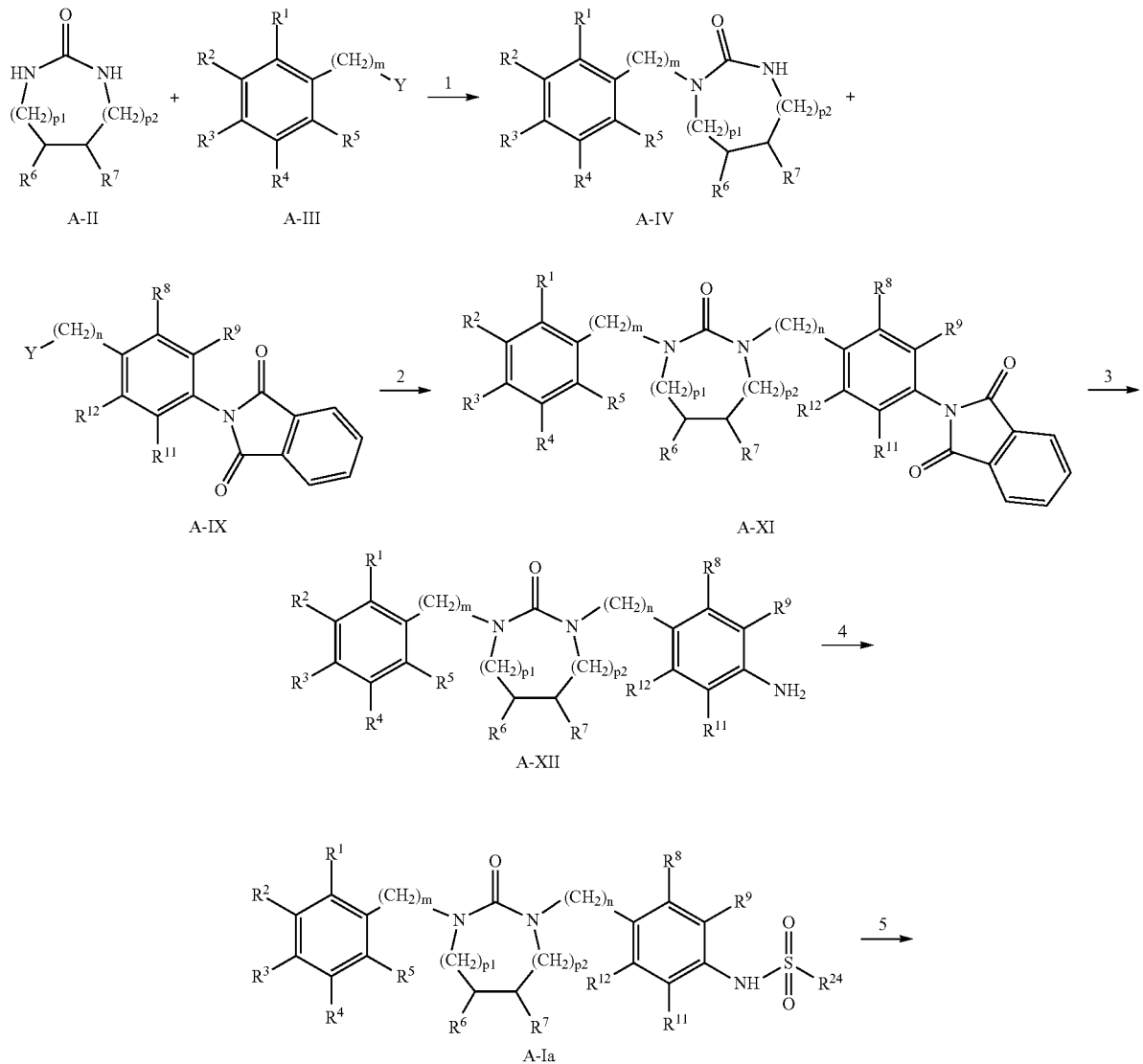

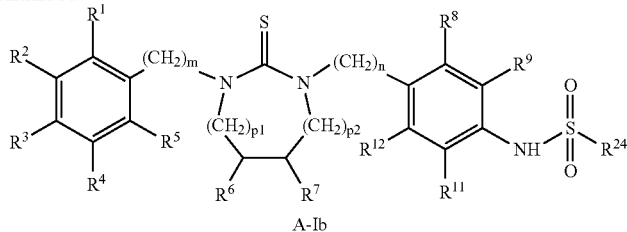

A-Ib

In stage 1 the reaction of compounds of the general formula A-II with compounds of the general formula A-III was carried out under a blanket of argon in organic solvents or solvent mixtures, for example, diethyl ether, THF, DCM, DMF, acetonitrile, pyridine, DMSO, and toluene, with the addition a metal hydride salt, for example, with the addition of sodium hydride or potassium hydride, at temperatures ranging from 20° to 30° C. to produce compounds of the general formula A-IV.

If the monoalkylation product of the general formula A-IV is obtained as a mixture with the corresponding dialkylation product, the monoalkylation product is obtained by recrystallization of the mixture from a solvent mixture comprising $H_2O$ and EtOH.

In stage 2 the reaction of compounds of the general formula A-IV with compounds of the general formula A-IX is carried out under a blanket of argon in organic solvents or solvent mixtures, for example, diethyl ether, THF, DCM, DMF, acetonitrile, pyridine, DMSO, and toluene, with the addition a metal hydride salt, for example, with the addition of sodium hydride or potassium hydride, at temperatures ranging from 20° to 30° C., and then at temperatures ranging from 80° to 120° C., to produce compounds of the general formula A-XI.

In stage 3 the reaction of compounds of the general formula A-XI was carried out in organic solvents or solvent mixtures, for example, MeOH, EtOH, isopropanol, and water, with the addition of hydrazine hydrate, phenylhydrazine, or dimethylamine, at temperatures ranging from 20° to 30° C. to form compounds of the general formula A-XII. Alternatively, compounds of the general formula A-XI were caused to react in organic solvents or solvent mixtures, for example, mixtures of MeOH, EtOH, and isopropanol, with the addition of sodium tetrahydridoborate, at temperatures ranging from 20° to 30° C. to form compounds of the general formula A-XII.

In stage 4 the reaction of compounds of the general formula A-XII with compounds of the general formula $R^{24}$—S(=O)$_2$—Z was carried out in organic solvents or solvent mixtures, for example, mixtures of acetone, diethyl ether, THF, DCM, DMF, acetonitrile, pyridine, DMSO, and toluene, optionally with the addition of a base, for example, pyridine, triethylamine, and diisopropylethylamine, at temperatures ranging from 20 to 30° C., to obtain compounds of the general formula A-Ia.

In stage 5 the conversion of compounds of the general formula A-Ia was carried out in organic solvents or solvent mixtures, for example, mixtures of toluene, para-xylene, ortho-xylene, meta-xylene, acetonitrile, DCM, and DMF, with the addition a dithiaphosphetan, for example, 2,4-bis(4-methoxyphenyl)-1,3,2,4-dithiadiphosphetan-2,4-disulfide (Lawesson's reagent), or with the addition of phosphorus pentasulfide, at temperatures ranging from 50° to 150° C. to obtain compounds of the general formula A-Ib.

General synthesis scheme 2:

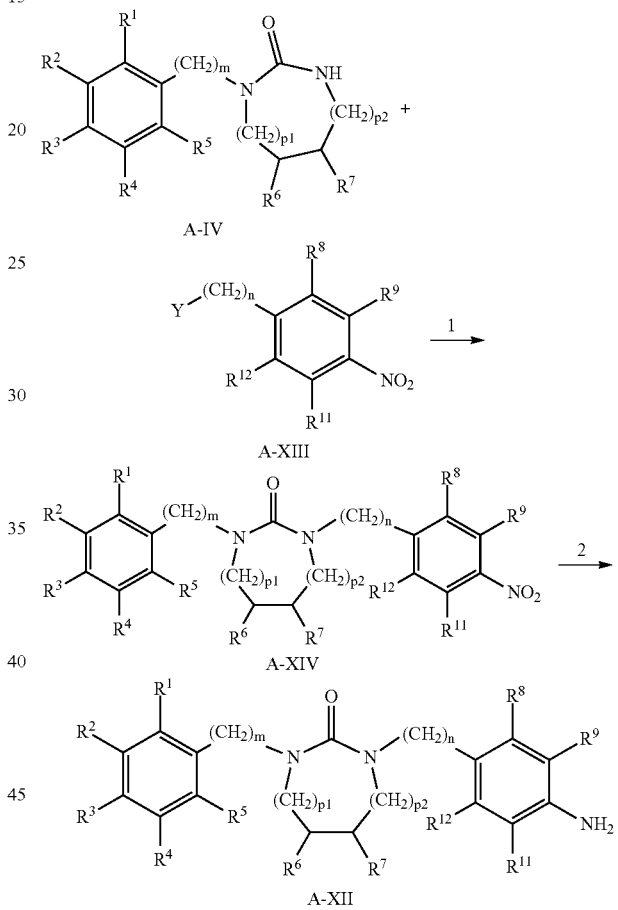

The compounds of the general formula A-IV were obtained as described in the general synthesis scheme 1, stage 1.

In stage 1 the reaction of compounds of the general formula A-IV with compounds of the general formula A-XIII was carried out under a blanket of argon in organic solvents or solvent mixtures, for example, mixtures of diethyl ether, THF, DCM, DMF, acetonitrile, pyridine, DMSO, and toluene, with the addition a metal hydride salt, for example, with the addition of sodium hydride or potassium hydride, at temperatures ranging from 20 to 30° C., and then at temperatures ranging from 80° to 120° C., to produce compounds of the general formula A-XIV.

In stage 2 the conversion of compounds of the general formula A-XIV was carried out in organic solvents or solvent mixtures, for example, mixtures of MeOH, EtOH, isopropanol, acetone, diethyl ether, THF, DCM, DMF, acetonitrile, pyridine, DMSO, and toluene, in a hydrogen atmosphere, for example, a hydrogen atmosphere under a pressure of 2 bar, at temperatures ranging from 20° to 30° C., to produce compounds of the general formula A-XII.

The compounds of the general formula A-XII were further converted, as described in general synthesis scheme 1, stages 4 and 5, to produce compounds of the general formula A-Ia or A-Ib.

General synthesis scheme 3:

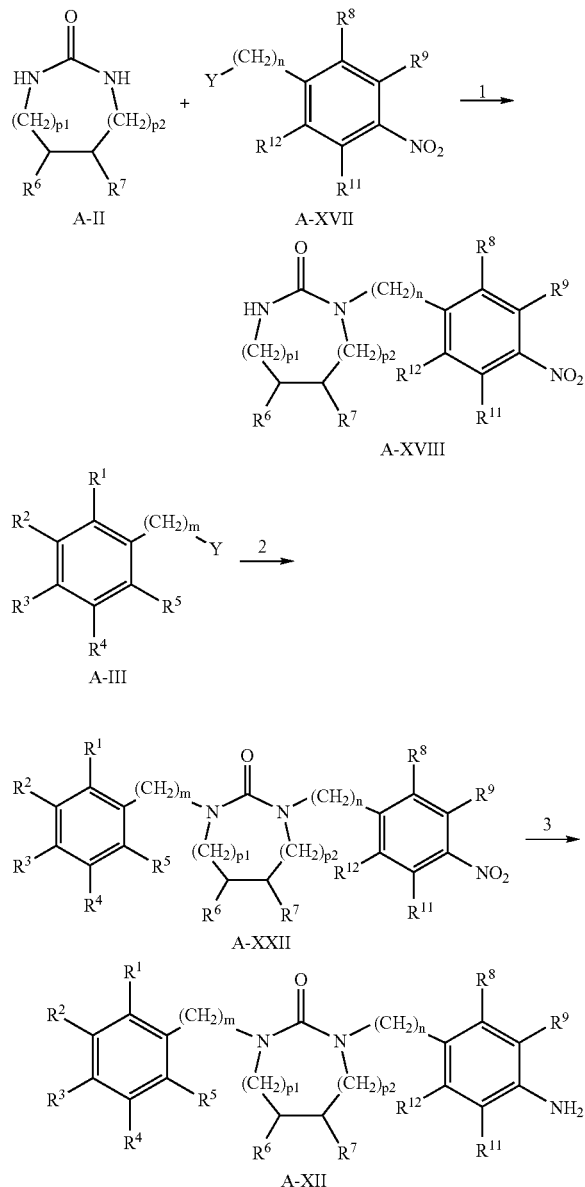

In stage 1 the reaction of compounds of the general formula A-II with compounds of the general formula A-XVII was carried out in organic solvents or solvent mixtures, for example, mixtures of diethyl ether, THF, DCM, DMF, acetonitrile, pyridine, DMSO, and toluene, with the addition of an alkali metal carbonate salt, for example, with the addition of potassium carbonate or sodium carbonate, and with the addition of an alkali metal iodide, for example, with the addition of potassium iodide or sodium iodide, at temperatures ranging from 70° to 120° C., to produce compounds of the general formula A-XVIII.

If the monoalkylation product of the general formula A-XVIII was obtained as a mixture with the corresponding dialkylation product, the monoalkylation product was obtained as the less polar compound by column chromatography on $SiO_2$ using mixtures of cyclohexane and EtOAc as the mobile solvent.

In stage 2 the reaction of compounds of the general formula A-XVIII with compounds of the general formula A-III was carried out in organic solvents or solvent mixtures, for example, mixtures of diethyl ether, THF, DCM, DMF, acetonitrile, pyridine, DMSO, and toluene, with the addition an alkali metal carbonate salt, for example, with the addition of potassium carbonate or sodium carbonate, and with the addition an alkali metal iodide, for example, with the addition of potassium iodide or sodium iodide, at temperatures ranging from 70° to 120° C., to produce compounds of the general formula A-XXII.

In stage 3 the conversion of compounds of the general formula A-XXII was carried out in organic solvents or solvent mixtures, for example, mixtures of MeOH, EtOH, isopropanol, acetone, diethyl ether, THF, DCM, DMF, acetonitrile, pyridine, DMSO, and toluene, in a hydrogen atmosphere, for example, a hydrogen atmosphere under a pressure of 2 bar, at temperatures ranging from 20° to 30° C., to produce compounds of the general formula A-XII.

The compounds of the general formula A-XII were further reacted, as described in general synthesis scheme 1, stages 4 and 5, to produce compounds of the general formula A-Ia or A-Ib.

I. Synthesis of Compounds of the General Formula II in which X=N—C≡N a. Synthesis of 2-cyanoimino-imidazolidine

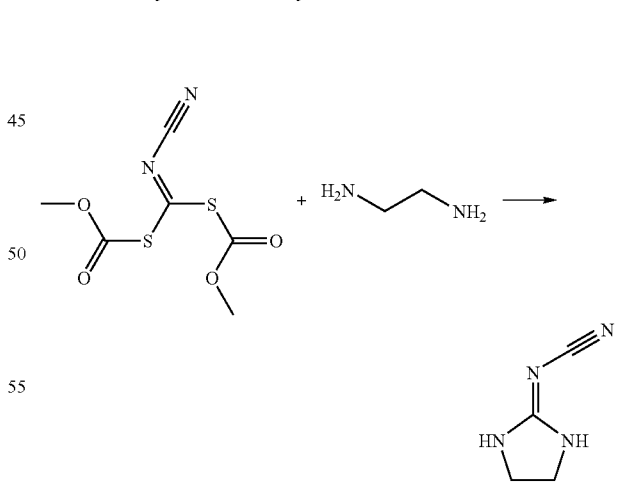

1,2-Diaminoethane (200 mL) was added to chloroform (150 mL), and a solution of dimethyl N-cyanimino-dithiocarboxylate (50 g, 0.34 mol) in chloroform was added with stirring in such a manner that the temperature was kept below 45° C. The reaction mixture was then stirred at RT over a period of 30 minutes, the volatile matter removed in vacuo and the residue recrystallized from EtOH. There were obtained 28.1 g (256 mmol, 75% of theory) of the desired compound 2-cyanoimino-imidazolidine.

b. Synthesis of 2-cyanimino-hexahydropyrimidine

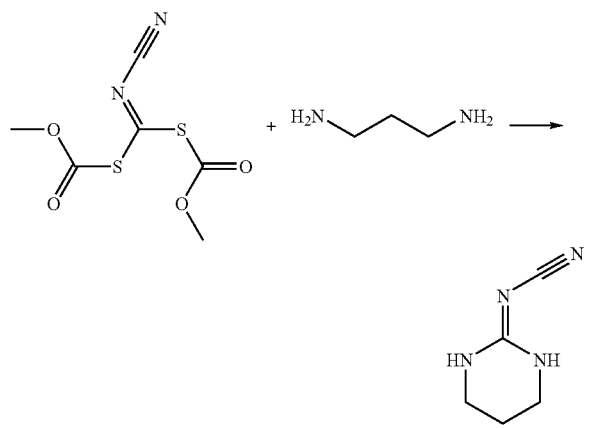

1,3-Diaminopropane (250 mL) was added to n-propanol (150 mL), and a solution of dimethyl N-cyanimino-dithiocarboxylate (50 g, 0.34 mol) in n-propanol was added with stirring in such a manner that the temperature was kept below 45° C. The reaction mixture was then heated under reflux over a period of 2.5 h, the volatile matter removed in vacuo and the residue recrystallized from EtOH. There were obtained 11.0 g (88.5 mmol, 26% of theory) of the desired compound 2-cyanimino-hexahydropyrimidine.

II. Synthesis of the exemplary compounds 1 and 4: N-{4-[3-(4-tert-butylbenzyl)-2-thioxoimidazolidinyl-methyl]phenyl}methane-sulfonamide (1) and N-{4-[3-(4-tert-butylbenzyl)-2-oxoimidazolidin-1-ylm-ethyl]phenyl}methane-sulfonamide (4)

a. Synthesis of 2-p-tolylisoindol-1,3-dione (A)

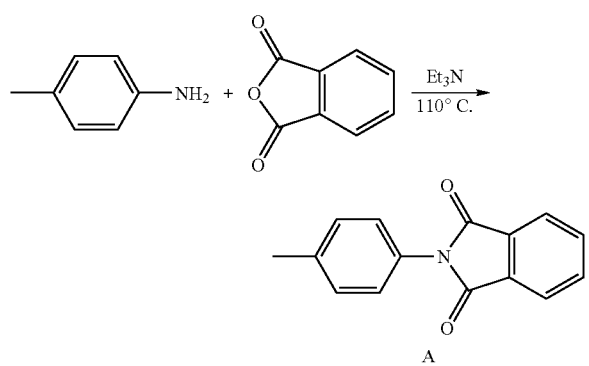

To a mixture of phthalic anhydride (7.4 g, 50.0 mmol) and p-toluidine (53.5 g, 50.0 mmol) there were added toluene (200 mL) and triethylamine (1 mL, 7.2 mmol) and the mixture was heated to the boil in a water separator over a period of 3 h. The resulting solution was filtered hot through a frit comprising kieselguhr (0.5-1 cm layer thickness). The residue was washed with hot toluene (2×50 mL). The resulting solution was concentrated to approximately 100 mL, resulting in crystallization. The precipitated solid matter (7.8 g, 66% of theory) represents the desired product 2-p-tolylisoindol-1,3-dione (A) and has a melting point (201-203° C.) equivalent to that given in the literature [Kaupp, G. et al. Tetrahedron 2000, 56, 6899-6912].

b. Synthesis of 2-(4-bromomethylphenyl)-isoindol-1,3-dione (B)

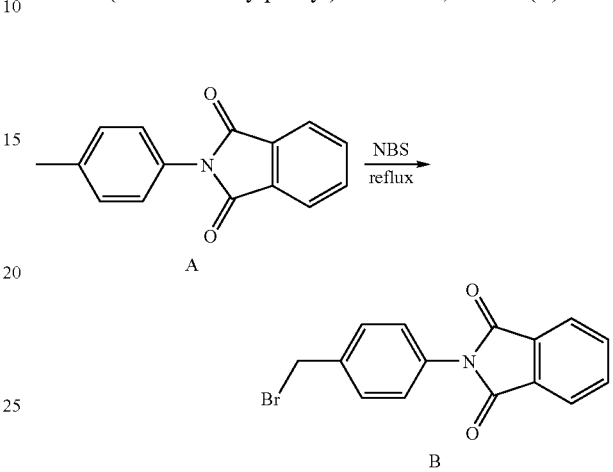

To a mixture of 2-p-tolylisoindol-1,3-dione (A) (4.0 g, 17 mmol) and N-bromosuccinimide (3.0 g, 17 mmol) there were added carbon tetrachloride (70 mL) and benzoyl peroxide (8 mL) and the mixture was heated to the boil under halogen radiation over a period of 2 h. The resulting reaction solution was concentrated. The residue was stirred with chloroform (300 mL) with heating for 15 min and the mixture then filtered hot for isolation of the resulting solid matter. The filtrate was concentrated in vacuo, and the residue was purified by column chromatography (SiO$_2$ (150 g) using cyclohexane/EtOAc 4:1 (2000 mL) as eluent). The bromide 2-(4-bromomethylphenyl)isoindol-1,3-dione (B) (4.1 g, 77%) was isolated as a white solid having a melting point of 191-199° C.

c. Synthesis of 1-(4-tert-butylbenzyl)imidazolidin-2-one (C)

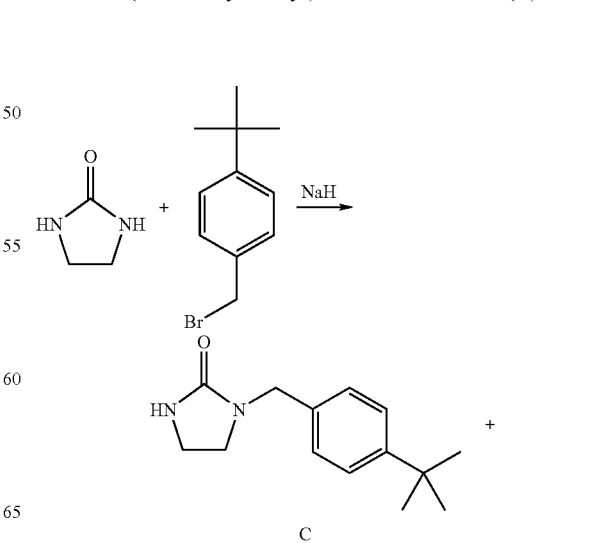

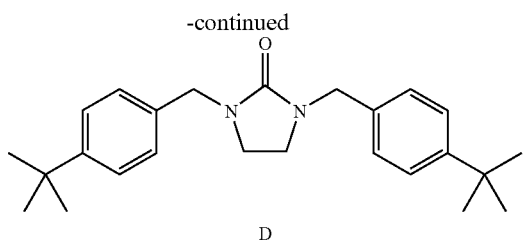

Sodium hydride (approximately 60% strength suspension in oil, 1.2 g, approximately 30 mmol) was added portionwise to a solution of imidazolidin-2-one (2.58 g, 30 mmol) in abs. DMF (40 mL) under a blanket of argon within 10 min. The reaction mixture was stirred for 90 min at RT and a solution of 4-tert-butylbenzyl bromide (3.7 mL, 20.1 mmol) in abs. DMF (3 mL) was then added. The reaction mixture was stirred at RT over a period of 3 h and then added to a mixture of $H_2O$ (100 mL) and 2N hydrochloric acid solution in $H_2O$ (10 mL). The resulting mixture was stirred for 30 min, and the resulting crystals were separated with the aid of a frit and washed with $H_2O$ (3×30 mL). The isolated solid matter was recrystallized from a mixture of $H_2O$ (100 mL) and EtOH (120 mL). The substance formed (1.4 g, mp: 122-127° C.) is compound D.

The remaining mother liquor was concentrated in vacuo. The precipitated crystals (1.87 g, 40% of theory, mp: 161-165° C.) proved to be the desired compound 1-(4-tert-butyl-benzyl)imidazolidin-2-one (C).

d. Synthesis of 2-{4-[3-(4-tert-butylbenzyl)-2-oxoimidazolidin-1-ylmethyl]phenyl}-isoindol-1,3-dione (E)

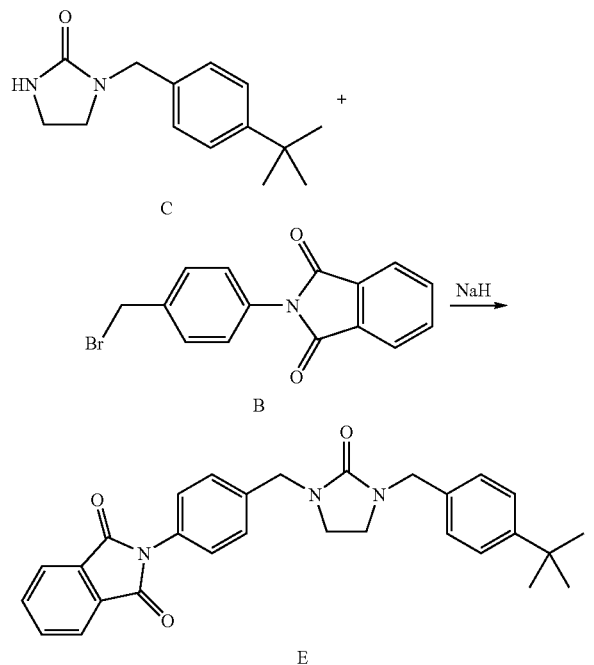

Sodium hydride (approximately 60% strength suspension in oil, 140 mg, approximately 3.5 mmol) was added portionwise to a solution of 1-(4-tert-butylbenzyl)imidazolidin-2-one (C) (730 mg, 3.15 mmol) in abs. DMF (15 mL) under a blanket of argon within a period of 10 min. The reaction mixture was stirred for 60 min at RT and a solution of 2-(4-bromomethylphenyl)-isoindol-1,3-dione (B) (1 g, 3.16 mmol) in abs. DMF (20 mL) was then added within a period of 60 min. The reaction mixture was stirred at RT over a period of 3 h, then heated to 100° C. over a period of 1 h, cooled, and added to a mixture of ice water (300 mL) and 2N hydrochloric acid solution in $H_2O$ (20 mL). The resulting mixture was stirred for 30 min and then extracted with DCM (4×20 mL). The combined organic phases were dried over $Na_2SO_4$ and the solvent removed in vacuo. Following purification, by column chromatography, of the residue ($SiO_2$, cyclohexane/EtOAc 1:1), the desired product 2-{4-[3-(4-tert-butylbenzyl)-2-oxoimidazolidin-1-ylmethyl]phenyl}isoindol-1,3-dione (E) was obtained as vitreous solid matter (680 mg, 46% of theory).

e. Synthesis of 1-(4-aminobenzyl)-3-(4-tert-butyl-benzyl)-imidazolidin-2-one (F)

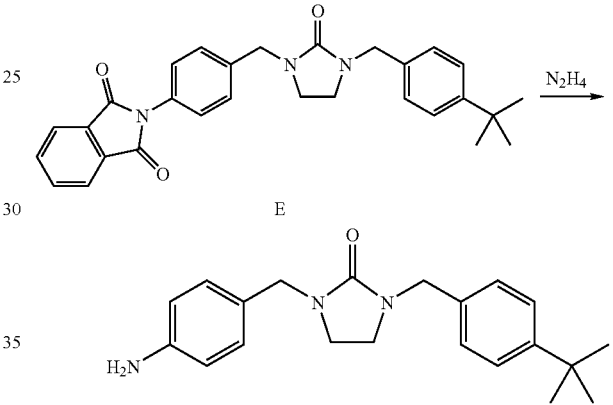

To a solution of 2-{4-[3-(4-tert-butylbenzyl)-2-oxoimidazolidin-1-ylmethyl]phenyl}isoindol-1,3-dione (E) (654 mg, 1.4 mmol) in MeOH (30 mL) hydrazine hydrate was added as a 0.8 M solution in MeOH (10 mL, 8 mmol) with stirring at RT. The reaction mixture was stirred for 90 min at RT and then $H_2O$ (50 mL) was added. The solvent was removed in vacuo and the residue was extracted with EtOAc (3×20 mL). The combined organic phases were dried over $Na_2SO_4$ and the solvent again removed in vacuo. There were obtained 430 g (91% of theory) of the desired product 1-(4-aminobenzyl)-3-(4-tert-butylbenzyl)-imidazolidin-2-one (F).

f. Synthesis of N-{4-[3-(4-tert-butylbenzyl)-2-oxoimidazolidin-1-ylmethyl]-phenyl}methanesulfonamide (4)

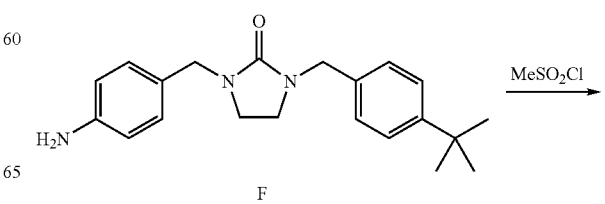

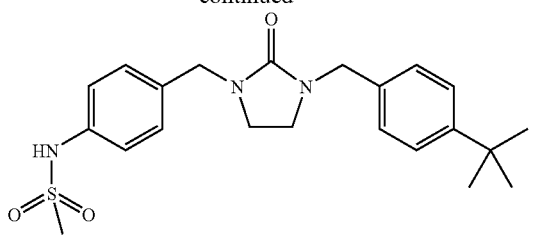

4

+

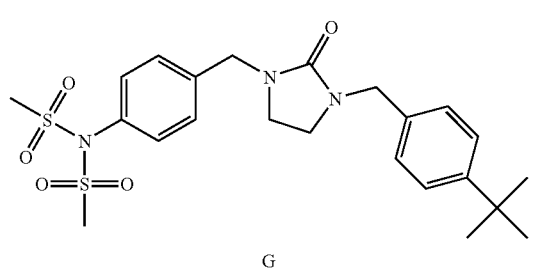

G

To a solution of 1-(4-aminobenzyl)-3-(4-tert-butylbenzyl)-imidazolidin-2-one (F) (410 mg, 1.22 mmol) and triethylamine (0.2 mL, 1.44 mmol) in abs. THF there was added a solution of methanesulphonyl chloride (0.12 mL, 1.56 mmol) in 0.8 mL of abs. THF within a period of 20 min. The reaction mixture was stirred over a period of 15 h at RT, sat. NaHCO₃ solution (10 mL) was added, and the mixture was stirred for 30 min. H₂O (30 mL) was added and the mixture was extracted with EtOAc (3×20 mL). The combined organic phases were washed with sat. NaCl solution, dried over Na₂SO₄, and the solvent was removed in vacuo. Following purification, by column chromatography, of the residue (SiO₂, EtOAc/cyclohexane 2:1), there were obtained the desired product N-{4-[3-(4-tert-butylbenzyl)-2-oxoimidazolidin-1-ylmethyl]phenyl}methanesulfonamide (4) (70 mg, 14% of theory, mp: 166-168° C.) and N-{4-[3-(4-tert-butylbenzyl)-2-oxoimidazolidin-1-ylmethyl]phenyl}-N,N-bis(methanesulfonyl)imide (G) (160 mg, mp: 184-187° C.).

g. Synthesis of N-{4-[3-(4-tert-butylbenzyl)-2-thioxoimidazolidinylmethyl]phenyl}-methanesulfonamide (1)

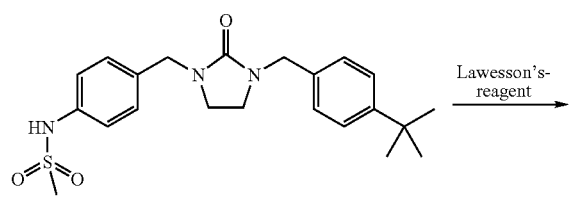

4

Lawesson's-reagent →

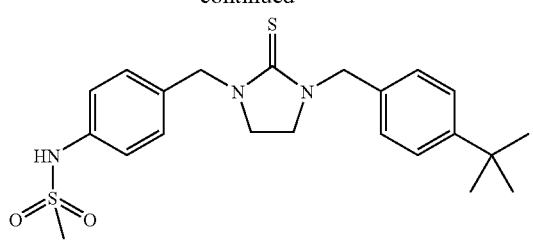

1

Lawesson's reagent (2,4-bis(4-methoxyphenyl)-1,3,2,4-dithiadiphosphetan-2,4-disulfide) (640 mg, 1.58 mmol) was added to a solution of N-{4-[3-(4-tert-butylbenzyl)-2-oxoimidazolidin-1-ylmethyl]phenyl}methanesulfonamide (4) (1008 mg, 2.63 mmol) in abs. toluene (30 mL). The reaction mixture was heated to the boil over a period of 5 h. The reaction mixture was then stirred overnight. Water (40 mL) was added and the mixture was extracted with chloroform (3×30 mL). The combined organic phases were washed with H₂O (2×20 mL), dried over Na₂SO₄, and the solvent was removed in vacuo. Following purification of the residue by means of column chromatography (SiO₂ (150 g); 1000 mL cyclohexane/EtOAc 4:1), the desired product N-{4-[3-(4-tert-butylbenzyl)-2-thioxoimidazolidinylmethyl]phenyl}methanesulfonamide (1) (545 mg, 52% of theory) was obtained.

III. Synthesis of the exemplary compounds 3 and 5: N-{4-[3-(4-tert-butylbenzyl)-2-thioxotetrahydropyrimidin-1-ylmethyl]phenyl}-methanesulfonamide (3) and N-{4-[3-(4-tert-butylbenzyl)-2-oxotetrahydropyrimidin-1-ylmethyl]phenyl}-methanesulfonamide (5)

a. Synthesis of 1-(4-nitrobenzyl)tetrahydropyrimidin-2-one (H)

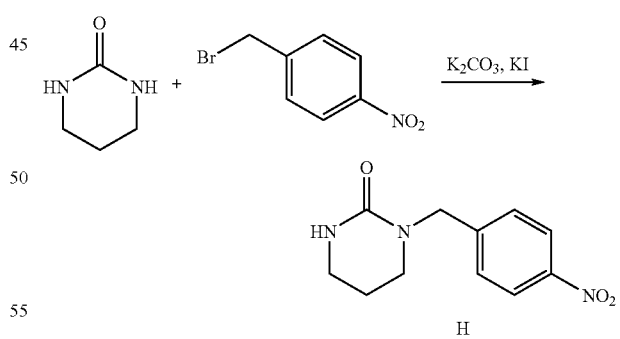

H

To a solution of 3,4,5,6-tetrahydro-2-(1H)-pyrimidinone (4 g, 0.04 mol) in abs. DMF (50 mL) there were added potassium carbonate (5.5 g, approximately 0.04 mol), potassium iodide (3.3 g, 0.02 mol), and 4-nitrobenzyl bromide (8.6 g, 0.04 mol) at RT. The reaction mixture was stirred at 100° C. over a period of 2 h. Following cooling of the reaction mixture, it was added to ice water (500 mL). The precipitated solid matter was filtered off in vacuo and washed with a little acetyl (4×10 mL). The desired product 1-(4-nitrobenzyl)tetrahydropyrimidin-2-one (H) was obtained as yellow solid matter (3.5 g, 40% of theory) having a melting point of 150-162° C.

b. Synthesis of 1-(4-tert-butylbenzyl)-3-(4-nitrobenzyl)-tetrahydropyrimidin-2-one (K)

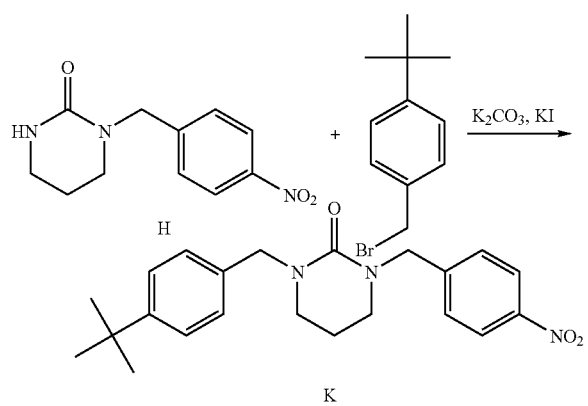

To a solution of 1-(4-nitrobenzyl)tetrahydropyrimidin-2-one (H) (1.94 g, 8.15 mmol) in abs. DMF (30 mL) there were added potassium carbonate (1.12 g, approximately 8.15 mmol), potassium iodide (0.7 g, 4 mmol), and 4-tert-butylbenzyl bromide (1.85 g, 8.15 mmol) at RT. The reaction mixture was stirred at 100° C. over a period of 3 h. Following cooling of the reaction mixture, it was poured into ice water (350 mL). The mixture was extracted with dichloromethane (3×40 mL). The organic phase was washed with $H_2O$ (2×30 mL) and dried over $Na_2SO_4$, and the solvent was removed in vacuo. After purification, by column chromatography, of the residue ($SiO_2$ (150 g), cyclohexane/EtOAc 1:1 (2000 mL) as eluent), the desired compound 1-(4-tert-butyl benzyl)-3-(4-nitrobenzyl)tetrahydropyrimidin-2-one (K) was obtained as a yellow oil (786 mg, 25% of theory).

c. Synthesis of 1-(4-aminobenzyl)-3-(4-tert-butyl-benzyl)tetrahydropyrimidin-2-one (L)

To a solution of 1-(4-tert-butylbenzyl)-3-(4-nitrobenzyl) tetrahydropyrimidin-2-one (K) (500 mg, 1.31 mmol) in abs. MeOH (50 mL) palladium on charcoal (5%, 600 mg) was added. The reaction mixture was subjected to a hydrogen pressure of 2 bar for 20 min at RT. The catalyst was separated by filtration through Celite and the filtrate was concentrated in vacuo. The desired product 1-(4-aminobenzyl)-3-(4-tert-butylbenzyl)-tetrahydropyrimidin-2-one (L) was obtained as a colorless oil (364 mg, 79% of theory).

d. Synthesis of N-{4-[3-(4-tert-butylbenzyl)-2-oxotetrahydropyrimidin-1-ylmethyl]-phenyl}methanesulfonamide (5)

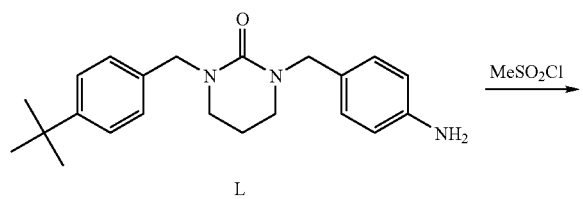

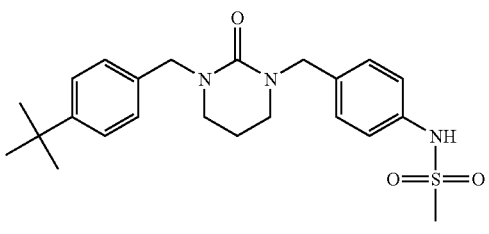

To a solution of 1-(4-aminobenzyl)-3-(4-tert-butylbenzyl)-tetrahydropyrimidin-2-one (L) (438 mg, 1.24 mmol) and triethylamine (0.22 mL, 1.6 mmol) in abs. THF (50 mL) there was added a solution of methanesulphonyl chloride (0.11 mL, 1.48 mmol) in 5 mL of abs. THF within a period of 15 min. The reaction mixture was stirred over a period of 48 h at RT, sat. $NaHCO_3$ solution (20 mL) was added, and the mixture was stirred for 30 min. $H_2O$ (30 mL) was added, and the mixture was extracted with EtOAc (3×30 mL). The combined organic phases were washed with sat. NaCl solution (30 mL), dried over $Na_2SO_4$, and the solvent was removed in vacuo. The residue was purified by means of column chromatography ($SiO_2$ (50 g) using cyclohexane/EtOAc 1:1 (500 mL) as eluent). The desired product N-{4-[3-(4-tert-butyl benzyl)-2-oxotetrahydropyrimidin-1-yl methyl]phenyl}methanesulfonamide (5) was obtained as a white solid (398 mg, 75% of theory) having a melting point of 132-135° C.

The compound N-{4-[3-(4-tert-butyl benzyl)-2-thioxotetrahydropyrimidin-1-ylmethyl]phenyl}methanesulfonamide (3) was obtained from N-{4-[3-(4-tert-butyl benzyl)-2-oxotetrahydropyrimidin-1-ylmethyl] phenyl}methanesulfonamide (5) in a manner similar to that described in the reaction described under II g.

IV. Synthesis of the exemplary compounds 2 and 6: N-{4-[3-(4-tert-butylbenzyl)-2-thioxo-2,3-dihydrobenzoimidazol-1-ylmethyl]-phenyl}methanesulfonamide (2) and N-{4-[3-(4-tert-Butyl-benzyl)-2-oxo-2,3-dihydrobenzoimidazol-1-ylmethyl]-phenyl}methanesulfonamide (6)

a. Synthesis of 1-(4-tert-butylbenzyl)-1,3-dihydrobenzimidazol-2-one (N)

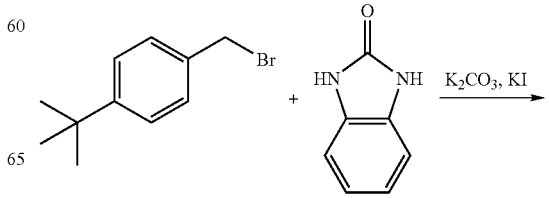

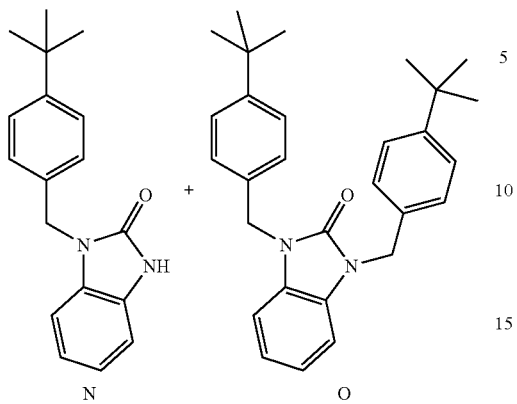

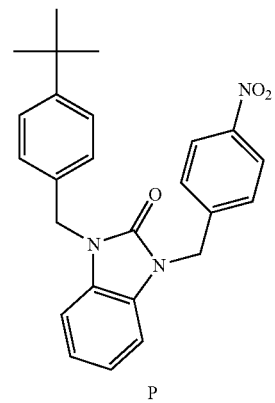

To a solution of benzimidazolinone (1.5 g, 11.2 mmol) in abs. DMF (25 mL) there were added 4-tert-butylbenzyl bromide (1.8 mL, 9.8 mmol), potassium carbonate (2.76 g, 20 mmol), and a catalytic amount of potassium iodide under a blanket of argon. The reaction mixture was heated to 75° C. over a period of 2 h. Following cooling, the reaction mixture was poured into a solution of H₂O (200 mL) and 2N hydrochloric acid solution in H₂O (10 mL). The resulting mixture was extracted with EtOAc (5×40 mL), the combined organic phases were washed with sat. NaCl solution (2×30 mL), dried over Na₂SO₄, and the solvent was removed in vacuo. The residue was taken up in chloroform (50 mL), and the resulting solid matter was isolated by filtration. The filtrate was concentrated in vacuo. The residue was purified by means of column chromatography (SiO₂, cyclohexane/EtOAc 2:1), and there were obtained 1,3-bis(4-tert-butylbenzyl)-1,3-dihydrobenzimidazol-2-one (O) (0.9 g, mp: 164-168° C.) and the desired product 1-(4-tert-butylbenzyl)-1,3-dihydrobenzimidazol-2-one (N) (615 mg, 22% of theory, mp: 179-180° C.) as the more polar substance.

b. Synthesis of 1-(4-tert-butylbenzyl)-3-(4-nitrobenzyl)-1,3-dihydrobenzimidazol-2-one (P)

To a solution of compound N (1.12 g, 4.0 mmol) in abs. DMF (30 mL) there were added 4-nitrobenzyl bromide (864 mg, 4.0 mmol), potassium carbonate (1.14 g, 8.30 mmol), and a catalytic amount of potassium iodide under a blanket of argon. The reaction mixture was heated to 75° C. over a period of 4 h. Following cooling, the reaction mixture was poured into a mixture of ice (300 g) and 2N hydrochloric acid solution in H₂O (200 mL), and the reaction mixture was stirred for 1 hour. The resulting solid matter was separated through a frit and dried in vacuo over calcium chloride. The desired product 1-(4-tert-butylbenzyl)-3-(4-nitrobenzyl)-1,3-dihydrobenzimidazol-2-one (P) was obtained in an adequately pure form for synthetic purposes in a yield of 1.48 g (89% of theory).

c. Synthesis of 1-(4-aminobenzyl)-3-(4-tert-butylbenzyl)-1,3-dihydrobenzimidazol-2-one (Q)

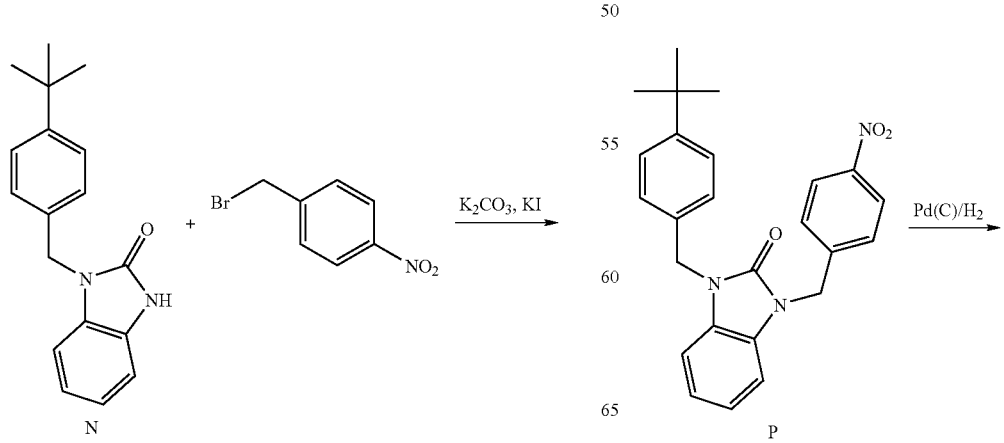

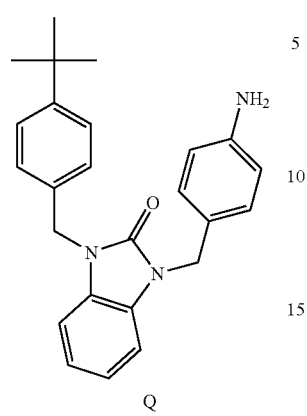

Q

Palladium-on-charcoal (5%, 650 mg) was added to a solution of 1-(4-tert-butylbenzyl)-3-(4-nitrobenzyl)-1,3-dihydrobenzimidazol-2-one (P) (1.13 g, 2.73 mmol) in abs. MeOH (60 mL). The reaction mixture was subjected to a hydrogen pressure of 3 bar for 20 min at RT. The catalyst was separated by filtration, and the filtrate was concentrated in vacuo. The residue was taken up in EtOAc (10 mL) and filtered through a frit with kieselguhr (layer thickness 1 cm). The frit was washed with ethyl acetate (4×20 mL). The desired product 1-(4-aminobenzyl)-3-(4-tert-butylbenzyl)-1,3-dihydrobenzimidazol-2-one (Q) was obtained in a yield of 960 mg (91% of theory). The corresponding hydrochloride was obtained by reaction of 1-(4-aminobenzyl)-3-(4-tert-butylbenzyl)-1,3-dihydrobenzimidazol-2-one (Q) with chlorotrimethylsilane (1 mL, 7.9 mmol) in DCM (50 mL). The reaction mixture was stirred over a period of 17 h without exclusion of moisture, and the resulting solid matter was separated with the aid of a frit and then dried. The hydrochloride was obtained as solid matter (750 mg, 68% of theory, mp: 198-219° C.).

d. Synthesis of N-{4-[3-(4-tert-Butyl-benzyl)-2-oxo-2,3-dihydrobenzoimidazol-1-ylmethyl]-phenyl}methanesulfonamide (6)

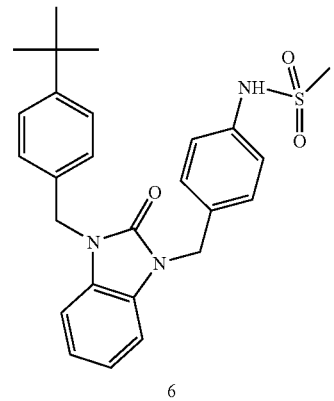

6

Pyridine (0.3 mL, 3.72 mmol) was added to a suspension of the hydrochloride of 1-(4-aminobenzyl)-3-(4-tert-butylbenzyl)-1,3-dihydrobenzimidazol-2-one (Q) (717 mg, 1.7 mmol) in abs. THF (20 mL). The reaction mixture was stirred at RT for 10 min, methanesulphonyl chloride (0.13 mL, 1.7 mmol, dissolved in abs. THF (1 mL)) was added within a period of 5 min, and the reaction mixture was again stirred at RT over a period of 17 h. To the reaction mixture there was then added $H_2O$ (10 mL) followed, after 10 min, by $H_2O$ (100 mL). After an hour the precipitated solid matter was separated through a frit and then dried in vacuo. The desired product N-{4-[3-(4-tert-Butyl-benzyl)-2-oxo-2,3-dihydrobenzoimidazol-1-ylmethyl]phenyl}methanesulfonamide (60) was obtained in a yield of 680 mg (86% of theory, mp: 228-230° C.).

e. Synthesis of N-{4-[3-(4-tert-butylbenzyl)-2-thioxo-2,3-dihydrobenzoimidazol-1-ylmethyl]phenyl}methanesulfonamide (2)

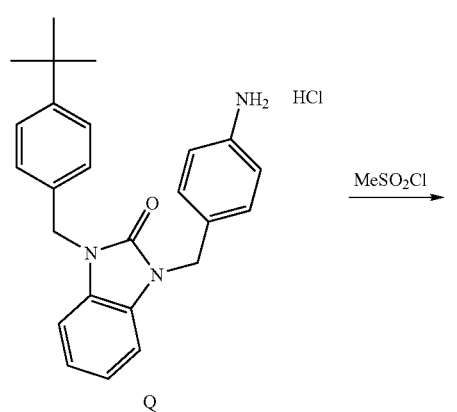

Q

→ MeSO₂Cl

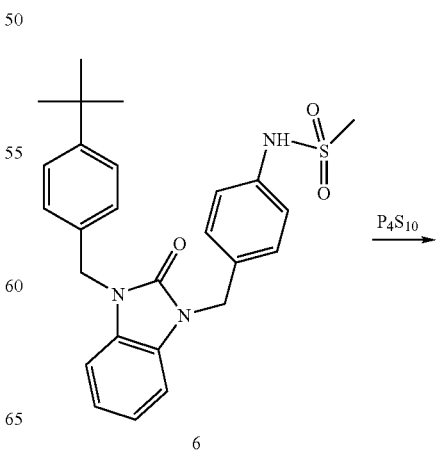

6

→ $P_4S_{10}$

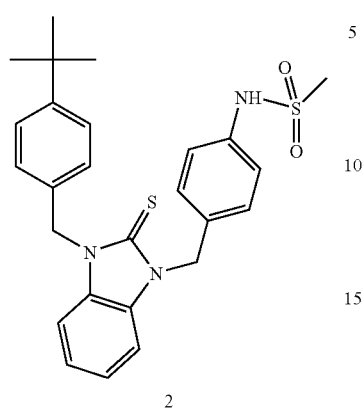

2

Phosphorus pentasulfide (300 mg, 0.67 mmol) was added to a suspension of N-{4-[3-(4-tert-butylbenzyl)-2-oxo-2,3-dihydrobenzimidazol-1-ylmethyl]phenyl}methanesulfonamide (6) (235 mg, 0.51 mmol) in para-xylene (20 mL) under a blanket of argon. The reaction mixture was heated to the boil over a period of 5 h. Following cooling, there was added to the reaction mixture water (1 mL) followed by 2N NaOH solution in water (10 mL), and the mixture was stirred at RT for 30 min. To the reaction mixture there was added aqueous NaCl solution, and the resulting mixture was extracted with ethyl acetate (4×20 mL). The combined organic phases were dried over $Na_2SO_4$ and the solvent removed in vacuo. After purifying the residue by means of column chromatography ($SiO_2$; cyclohexane/EtOAc 7:3), the desired product N-{4-[3-(4-tert-butylbenzyl)-2-thioxo-2,3-dihydrobenzoimidazol-1-ylmethyl]phenyl}methanesulfonamide (2) (99 mg, 40% of theory, mp: 176-178° C.) was obtained.

V. Synthesis of the exemplary compounds 7 and 8:
N-{4-[3-(4-trifluoromethoxybenzyl)-2-oxo-2,3-dihydrobenzimidazol-1-ylmethyl]phenyl}methanesulfonamide (7) and N-{4-[3-(4-trifluoromethoxybenzyl)-2-thioxo-2,3-dihydrobenzimidazol-1-ylmethyl]phenyl}methanesulfonamide (8)

a. Synthesis of 1-(4-trifluoromethoxybenzyl)-1,3-dihydrobenzimidazol-2-one (R)

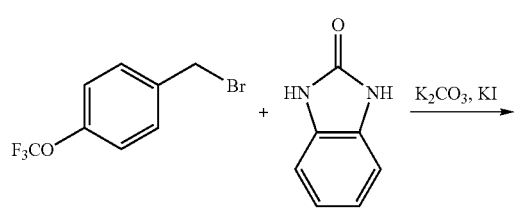

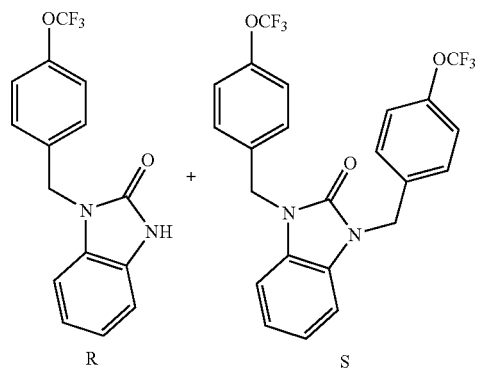

To a solution of benzimidazolinone (4.02 g, 30 mmol) in abs. DMF (20 mL) there were added 4-trifluoromethoxybenzyl bromide (5 g, 19.6 mmol), potassium carbonate (7.0 g, 50.7 mmol), and a catalytic amount of potassium iodide under a blanket of argon. The reaction mixture was heated to 100° C. over a period of 2 h. Following cooling, the reaction mixture was poured into a mixture of ice (200 g) and 2N hydrochloric acid solution in $H_2O$ (100 mL). The resulting precipitate was separated with the aid of a frit and then dried. The residue was taken up in EtOAc (150 mL) and the insoluble components separated. The solvent was removed in vacuo, and the residue was recrystallized from a little EtOAc (20 mL), and the dibenzylated product (S) was precipitated. The mother liquor was again concentrated in vacuo, the residue recrystallized from ethanol, and the precipitated solid matter (S) separated by filtration. The filtrate was purified by means of column chromatography ($SiO_2$, cyclohexane/EtOAc 1:4), and there was obtained 1-(4-trifluoromethoxybenzyl)-1,3-dihydrobenzimidazol-2-one (R) (1.60 mg, 26% of theory, mp: 145-148° C.).

b. Synthesis of 1-(4-nitrobenzyl)-3-(4-trifluoromethoxybenzyl)-1,3-dihydrobenzimidazol-2-one (T)

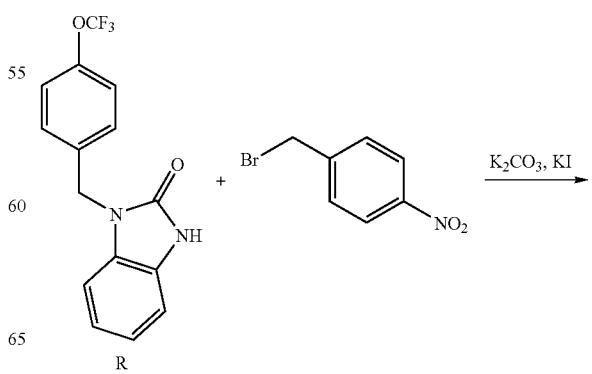

-continued

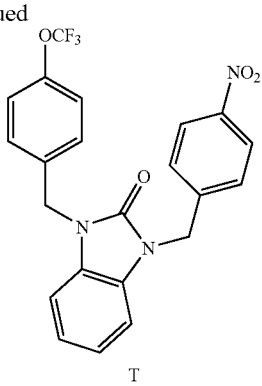

T

To a solution of compound R (770 mg, 2.5 mmol) in abs. DMF (20 mL) there were added 4-nitrobenzyl bromide (540 mg, 2.5 mmol), potassium carbonate (828 mg, 6 mmol), and a catalytic amount of potassium iodide under a blanket of argon. The reaction mixture was heated to from 80° to 85° C. over a period of 5 h. Following cooling, the reaction mixture was poured into a mixture of ice (200 g) and 2N hydrochloric acid solution in H$_2$O (10 mL), and the reaction mixture was stirred for 1 hour. The resulting solid matter was separated through a frit and recrystallized from ethanol (20 mL). The desired product 1-(4-nitrobenzyl)-3-(4-trifluoromethoxybenzyl)-1,3-dihydrobenzimidazol-2-one (T) was obtained in a yield of 830 g (74% of theory).

c. Synthesis of 1-(4-aminobenzyl)-3-(4-trifluoromethoxybenzyl)-1,3-dihydrobenzimidazol-2-one (U)

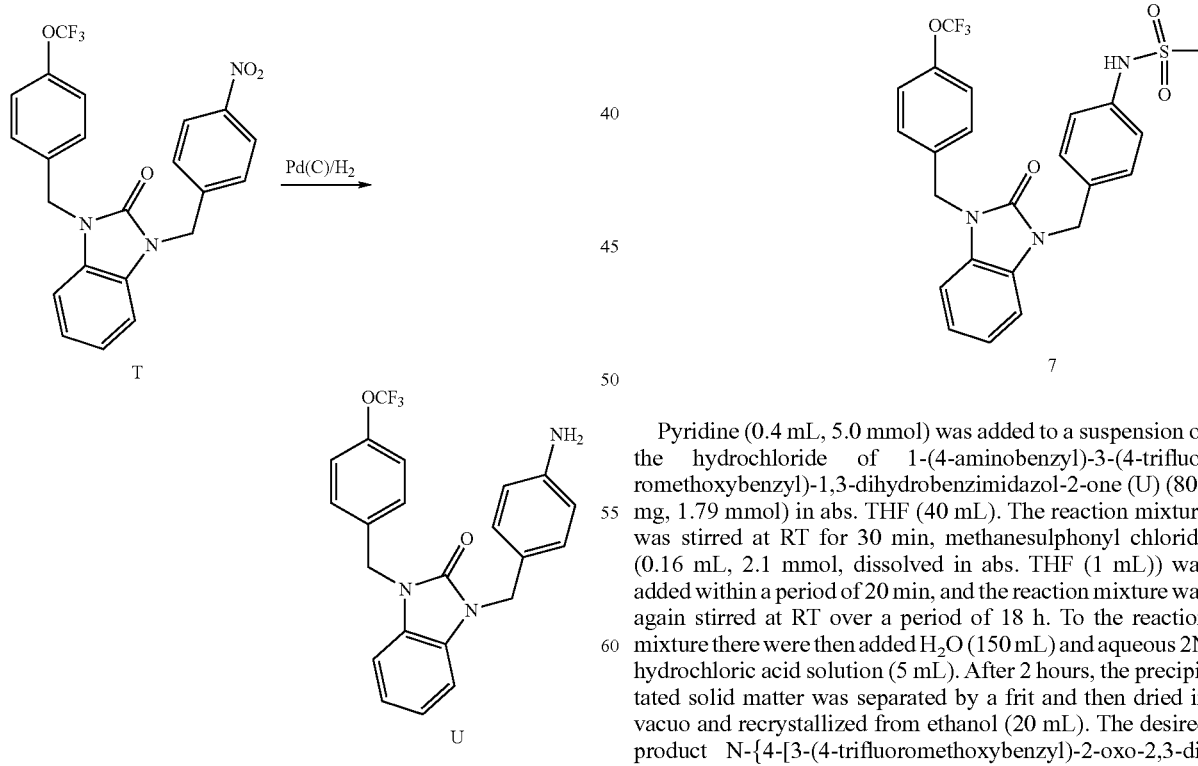

Palladium-on-charcoal (5%, 830 mg) was added to a solution of 1-(4-nitrobenzyl)-3-(4-trifluoromethoxybenzyl)-1,3-dihydrobenzimidazol-2-one (T) (1.00 g, 2.26 mmol) in abs. MeOH (200 mL). The reaction mixture was subjected to a hydrogen pressure of 3 bar for 30 min at RT. The catalyst was separated by filtration through a filter, and the filtrate was concentrated in vacuo. The residue was taken up in DCM (20 mL) and filtered through a frit with kieselguhr (layer thickness 1 cm). The frit was washed with DCM (3×20 mL). To the resulting solution there was added chlorotrimethylsilane (1 mL, 7.9 mmol). The reaction mixture was stirred over a period of 17 h without exclusion of moisture, and the precipitated solid matter was separated with the aid of a frit and then dried. The hydrochloride of 1-(4-aminobenzyl)-3-(4-trifluoromethoxybenzyl)-1,3-dihydrobenzimidazol-2-one (U) was obtained as solid matter (791 mg, 76% of theory, mp: 222-232° C.).

d. Synthesis of N-{4-[3-(4-trifluoromethoxybenzyl)-2-oxo-2,3-dihydrobenzimidazol-1-ylmethyl]phenyl}methanesulfonamide (7)

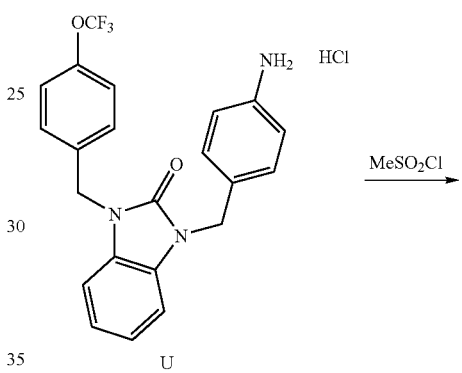

Pyridine (0.4 mL, 5.0 mmol) was added to a suspension of the hydrochloride of 1-(4-aminobenzyl)-3-(4-trifluoromethoxybenzyl)-1,3-dihydrobenzimidazol-2-one (U) (806 mg, 1.79 mmol) in abs. THF (40 mL). The reaction mixture was stirred at RT for 30 min, methanesulphonyl chloride (0.16 mL, 2.1 mmol, dissolved in abs. THF (1 mL)) was added within a period of 20 min, and the reaction mixture was again stirred at RT over a period of 18 h. To the reaction mixture there were then added H$_2$O (150 mL) and aqueous 2N hydrochloric acid solution (5 mL). After 2 hours, the precipitated solid matter was separated by a frit and then dried in vacuo and recrystallized from ethanol (20 mL). The desired product N-{4-[3-(4-trifluoromethoxybenzyl)-2-oxo-2,3-dihydrobenzimidazol-1-ylmethyl]phenyl}methanesulfonamide (70) was obtained in a yield of 505 mg (57% of theory, mp: 182-187° C.).

e. Synthesis of N-{4-[3-(4-trifluoromethoxybenzyl)-2-thioxo-2,3-dihydrobenzimidazol-1-ylmethyl]phenyl}methanesulfonamide (8)

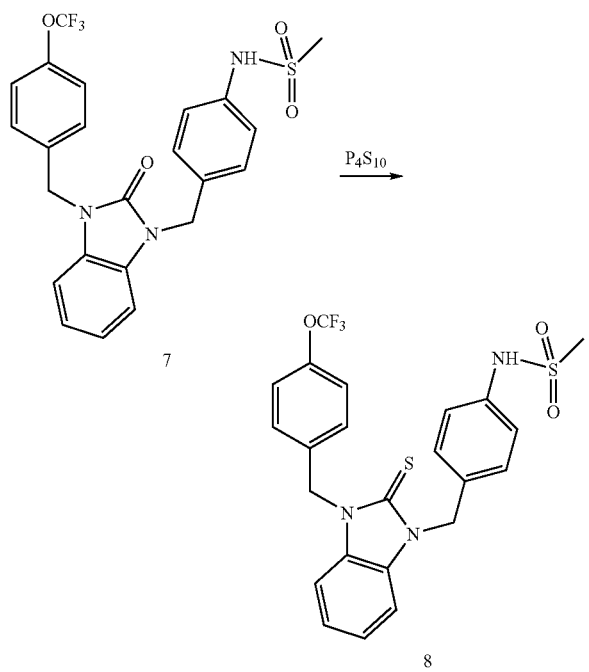

Phosphorus pentasulfide (444 mg, 1.0 mmol) was added to a suspension of N-{4-[3-(4-trifluoromethoxybenzyl)-2-oxo-2,3-dihydrobenzimidazol-1-ylmethyl]phenyl}methanesulfonamide (7) (300 mg, 0.61 mmol) in para-xylene (20 mL) under a blanket of argon. The reaction mixture was heated to the boil over a period of 10 h. Following cooling, there was added to the reaction mixture water (1 mL) followed by 2N NaOH solution in water (10 mL), and the mixture was stirred at RT for 30 min. The reaction mixture was extracted with ethyl acetate (4×20 mL). The combined organic phases were dried over $Na_2SO_4$ and the solvent removed in vacuo. After purifying the residue by means of column chromatography ($SiO_2$; cyclohexane/EtOAc 2:1), the desired product N-{4-[3-(4-trifluoromethoxybenzyl)-2-thioxo-2,3-dihydrobenzimidazol-1-ylmethyl]phenyl}methanesulfonamide (8) (162 mg, 52% of theory, mp: 167-170° C.) was obtained. After recrystallizing from methanol, there were obtained crystals having a melting point of 175-179° C.

VI. Synthesis of exemplary compound 9: N-{4-[3-(4-methanesulfonylaminobenzyl)-2-oxo-2,3-dihydrobenzimidazol-1-ylmethyl]phenyl}methanesulfonamide a. Synthesis of 1,3-bis(4-nitrobenzyl)-1,3-dihydrobenzimidazol-2-one (V)

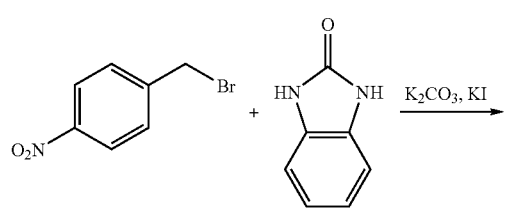

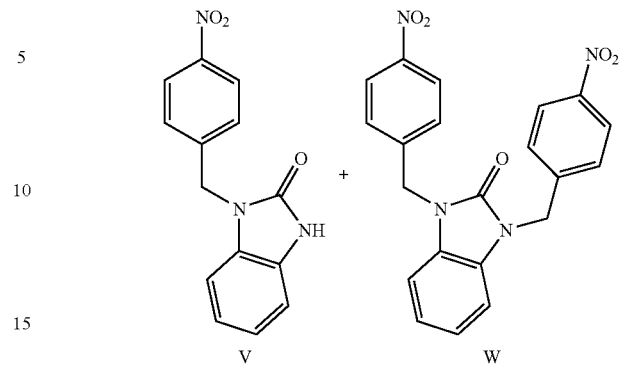

To a solution of benzimidazolinone (1.5 g, 11.2 mmol) in abs. DMF (25 mL) there were added 4-nitrobenzyl bromide (2.16 g, 10 mmol), potassium carbonate (2.76 g, 20 mmol), and a catalytic amount of potassium iodide under a blanket of argon. The reaction mixture was heated to 100° C. over a period of 2 h. Following cooling, the reaction mixture was poured into a solution of $H_2O$ (200 mL) and 2N hydrochloric acid solution in $H_2O$ (10 mL). The resulting mixture was extracted with EtOAc (5×40 mL), the combined organic phases were washed with sat. NaCl solution (2×30 mL), dried over $Na_2SO_4$, and the solvent was removed in vacuo. The residue was taken up in hot toluene (100 mL), and the resulting solid matter was isolated by filtration. The filtrate was concentrated in vacuo. The residue was purified by means of column chromatography ($SiO_2$, cyclohexane/EtOAc 1:1), and there were obtained 1,3-bis(4-nitrobenzyl)-1,3-dihydrobenzimidazol-2-one (W) (1.65 g, mp: 200-201° C.) and 1-(4-nitrobenzyl)-1,3-dihydrobenzimidazol-2-one (V) (600 mg, 22% of theory).

b. Synthesis of 1,3-bis-4-(4-aminobenzyl)-1,3-dihydrobenzimidazol-2-one (X)

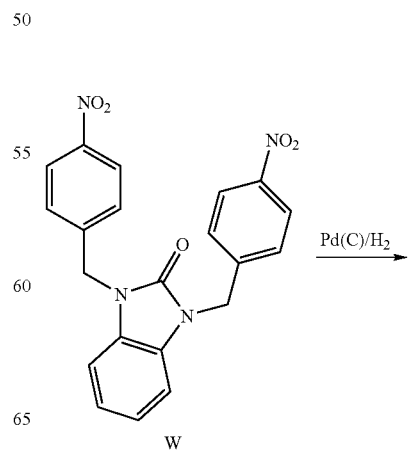

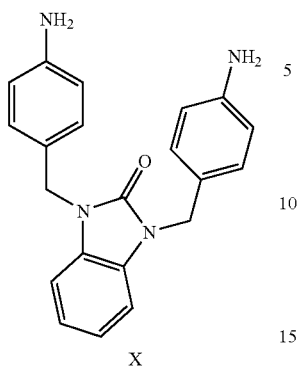

X

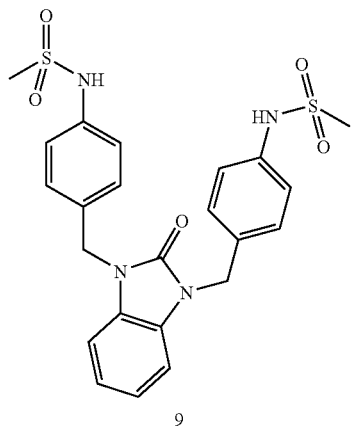

9

Palladium-on-charcoal (5%, 1.2 g) was added to a solution of bis-1,3-(4-nitrobenzyl)-1,3-dihydrobenzimidazol-2-one (W) (1.00 g, 2.4 mmol) in abs. THF (50 mL). The reaction mixture was subjected to a hydrogen pressure of 2 bar for 30 min at RT. The catalyst was separated by filtration through Celite and the filtrate was concentrated in vacuo. The desired product of 1,3-bis-4-(4-aminobenzyl)-1,3-dihydrobenzimidazol-2-one (X) was obtained as a colorless oil in a yield of 840 mg (99% of theory). For preparation of the corresponding dihydrochloride, chlorotrimethylsilane (184 mL, 1.5 mmol) was added to the compound (X) (200 mg, 0.58 mmol) in DCM (10 mL). The reaction mixture was stirred over a period of 17 h without exclusion of moisture, and the precipitated solid matter was separated with the aid of a frit and then dried. The dihydrochloride of 1,3-bis-4-(4-aminobenzyl)-1,3-dihydrobenzimidazol-2-one (x0) was obtained as solid matter (188 mg, 77% of theory, mp: 212-218° C.).

Triethylamine (0.63 mL, 4.55 mmol) was added to a suspension of the dihydrochloride of 1,3-bis-4-(4-aminobenzyl)-1,3-dihydrobenzimidazol-2-one (x0) (600 mg, 1.75 mmol) in abs. THF (50 mL). The reaction mixture was stirred at RT for 30 min, methanesulphonyl chloride (0.32 mL, 4.2 mmol, dissolved in abs. THF (10 mL)) was added within a period of 15 min, and the reaction mixture was again stirred at RT over a period of 48 h. H$_2$O (150 mL) and sat. sodium hydrogen carbonate solution (30 mL) were then added to the reaction mixture, which was then stirred at RT for 30 min and extracted with EtOAc (3×20 mL). The combined organic phases were washed with sat. NaCl solution (30 mL), dried over Na$_2$SO$_4$, and the solvent was removed in vacuo. Following purification of the residue by means of column chromatography (SiO$_2$ (70 g), 700 mL cyclohexane/EtOAc 1:4), the desired product N-{4-[3-(4-methanesulfonylaminobenzyl)-2-oxo-2,3-dihydrobenzimidazol-1-ylmethyl]phenyl}methanesulfonamide (9) was obtained in a yield of 110 mg (12% of theory, mp: 204-214° C.).

c. Synthesis of N-{4-[3-(4-methanesulfonylaminobenzyl)-2-oxo-2,3-dihydrobenzimidazol-1-ylmethyl]phenyl}methanesulfonamide (9)

VII. Synthesis of exemplary compound 10: N-{4-[2-oxo-3-(4-trifluoromethylbenzyl)-2,3-dihydrobenzimidazol-1-ylmethyl]phenyl}methanesulfonamide a. Synthesis of 1-(4-trifluoromethylbenzyl)-1,3-dihydrobenzimidazol-2-one Y

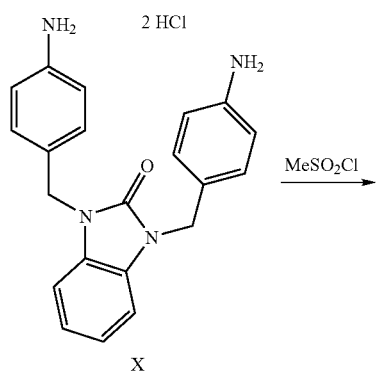

X

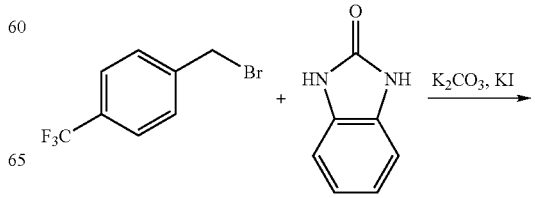

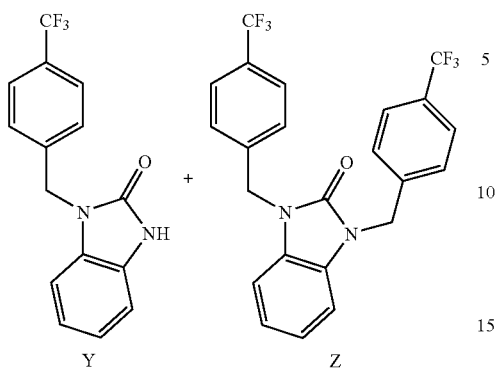

4 g, 16.7 mmol of potassium carbonate (7 g, 50.7 mmol) and a spatula tip of potassium iodide were added to a solution of 2-hydroxybenzimidazole (4 g, 29 mmol) in abs. DMF (40 mL) under a blanket of argon. The reaction mixture was heated to 100° C. (bath temperature) over a period of 5 h with stirring. Following cooling, the batch was added to a mixture of ice (200 g) and 2N HCl (50 mL). The resulting aqueous suspension was stirred for 30 min, and the resulting solid matter was separated by means of a frit, dried, and recrystallized from ethanol (100 mL). The disubstituted benzimidazole Z precipitated and the desired product remained predominantly in solution. In order to isolate Y, the ethanolic solution was concentrated. For removal of unconverted 2-hydroxybenzimidazole, the remaining residue was taken up in chloroform (approximately 50 mL) and the insoluble components were separated. The residue (1.7 g, 34%) resulting following evaporation of the solvent consisted to an extent of more than 90% of desired product 4C and could be used without further purification for the following conversion.

b. Synthesis of 1-(4-nitrobenzyl)-3-(4-trifluoromethylbenzyl)-1,3-dihydrobenzimidazol-2-one

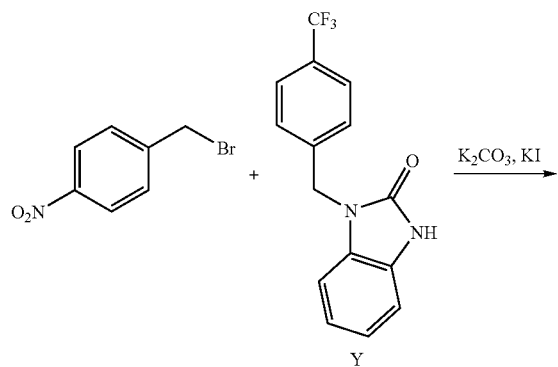

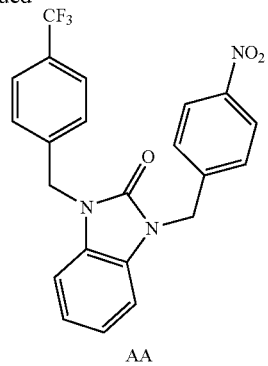

To a solution of the compound Y (876 mg, 3 mmol) in abs. DMF (30 mL) there were added 4-nitrobenzyl bromide (648 mg, 3 mmol), potassium carbonate (1.1 g, 8 mmol) and a spatula tip of potassium iodide under a blanket of argon. The reaction mixture was heated to 85° C. (bath temperature) over a period of 5 h with stirring. Following cooling, the batch was added to a mixture of ice (150 g) and aq. 2N HCl (20 mL). The solution was stirred at RT over a period of 1 h, and the resulting solid matter was separated by means of a frit and dried in vacuo over CaCl$_2$. The desired product was obtained from the crude product by recrystallization from ethanol (20 mL) in a yield of 700 mg (54%) and with a melting point of 134-137° C.

c. Synthesis of 4-[2-oxo-3-(4-trifluoromethylbenzyl)-2,3-dihydrobenzimidazol-1-ylmethyl]phenylammonium chloride

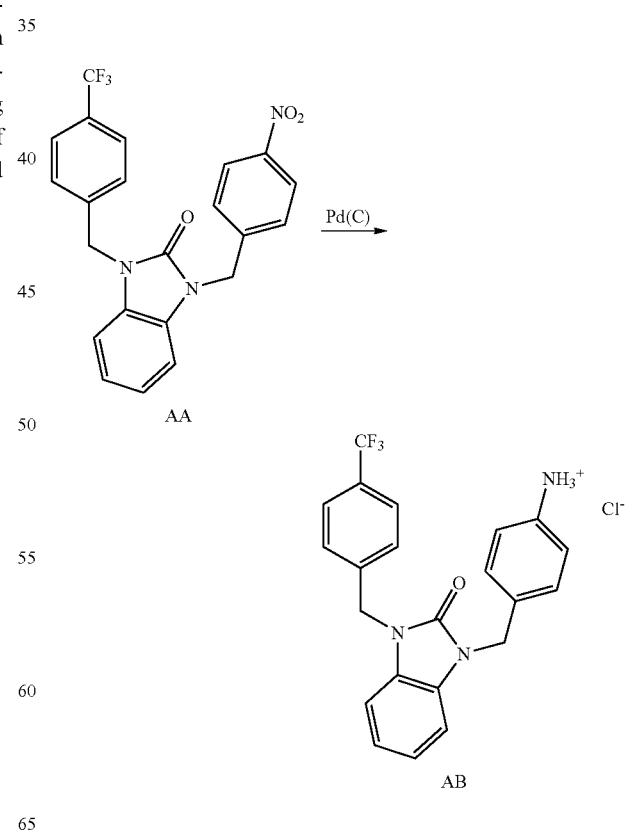

Palladium catalyst (5% of Pd on activated carbon, 420 mg) was added to a solution of compound AA (590 mg, 1.38 mmol) in methanol (100 mL), and the mixture was hydrogenated at RT under a pressure of 2 bar for 30 min. The catalyst was separated by filtration, and the resulting methanolic solution was concentrated to dryness. Following removal of the solvent, the crude product was obtained, which was dissolved in dichloromethane (30 mL). The solution was filtered, and the filtration residue was washed 2 times with $CH_2Cl_2$ (10 mL each time). To the resulting solution there was added chlorotrimethylsilane (0.5 mL, 4 mmol). The solution was stirred over a period of 5 h without exclusion of moisture, and the precipitated solid matter was separated by means of a frit and then dried. The desired product was thus obtained in a yield of 572 mg (95%) and had a melting point of 221-225° C.

d. Synthesis of N-{4-[2-oxo-3-(4-trifluoromethyl-benzyl)-2,3-dihydrobenzimidazol-1-ylmethyl]phenyl}methanesulfonamide

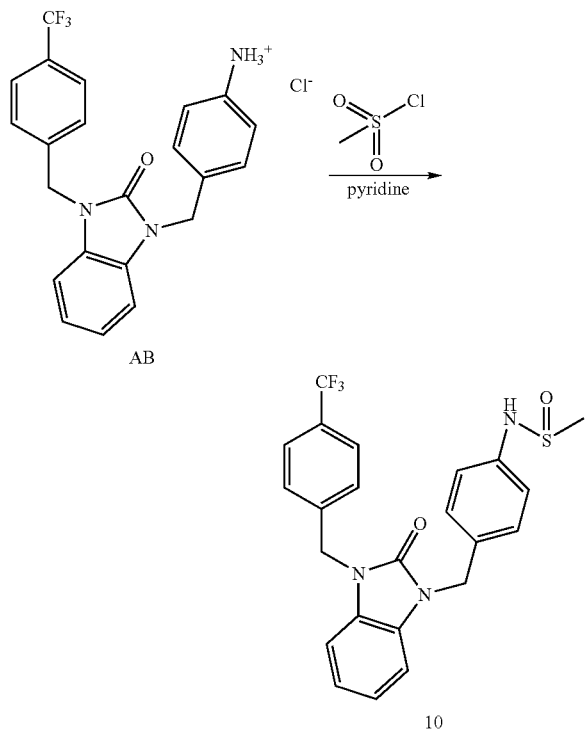

Pyridine (0.5 mL, 6.4 mmol) was added to a suspension of compound AB (700 mg, 1.6 mmol) in abs. dioxane (30 mL). The batch was heated to the boil until the hydrochloride was completely dissolved as free base. The batch was cooled to approximately 40° C., and to the clear solution there was then added methanesulphonyl chloride (0.2 mL, 2.6 mmol, dissolved in dry dioxane (1 mL)) within a period of 5 min. The reaction mixture was stirred at RT over a period of 2 d, and the dioxane was then removed in vacuo. Water (20 mL) was added to the residue, and the mixture was extracted with ethyl acetate (3×20 mL). The organic phases were dried over $Na_2SO_4$ and the solvent removed in vacuo. The residue was purified by column chromatography (mobile solvent: cyclohexane/ethyl acetate 1:1). The solvent was removed in vacuo and the residue recrystallized from ethanol (7 mL) to give the desired product in a yield of 150 mg (19%); melting point 193-197° C.

Pharmacological Data:

I.

The tested substituted cyclic urea derivatives of the invention show excellent affinity toward the Vanilloid receptor 1 (VR1/TRPV1 receptor).

| Compound of Example | $IC_{50}$ value [μM] |
|---|---|
| 4 | 9.4 |
| 5 | 2.9 |

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

The invention claimed is:

1. A cyclic urea compound corresponding to formula I,

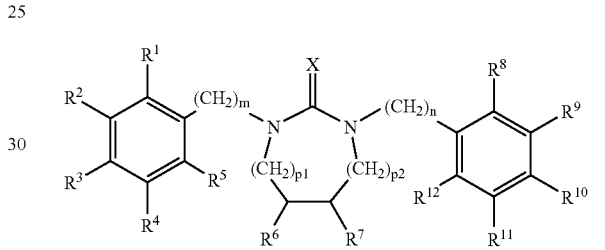

wherein
X stands for O, S or N—C≡N;
m is equal to 1 or 2;
n is equal to 1 or 2;
p1 and p2 independently stand for 0, 1, 2, or 3, the sum of p1 and p2 being 0, 1, 2, or 3;
$R^1$, $R^2$, $R^3$, $R^4$, $R^5$, $R^8$, $R^9$, $R^{10}$, $R^{11}$ and $R^{12}$ independently stand for H; F; Cl; Br; I; —$SF_5$; —$NO_2$; —$NH_2$; —OH; —SH; —C(=O)—$NH_2$; —S(=O)$_2$—$NH_2$; —$NR^{13}R^{14}$; —NH—$R^{15}$; —$OR^{16}$; —$SR^{17}$; —O—$(CH_2)_a$—$R^{18}$; —O—$(CH_2)_b$—$OR^{19}$; —$(CH_2)_c$—O—$(CH_2)_d$—$OR^{20}$; —$(CH_2)_e$—O—C(=O)—$R^{21}$; —$(CH_2)_f$—O—C(=O)—$OR^{22}$; —$NR^{23}S(=O)_2R^{24}$; —$(CH_2)_g$—C(=O)—$NR^{25}R^{26}$; —$(CH_2)_h$—C(=O)—NH—$R^{27}$; —S(=O)$_iR^{28}$; —$(CH_2)_j$—S(=O)$_2$—$NR^{29}R^{30}$; —$(CH_2)_k$—S(=O)$_2$—$NHR^{31}$; —$(CH_2)_l$—$NR^{32}$—C(=O)$(CH_2)_q$—$OR^{33}$; —$(CH_2)_r$—NH—C(=O)$(CH_2)_s$—$OR^{34}$; —$(CH_2)_t$—$NR^{35}$—O—C(=O)—$OR^{36}$; —$(CH_2)_u$—NH—O—C(=O)—$OR^{37}$; —$(CH_2)_v$—O—S(=O)$_2$—$R^{38}$; —$(CH_2)_w$—$NR^{39}$—C(=O)—$SR^{40}$; —$(CH_2)_y$—C(=O)—NH—$OR^{41}$; —P(=O)$(OR^{42})_2$; —$(CH_2)_z$—C(=S)—$NR^{43}R^{44}$; —$(CH_2)_{aa}$—C(=S)—NH—$R^{45}$; —$(CH_2)_{bb}$—$NR^{46}$—C(=O)—$R^{47}$; —$(CH_2)_{cc}$—NH—C(=O)—$R^{48}$;

or —NH—C(=NH)—NH$_2$;
with a, b, c, d, q and s independently standing for 1, 2, 3, 4, or 5, and e, f, g, h, j, k, l, r, t, u, v, w, x, y, z, aa, bb and cc independently standing for 0, 1, 2, 3, 4, or 5, and
i being equal to 1 or 2
or for a linear or branched, saturated or unsaturated aliphatic C$_{1-10}$ group, which can optionally be substituted by 1, 2, 3, 4, 5, 6, 7, 8, or 9 substituents independently selected from the group consisting of F, Cl, Br, I, —CN, —NO$_2$, —OH, —NH$_2$, —SH, —O(C$_{1-5}$ alkyl), —S(C$_{1-5}$ alkyl), —NH(C$_{1-5}$ alkyl), —N(C$_{1-5}$ alkyl)(C$_{1-5}$ alkyl), —OCF$_3$ and —SCF$_3$;
or for an optionally substituted six-membered or ten-membered aryl group, which may be bonded via a linear or branched, optionally substituted C$_{1-5}$ alkylene group;
or two adjacent members selected from the group consisting of R$^8$, R$^9$, R$^{10}$, R$^{11}$ and R$^{12}$ together stand for a methylenedioxy(—O—CH$_2$—O) group;
provided that at least one of R$^8$, R$^9$, R$^{10}$, R$^{11}$, and R$^{12}$ is —NR$^{23}$S(=O)$_2$R$^{24}$;
R$^6$ and R$^7$ are each hydrogen, or
R$^6$ and R$^7$, together with the interconnecting C—C bridge, form an unsubstituted phenylene group;
R$^{13}$, R$^{14}$, R$^{15}$, R$^{16}$, R$^{17}$, R$^{19}$, R$^{20}$, R$^{21}$, R$^{22}$, R$^{25}$, R$^{26}$, R$^{27}$, R$^{28}$, R$^{29}$, R$^{30}$, R$^{31}$, R$^{32}$, R$^{33}$, R$^{34}$, R$^{35}$, R$^{36}$, R$^{37}$, R$^{38}$, R$^{39}$, R$^{40}$, R$^{41}$, R$^{42}$, R$^{43}$, R$^{44}$, R$^{45}$, R$^{46}$, R$^{47}$ and R$^{48}$ independently stand for a linear or branched, saturated or unsaturated aliphatic C$_{1-10}$ group, which may be substituted by 1, 2, 3, 4, 5, 6, 7, 8, or 9 substituents independently selected from the group consisting of F, Cl, Br, I, —CN, —NO$_2$, —OH, —NH$_2$, —SH, —O(C$_{1-5}$ alkyl), —S(C$_{1-5}$ alkyl), —NH(C$_{1-5}$ alkyl), —N(C$_{1-5}$ alkyl)(C$_{1-5}$ alkyl), —OCF$_3$, and —SCF$_3$;
or for an unsaturated or saturated, optionally substituted three-membered, four-membered, five-membered, six-membered, seven-membered, eight-membered, or nine-membered cycloaliphatic group, or for an optionally substituted five-membered to fourteen-membered aryl group or an optionally substituted five-membered to fourteen-membered heteroaryl group, which may be condensed with a saturated or unsaturated, optionally substituted monocyclic or polycyclic ring system;
R$^{18}$ stands for an unsaturated or saturated, optionally substituted three-membered, four-membered, five-membered, six-membered, seven-membered, eight-membered, or nine-membered cycloaliphatic group or for an optionally substituted five-membered to fourteen-membered aryl group or an optionally substituted five-membered to fourteen-membered heteroaryl group, which may be condensed with a saturated or unsaturated, optionally substituted monocyclic or polycyclic ring system;
R$^{23}$ is hydrogen or a linear or branched, saturated or unsaturated or aliphatic C$_{1-10}$ group, which may be substituted by 1, 2, 3, 4, 5, 6, 7, 8, or 9 substituents independently selected from the group consisting of F, Cl, Br, I, —CN, —NO$_2$, —OH, —NH$_2$, —SH, —O(C$_{1-5}$ alkyl), —S(C$_{1-5}$ alkyl), —NH(C$_{1-5}$ alkyl), —N(C$_{1-5}$ alkyl)(C$_{1-5}$ alkyl), —OCF$_3$, and —SCF$_3$;
and
R$^{24}$ stands for a linear or branched, saturated or unsaturated or aliphatic C$_{1-10}$ group, which may be substituted by 1, 2, 3, 4, or 5 substituents independently selected from the group consisting of —CN, —NO$_2$, —OH, —NH$_2$, —SH, —O(C$_{1-5}$ alkyl), —S(C$_{1-5}$ alkyl), —NH(C$_{1-5}$ alkyl), and —N(C$_{1-5}$ alkyl)(C$_{1-5}$ alkyl),
or for an optionally substituted 5-membered to 14-membered aryl or heteroaryl group, which may be condensed with a saturated or unsaturated, optionally substituted mono- or polycyclic ring system;
wherein
the aforementioned cycloaliphatic groups may, in each case, be substituted by 1, 2, 3, 4, or 5 substituents independently selected from the group consisting of oxo (=O), thioxo (=S), F, Cl, Br, I, —CN, —CF$_3$, —SF$_3$, —OH, —O—C$_{1-5}$ alkyl, —NH$_2$, —NO$_2$, —O—CF$_3$, —S—CF$_3$, —SH, —S—C$_{1-5}$ alkyl, —C$_{1-5}$ alkyl, —C(=O)—OH, —C(=O)—O—C$_{1-5}$ alkyl, —NH—C$_{1-5}$ alkyl, —N(C$_{1-5}$ alkyl)$_2$, —O-phenyl, —O-benzyl, phenyl, and benzyl, and in each case the cyclic moiety of the groups —O-phenyl, —O-benzyl, phenyl, and benzyl may be substituted by 1, 2, 3, 4, or 5 substituents independently selected from the group consisting of F, Cl, Br, —OH, —CF$_3$, —SF$_5$, —CN, —NO$_2$, —C$_{1-5}$ alkyl, —O—C$_{1-5}$ alkyl, —O—CF$_3$, —S—CF$_3$, phenyl, and —O-benzyl,
the aforementioned cycloaliphatic groups in each case may exhibit 1, 2, 3, 4, or 5 heteroatoms independently selected from the group consisting of oxygen, nitrogen, and sulfur;
the aforementioned C$_{1-5}$ alkylene group may optionally be substituted by 1, 2, 3, 4, or 5 substituents independently selected from the group consisting of F, Cl, Br, —OH, —SH, —NH$_2$, —CN, and NO$_2$;
the rings of the aforementioned monocyclic or polycyclic ring systems may, in each case, be substituted by 1, 2, 3, 4, or 5 substituents independently selected from the group consisting of oxo (=O), thioxo (=S), F, Cl, Br, I, —CN, —CF$_3$, —SF$_5$, —OH, —O—C$_{1-5}$ alkyl, —NH$_2$, —NO$_2$, —O—CF$_3$, —S—CF$_3$, —SH, —S—C$_{1-5}$ alkyl, —C$_{1-5}$ alkyl, —C(=O)—OH, —C(=O)—O—C$_{1-5}$ alkyl, —NH—C$_{1-5}$ alkyl, —N(C$_{1-5}$ alkyl)$_2$, —O-phenyl, —O-benzyl, phenyl, and benzyl, and in each case the cyclic moiety of the groups —O-phenyl, —O-benzyl, phenyl, and benzyl may be substituted by 1, 2, 3, 4, or 5 substituents independently selected from the group consisting of F, Cl, Br, —OH, —CF$_3$, —SF$_5$, —CN, —NO$_2$, —C$_{1-5}$ alkyl, —O—C$_{1-5}$ alkyl, —O—CF$_3$, —S—CF$_3$, phenyl, and —O-benzyl;
the rings of the aforementioned monocyclic or polycyclic ring systems are each five-membered, six-membered, or seven-membered and may, in each case, optionally exhibit 1, 2, 3, 4, or 5 heteroatoms as ring members, which are independently selected from the group consisting of oxygen, nitrogen, and sulfur;
the aforementioned aryl or heteroaryl groups may, in each case, be substituted by 1, 2, 3, 4, or 5 substituents independently selected from the group consisting of F, Cl, Br, I, —CN, —CF$_3$, —SF$_5$, —OH, —O—C$_{1-5}$ alkyl, —NH$_2$, —NO$_2$, —O—CF$_3$, —S—CF$_3$, —SH, —S—C$_{1-5}$ alkyl, —C$_{1-5}$ alkyl, —C(=O)—OH, —C(=O)—O—C$_{1-5}$ alkyl, —NH—C$_{1-5}$ alkyl, —N(Cl$_{1-5}$ alkyl)$_2$, —NH—C(=O)—O—C$_{1-5}$ alkyl, —C(=O)—H, —C(=O)—C$_{1-5}$ alkyl, —C(=O)—NH$_2$, —C(=O)—NH—C$_{1-5}$ alkyl, —C(=O)—N—(C$_{1-5}$ alkyl)$_2$, —O-phenyl, —O-benzyl, phenyl, and benzyl, and in each case the cyclic moiety of the groups —O-phenyl, —O-benzyl, phenyl, and benzyl may be substituted by 1, 2, 3, 4, or 5 substituents independently selected from the group consisting of F, Cl, Br, —OH, —CF$_2$, —SF$_{1-5}$, —CN, —NO$_{1-5}$, —C$_3$ alkyl, —O—C$_3$ alkyl, —O—CF$_3$, —S—CF$_3$, phenyl, and —O-benzyl, and the aforementioned heteroaryl groups in each case comprise 1, 2, 3, 4, or 5 heteroatom independently selected from the group consisting of oxygen, nitrogen, optionally in the form of an isolated enantiomer or isolated diastereomer or a mixture of stereoisomers and sulfur as ring members;

or a physiologically acceptable salt thereof.

2. The compound of claim 1, wherein said compound is present in the form of an isolated enantiomer or isolated diastereoisomer or a racemic mixture.

3. The compound of claim 1, wherein said compound is present in the form of a mixture of stereoisomers.

4. A compound according to claim 1, wherein $R^1$, $R^2$, $R^4$, and $R^5$ each independently represent H; F; Cl; Br; I; —SF$_5$; —NO$_2$; —NH$_2$;
—OH; —SH; —C(=O)—NH$_2$; —S(=O)$_2$—NH$_2$; —NR$^{13}$R$^{14}$; —NH—R$^{15}$; —OR$^{16}$; —SR$^{17}$; —O—(CH$_2$)$_a$—R$^{18}$; —O—(CH$_2$)$_b$—OR$^{19}$;
—(CH$_2$)$_c$—O—(CH$_2$)$_d$—OR$^{20}$;
—(CH$_2$)$_e$—O—C(=O)—R$^{21}$;
—(CH$_2$)$_f$—O—C(=O)—OR$^{22}$;
—NR$^{23}$S(=O)$_2$R$^{24}$;
—(CH$_2$)$_g$—C(=O)—NR$^{25}$R$^{26}$;
—(CH$_2$)$_h$—C(=O)—NH—R$^{27}$;
—S(=O)$_i$R$^{28}$;
—(CH$_2$)$_j$—S(=O)$_2$—NR$^{29}$R$^{30}$;
—(CH$_2$)$_k$—S(=O)$_2$—NHR$^{31}$;
—(CH$_2$)$_l$—NR$^{32}$—C(=O)(CH$_2$)$_q$—OR$^{33}$;
—(CH$_2$)$_r$—NH—C(=O)(CH$_2$)$_s$—OR$^{34}$;
—(CH$_2$)$_t$—NR$^{35}$—O—C(=O)—OR$^{36}$;
—(CH$_2$)$_u$—NH—O—C(=O)—OR$^{37}$;
—(CH$_2$)$_v$—O—S(=O)$_2$—R$^{38}$;
—(CH$_2$)$_w$—NR$^{39}$—C(=O)—SR$^{40}$;
—(CH$_2$)$_y$—C(=O)—NH—OR$^{41}$;
—P(=O)(OR$^{42}$)$_2$;
—(CH$_2$)$_z$—C(=S)—NR$^{43}$R$^{44}$;
—(CH$_2$)$_{aa}$—C(=S)—NH—R$^{45}$;
—(CH$_2$)$_{bb}$—NR$^{46}$—C(=O)—R$^{47}$;
—(CH$_2$)$_{cc}$—NH—C(=O)—R$^{48}$;
or —NH—C(=NH)—NH$_2$;

with a, b, and c, d, q and s each being independently equal to 1, 2, 3, 4, or 5, e, f, and g, h, j, k, l, r, t, u, v, w, x, y, and z, aa, bb and cc each being independently equal to 1, 1, 2, 3, 4, or 5 and i being equal to 1 or 2;

or a member selected from the group consisting of methyl, —CF$_3$, —CCl$_3$, —CBr$_3$, —CH$_2$—CN, —CH$_2$—O—CH$_3$, —CH$_2$—O—CF$_3$, —CH$_2$SCF$_3$, —CH$_2$—NH$_2$, —CH$_2$—OH, —CH$_2$—SH, —CH$_2$—NH—CH$_3$, —CH$_2$—N(CH$_3$)$_2$, —CH$_2$—N(C$_2$H$_5$)$_2$, —CH$_2$—N(CH$_3$)(C$_2$H$_5$), ethyl, —CH$_2$—CH$_2$—NH$_2$, —CH$_2$—CH$_2$—OH, —CH$_2$—CH$_2$—SH, —CH$_2$—CH$_2$—NH—CH$_3$, —CH$_2$—CH$_2$—N(CH$_3$)$_2$, —CH$_2$—CH$_2$—N(C$_2$H$_5$)$_2$, —CH$_2$—CH$_2$—N(CH$_3$)(C$_2$H$_5$), —CH$_2$—CF$_3$, —C$_2$F$_5$, —CH$_2$—CCl$_3$, —CH$_2$—CBr$_3$, —CH$_2$—CH$_2$—CN, n-propyl, —CH$_2$—CH$_2$—CH$_2$—OH, —CH$_2$—CH$_2$—CH$_2$—SH, —CH$_2$—CH$_2$—CH$_2$—NH$_2$, —CH$_2$—CH$_2$—CH$_2$—NH—CH$_3$, —CH$_2$—CH$_2$—CH$_2$—N(CH$_3$)$_2$, —CH$_2$—CH$_2$—CH$_2$—N(C$_2$H$_5$)$_2$, —CH$_2$—CH$_2$—CH$_2$—N(CH$_3$)(C$_2$H$_5$), —CH$_2$—CH$_2$—O—CH$_3$, —CF$_2$—CF$_2$—CF$_3$, —CF(CF$_3$)$_2$, isopropyl, —CH$_2$—CH$_2$—CH$_2$—CN, —CH$_2$—O—CH$_2$—CH$_3$, —CH$_2$—CH$_2$—SCF$_2$, —CH$_2$—CH$_2$—OCF$_3$, —CH(CH$_3$)(O—CH$_3$), —CH(CH$_3$)(S—CH$_3$), n-butyl, —CF$_2$—CF$_2$—CF$_2$—CF$_3$, —CH$_2$—CH$_2$—CH$_2$—CH$_2$—CN, sec-butyl, isobutyl, tert-butyl, n-pentyl, sec-pentyl, neopentyl, n-hexyl, vinyl, 1-propenyl, 2-propenyl, 1-butenyl, 2-butenyl, 3-butenyl, 2-methylbuten-2-yl, (1,1,2)-trifluoro-1-butenyl, 1-pentenyl, 2-pentenyl, 3-pentenyl, and 4-pentenyl;

or an aryl group selected from the group consisting of phenyl and naphthyl, wherein the aryl group may be substituted by 1, 2, 3, 4, or 5 substituents independently selected from the group consisting of F, Cl, Br, I, —CN, —NO$_2$, —OH, —SH, methyl, ethyl, —CF$_3$, —O—CF$_3$, —S—CF$_3$, —SF$_5$, —O—CH$_3$, —O—C$_2$H$_5$, —NH$_2$, —N(CH$_3$)$_2$, —N(C$_2$H$_5$)$_2$, —N(H)(CH$_3$), and —N(H)(C$_2$H$_5$); and $R^3$ represents F; Cl; Br; I; —SF$_5$; —NO$_2$; —NH$_2$; —OH; —SH; —C(=O)—NH$_2$; —S(=O)$_2$—NH$_2$; —NR$^{13}$R$^{14}$; —NH—R$^{15}$; —OR$^{16}$; —SR$^{17}$; —O—(CH$_2$)$_a$—R$^{18}$, —O—(CH$_2$)$_b$—OR$^{19}$, or —NR$^{23}$S(=O)$_2$R$^{24}$; wherein a and b are each independently equal to 1, 2, 3, 4, or 5;

or a member selected from the group consisting of methyl, —CF$_3$, —CCl$_3$, —CBr$_3$, —CH$_2$—CN, —CH$_2$—O—CH$_3$, —CH$_2$—O—CF$_3$, —CH$_2$—SCF$_3$, —CH$_2$—NH$_2$, —CH$_2$—OH, —CH$_2$—SH, —CH$_2$—NH—CH$_3$, —CH$_2$—N(CH$_3$)$_2$, —CH$_2$—N(C$_2$H$_5$)$_2$, —CH$_2$—N(CH$_3$)(C$_2$H$_5$), ethyl, —CH$_2$—CH$_2$—NH$_2$, —CH$_2$—CH$_2$—OH, —CH$_2$—CH$_2$—SH, —CH$_2$—CH$_2$—NH—CH$_3$, —CH$_2$—CH$_2$—N(CH$_3$)$_2$, —CH$_2$—CH$_2$—N(C$_2$H$_5$)$_2$, —CH$_2$—CH$_2$—N(CH$_3$)(C$_2$H$_5$), —CH$_2$—CF$_3$, —C$_2$F$_5$, —CH$_2$—CCl$_3$, —CH$_2$—CBr$_3$, —CH$_2$—CH$_2$—CN, n-propyl, —CH$_2$—CH$_2$—CH$_2$—OH, —CH$_2$—CH$_2$—SH, —CH$_2$—CH$_2$—CH$_2$—NH$_2$, —CH$_2$—CH$_2$—CH$_2$—NH—CH$_3$, —CH$_2$—CH$_2$—CH$_2$—N(CH$_3$)$_2$, —CH$_2$—CH$_2$—CH$_2$—N(C$_2$H$_5$)$_2$, —CH$_2$—CH$_2$—CH$_2$—N(CH$_3$)(C$_2$H$_5$), —CH$_2$—CH$_2$—O—CH$_3$, —CF$_2$—CF$_2$—CF$_3$, —CF(CF$_3$)$_2$, isopropyl, —CH$_2$—CH$_2$—CH$_2$—CN, —CH$_2$—O—CH$_2$—CH$_3$, —CH$_2$—CH$_2$—SCF$_2$, —CH$_2$—CH$_2$—OCF$_3$, —CH(CH$_3$)(O—CH$_3$), —CH(CH$_3$)(S—CH$_3$), n-butyl, —CF$_2$—CF$_2$—CF$_2$—CF$_3$, —CH$_2$—CH$_2$—CH$_2$—CH$_2$—CN, sec-butyl, isobutyl, tert-butyl, n-pentyl, sec-pentyl, neopentyl, n-hexyl, vinyl, 1-propenyl, 2-propenyl, 1-butenyl, 2-butenyl, 3-butenyl, 2-methylbuten-2-yl, (1,1,2)-trifluoro-1-butenyl, 1-pentenyl, 2-pentenyl, 3-pentenyl, and 4-pentenyl.

5. A compound according to claim 1, wherein $R^1$, $R^2$, $R^4$, and $R^5$ each independently represent H; F; Cl; I; Br; —NO$_2$; —NH$_2$; —OH; and —SH; —NR$^{13}$R$^{14}$; —NH—R$^{15}$; —OR$^{16}$; —SR$^{17}$; —NR$^{23}$S(=O)$_2$R$^{24}$;

or a member selected from the group consisting of methyl, —CF$_3$, ethyl, —CH$_2$—CF$_3$, n-propyl, isopropyl, n-butyl, sec-butyl, isobutyl, tert-butyl, or n-pentyl, and $R^3$ represents F; Cl; Br; I; —OR$^2$; —NR$^{23}$S(=O)$_2$R$^{24}$;

or a member selected from the group consisting of —SF$_5$, —CF$_3$, —C$_2$F$_5$, —CH$_2$—CF$_3$, —CF(CF$_3$)$_2$, isopropyl, —CH(CH$_3$)(O—CH$_3$), —CH(CH$_3$)(S—CH$_s$), sec-butyl, isobutyl, and tert-butyl.

6. A compound according to claim 1, wherein $R^8$, $R^9$, $R^{11}$, and $R^{12}$ each independently represent H; F; Cl; Br; I; —SF$_5$; —NO$_2$;
—NH$_2$; —OH; —SH; —C(=O)—NH$_2$; —S(=O)$_2$—NH$_2$;

—NR$^{13}$R$^{14}$; —NH—R$^{15}$; —OR$^{16}$; —SR$^{17}$; —O—(CH$_2$)$_a$—R$^{18}$; —O—(CH$_2$)$_b$—OR$^{19}$;
—(CH$_2$)$_c$—O—(CH$_2$)$_d$—OR$^{20}$;
—(CH$_2$)$_e$—O—C(=O)—R$^{21}$;
—(CH$_2$)$_f$—O—C(=O)—OR$^{22}$;
—NR$^{23}$S(=O)$_2$R$^{24}$;
—(CH$_2$)$_g$—C(=O)—NR$^{25}$R$^{26}$;
—(CH$_2$)$_h$—C(=O)—NH—R$^{27}$;
—S(=O)$_i$R$^{28}$;
—(CH$_2$)$_j$—S(=O)$_2$—NR$^{29}$R$^{30}$;
—(CH$_2$)$_k$—S(=O)$_2$—NHR$^{31}$;
—(CH$_2$)$_l$—NR$^{32}$—C(=O)(CH$_2$)$_q$—OR$^{33}$;
—(CH$_2$)$_r$—NH—C(=O)(CH$_2$)$_s$—OR$^{34}$;
—(CH$_2$)$_t$—NR$^{35}$—O—C(=O)—OR$^{36}$;
—(CH$_2$)$_u$—NH—O—C(=O)—OR$^{37}$;
—(CH$_2$)$_v$—O—S(=O)$_2$—R$^{38}$;
—(CH$_2$)$_w$—NR$^{39}$—C(=O)—SR$^{40}$;
—(CH$_2$)$_y$—C(=O)—NH—OR$^{41}$;
—P(=O) (OR$^{42}$)$_2$;
—(CH$_2$)$_z$—C(=S)—NR$^{43}$R$^{44}$;
—(CH$_2$)$_{aa}$—C(=S)—NH—R$^{45}$;
—(CH$_2$)$_{bb}$—NR$^{46}$—C(=O)—R$^{47}$;
—(CH$_2$)$_{cc}$—NH—C(=O)—R$^{48}$;
or —NH—C(=NH)—NH$_2$;
with a, b, and c, d, q and s each being independently equal to 1, 2, 3, 4, or 5, e, f, and g, h, j, k, l, r, t, u, v, w, x, y, and z, aa, bb and cc each being independently equal to 0, 1, 2, 3, 4, or 5, and
i being equal to 1 or 2;
or a member selected from the group consisting of methyl, —CF$_3$, —CCl$_3$, —CBr$_3$, —CH$_2$—CN, —CH$_2$—O—CH$_3$, —CH$_2$—O—CF$_3$, —CH$_2$—SCF$_3$, —CH$_2$—NH$_2$, —CH$_2$—OH, —CH$_2$—SH, —CH$_2$—NH—CH$_3$, —CH$_2$—N(CH$_3$)$_2$, —CH$_2$—N(C$_2$H$_5$)$_2$, —CH$_2$—N(CH$_3$)(C$_2$H$_5$), ethyl, —CH$_2$—CH$_2$—NH$_2$, —CH$_2$—CH$_2$—OH, —CH$_2$—CH$_2$—SH, —CH$_2$—CH$_2$—NH—CH$_3$, —CH$_2$—CH$_2$—N(CH$_3$)$_2$, —CH$_2$—CH$_2$—N(C$_2$H$_5$)$_2$, —CH$_2$—CH$_2$—N(CH$_3$)(C$_2$H$_5$), —CH$_2$—CF$_3$, —C$_2$F$_5$, —CH$_2$—CCl$_3$, —CH$_2$—CBr$_3$, —CH$_2$—CH$_2$—CN, n-propyl, —CH$_2$—CH$_2$—CH$_2$—OH, —CH$_2$—CH$_2$—CH$_2$—SH, —CH$_2$—CH$_2$—CH$_2$—NH$_2$, —CH$_2$—CH$_2$—CH$_2$—NH—CH$_3$, —CH$_2$—CH$_2$—CH$_2$—N(CH$_3$)$_2$, —CH$_2$—CH$_2$—CH$_2$—N(C$_2$H$_5$)$_2$, —CH$_2$—CH$_2$—CH$_2$—N(CH$_3$)(C$_2$H$_5$), —CH$_2$—CH$_2$—O—CH$_3$, —CF$_2$—CF$_2$—CF$_3$, —CF(CF$_3$)$_2$, isopropyl, —CH$_2$—CH$_2$—CH$_2$—CN, —CH$_2$—O—CH$_2$—CH$_3$, —CH$_2$—CH$_2$—SCF$_2$, —CH$_2$—CH$_2$—OCF$_3$, —CH(CH$_3$)(O—CH$_3$), —CH(CH$_3$)(S—CH$_3$), n-butyl, —CF$_2$—CF$_2$—CF$_2$—CF$_3$, —CH$_2$—CH$_2$—CH$_2$—CH$_2$—CN, sec-butyl, isobutyl, tert-butyl, n-pentyl, sec-pentyl, neopentyl, n-hexyl, vinyl, 1-propenyl, 2-propenyl, 1-butenyl, 2-butenyl, 3-butenyl, 2-methylbuten-2-yl, (1,1,2)-trifluoro-1-butenyl, 1-pentenyl, 2-pentenyl, 3-pentenyl, and 4-pentenyl;
or an aryl group selected from the group consisting of phenyl and naphthyl, wherein the aryl group may be substituted by 1, 2, 3, 4, or 5 substituents independently selected from the group consisting of F, Cl, Br, I, —CN, —NO$_2$, —OH, —SH, methyl, ethyl, —CF$_3$, —O—CF$_3$, —S—CF$_3$, —SF$_5$, —O—CH$_3$, —O—C$_2$H$_5$, —NH$_2$, —N(CH$_3$)$_2$, —N(C$_2$H$_5$)$_2$, —N(H)(CH$_3$), and —N(H)(C$_2$H$_5$); and
R$^{10}$ represents —NR$^{23}$S(=O)$_2$R$^{24}$.

7. A compound according to claim 1, wherein
R$^8$, R$^9$, R$^{11}$, and R$^{12}$ each independently represent H; F; Cl; Br; I; —NO$_2$; —NH$_2$; —OH; —SH; —NR$^{13}$R$^{14}$; NH—R$^{15}$; —OR$^{16}$; —NR$^{23}$S(=O)$_2$R$^{24}$;
or a member selected from the group consisting of methyl, —CF$_3$, ethyl, —CH$_2$—CF$_3$, —C$_2$F$_5$, n-propyl, isopropyl, n-butyl, sec-butyl, isobutyl, tert-butyl, and n-pentyl, and
R$^{10}$ represent s —NR$^{23}$S(=O)$_2$R$^{24}$.

8. A compound according to claim 1, wherein
R$^{10}$ represents —NR$^{23}$S(=O)$_2$R$^{24}$ and
R$^8$, R$^9$, R$^{11}$, and R$^{12}$ in each case are hydrogen.

9. A compound according to claim 1, wherein
R$^{13}$, R$^{14}$, R$^{15}$, R$^{16}$, R$^{17}$, R$^{19}$, R$^{20}$, R$^{21}$, R$^{22}$, R$^{25}$, R$^{26}$, R$^{27}$, R$^{28}$, R$^{29}$, R$^{30}$, R$^{31}$, R$^{32}$, R$^{33}$, R$^{34}$, R$^{35}$, R$^{36}$, R$^{37}$, R$^{38}$, R$^{39}$, R$^{40}$, R$^{41}$, R$^{42}$, R$^{43}$, R$^{44}$, R$^{45}$, R$^{46}$, R$^{47}$ and R$^{48}$ independently represent a member selected from the group consisting of methyl, —CF$_3$, —CCl$_3$, —CBr$_3$, —CH$_2$—CN, —CH$_2$—O—CH$_3$, —CH$_2$—O—CF$_3$, —CH$_2$—SCF$_3$, —CH$_2$—NH$_2$, —CH$_2$—OH, —CH$_2$—SH, —CH$_2$—NH—CH$_3$, —CH$_2$—N(CH$_3$)$_2$, —CH$_2$—N(C$_2$H$_5$)$_2$, —CH$_2$—N(CH$_3$)(C$_2$H$_5$), ethyl, —CH$_2$—CH$_2$—NH$_2$, —CH$_2$—CH$_2$—OH, —CH$_2$—CH$_2$—SH, —CH$_2$—CH$_2$—NH—CH$_3$, —CH$_2$—CH$_2$—N(CH$_3$)$_2$, —CH$_2$—CH$_2$—N(C$_2$H$_5$)$_2$, —CH$_2$—CH$_2$—N(CH$_3$)(C$_2$H$_5$), —CH$_2$—CF$_3$, —C$_2$F$_5$, —CH$_2$—CCl$_3$, —CH$_2$—CBr$_3$, —CH$_2$—CH$_2$—CN, n-propyl, —CH$_2$—CH$_2$—CH$_2$—OH, —CH$_2$—CH$_2$—CH$_2$—SH, —CH$_2$—CH$_2$—CH$_2$—NH$_2$, —CH$_2$—CH$_2$—CH$_2$—NH—CH$_3$, —CH$_2$—CH$_2$—CH$_2$—N(CH$_3$)$_2$, —CH$_2$—CH$_2$—CH$_2$—N(C$_2$H$_5$)$_2$, —CH$_2$—CH$_2$—CH$_2$—N(CH$_3$)(C$_2$H$_5$), —CH$_2$—CH$_2$—O—CH$_s$, —CF$_2$—CF$_2$—CF$_3$, —CF(CF$_3$)$_2$, isopropyl, —CH$_2$—CH$_2$—CH$_2$—CN, —CH$_2$—O—CH$_2$—CH$_3$, —CH$_2$—CH$_2$—SCF$_3$, —CH$_2$—CH$_2$—OCF$_3$, —CH(CH$_3$)(O—CH$_3$), —CH(CH$_3$)(S—CH$_3$), n-butyl, —CF$_2$—CF$_2$—CF$_2$—CF$_3$, —CH$_2$—CH$_2$—CH$_2$—CH$_2$—CN, sec-butyl, isobutyl, tert-butyl, n-pentyl, sec-pentyl, neopentyl, n-hexyl, vinyl, 1-propenyl, 2-propenyl, 1-butenyl, 2-butenyl, 3-butenyl, 2-methylbuten-2-yl, (1,1,2)-trifluoro-1-butenyl, 1-pentenyl, 2-pentenyl, 3-pentenyl, and 4-pentenyl;
or a cycloaliphatic group selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl, and dithiolanyl, wherein the (hetero)cycloaliphatic group may, in each case, be substituted by 1, 2, 3, 4, or 5 substituents independently selected from the group consisting of thioxo (=S), F, Cl, Br, I, —CN, —CF$_3$, —SF$_5$, —OH, —NH$_2$, —O—CF$_3$, —SH, —O—CH$_3$, —O—C$_2$H$_5$, methyl, ethyl, n-propyl, isopropyl, n-butyl, sec-butyl, isobutyl, tert-butyl, —S—CH$_3$, —S—C$_2$H$_5$, —C(=O)—O—CH$_3$, —C(=O)—O—C$_2$H$_5$, Oxo (=O), —N(CH$_3$)$_2$, —N(C$_2$H$_5$)$_2$, —N(H)(CH$_3$), —N(H)(C$_2$H$_5$), —NO$_2$, —SCF$_3$, —C(=O)—OH, —O-phenyl, —O-benzyl, phenyl, and benzyl,
or a member selected from the group consisting of phenyl, naphthyl, (1,3)-benzodioxolyl, (1,4)-benzodioxanyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinoxalinyl, quinolinyl, and isoquinolinyl, wherein the member may, in each case, be substituted by 1, 2, 3, 4, or 5 substituents independently selected from the group consisting of F, Cl, Br, I, —CN, —NO$_2$, —OH, —SH, methyl, ethyl, n-propyl, isopropyl, n-butyl, sec-butyl, isobutyl, tert-butyl, —CF$_3$, —O—CF$_3$, —S—CF$_3$, —SF$_5$, —O—CH$_3$, —O—C$_2$H$_5$, —O-phenyl, —O-benzyl, —NH$_2$, —N(CH$_3$)$_2$, —N(C$_2$H$_5$)$_2$, —N(H)(CH$_3$) and —N(H)(C$_2$H$_5$).

10. A compound according to claim 1, wherein
R$^{18}$ represents a cycloaliphatic group, group, selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl, and dithiolanyl, wherein the cycloaliphatic group or heterocycloaliphatic group may, in each case, be substituted by 1, 2, 3, 4, or 5 substituents independently selected from the group consisting of thioxo (═S), F, Cl, Br, I, —CN, —CF$_3$, —SF$_5$, —OH, —NH$_2$, —O—CF$_3$, —SH, —O—CH$_2$, —O—C$_2$H$_5$, methyl, ethyl, n-propyl, isopropyl, n-butyl, sec-butyl, isobutyl, tert-butyl, —S—CH$_3$, —S—C$_2$H$_5$, —C(═O)—O—CH$_3$, —C(═O)—O—C$_2$H$_5$, Oxo (═O), —N(CH$_3$)$_2$, —N(C$_2$H$_5$)$_2$, —N(H)(CH$_3$), —N(H)(C$_2$H$_5$), —NO$_2$, —SCF$_3$, —C(═O)—OH, —O-phenyl, —O-benzyl, phenyl, and benzyl,
or a member selected from the group consisting of phenyl, naphthyl, (1,3)-benzodioxolyl, (1,4)-benzodioxanyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinoxalinyl, quinolinyl, and isoquinolinyl, wherein the member may, in each case, be substituted by 1, 2, 3, 4, or 5 substituents independently selected from the group consisting of F, Cl, Br, I, —CN, —NO$_2$, —OH, —SH, methyl, ethyl, n-propyl, isopropyl, n-butyl, sec-butyl, isobutyl, tert-butyl, —CF$_3$, —O—CF$_3$, —S—CF$_3$, —SF$_5$, —O—CH$_3$, —O—C$_2$H$_5$, —O-phenyl, —O-benzyl, —NH$_2$, —N(CH$_3$)$_2$, —N(C$_2$H$_5$)$_2$, —N(H)(CH$_3$) and —N(H)(C$_2$H$_5$), and —NH—C(═O)—O—CH$_3$.

11. A compound according to claim 1, wherein
R$^{23}$ is hydrogen or represents a member selected from the group consisting of methyl, ethyl, n-propyl, isopropyl, n-butyl, sec-butyl, isobutyl, tert-butyl, n-pentyl, sec-pentyl, neopentyl, and n-hexyl.

12. A compound according to claim 1, wherein
R$^{24}$ represents a member selected from the group consisting of methyl, —CH$_2$—CN, ethyl, —CH$_2$—CH$_2$—CN, n-propyl, isopropyl, n-butyl, sec-butyl, isobutyl, tert-butyl, n-pentyl, sec-pentyl, neopentyl, and n-hexyl.

13. A compound according to claim 1, wherein
p1 and p2 independently represent 0 or 1, the sum of p1 and p2 being 0 or 1.

14. A compound according to claim 1, wherein
X represents O, S or N—C≡N;
m is equal to 1;
n is equal to 1;
p1 and p2 each independently represent 0 or 1, with the sum of p1 and p2 being 0 or 1;
R$^1$, R$^2$, and R$^4$, R$^5$, R$^8$, R$^9$, R$^{11}$, and R$^{12}$ each independently stand for H; F; Cl; I; Br; —NO$_2$; —NH$_2$; —OH; —SH; —NR$^{13}$R$^{14}$; —NH—R$^{15}$; —OR$^{16}$; —SR$^{17}$; —NR$^{23}$S(═O)$_2$R$^{24}$; or for a member selected from the group consisting of methyl, —CF$_3$, ethyl, —CH$_2$—CF$_3$, —C$_2$F$_5$, n-propyl, isopropyl, n-butyl, sec-butyl, isobutyl, tert-butyl, or n-pentyl;
R$^3$ represents F; Cl; Br; I; —O R$^{16}$; —NR$^{23}$S(═O)$_2$R$^{24}$;
or a member selected from the group consisting of —SF$_5$, —CF$_3$, —C$_2$F$_5$, —CH$_2$—CF$_3$, —CF(CF$_3$)$_2$, isopropyl, —CH(CH$_3$)O—CH$_s$), —CH(CH$_3$)(S—CH$_3$), sec-butyl, isobutyl, and tert-butyl;
R$^6$ and R$^7$ are each hydrogen, or
R$^6$ and R$^7$, together with the interconnecting C—C bridge, form an unsubstituted phenylene group;
R$^{10}$ stands for —NR$^{23}$S(═O)$_2$R$^{24}$;
R$^{13}$, R$^{14}$, R$^{15}$, R$^1$b, and R$^{17}$, each independently represent a member selected from the group consisting of —CF$_3$, —C$_2$F$_5$, —CH$_2$—CF$_3$, methyl, ethyl, n-propyl, isopropyl, n-butyl, sec-butyl, isobutyl, tert-butyl, n-pentyl, sec-pentyl, neopentyl, and n-hexyl;
or a member selected from the group consisting of phenyl, thiophenyl, furanyl, and pyridinyl, wherein the member may, in each case, be substituted by 1, 2, 3, 4, or 5 substituents independently selected from the group consisting of F, Cl, Br, I, —CN, —NO$_2$, —OH, —SH, methyl, ethyl, n-propyl, isopropyl, n-butyl, sec-butyl, isobutyl, tert-butyl, —CF$_3$, —O—CF$_3$, —S—CF$_3$, —SF$_5$, —O—CH$_3$ and —O—C$_2$H$_5$;
R$^{23}$ is hydrogen, and
R$^{24}$ represents a member selected from the group consisting of methyl, —CH$_2$—CN, ethyl, —CH$_2$—CH$_2$—CN, n-propyl, isopropyl, n-butyl, sec-butyl, isobutyl, tert-butyl, n-pentyl, sec-pentyl, neopentyl, and n-hexyl;
or a physiologically acceptable salt thereof.

15. A compound according to claim 1, wherein
X stands for O, S or N—C≡N;
m is equal to 1;
n is equal to 1;
p1 and p2 each independently represent 0 or 1, the sum of p1 and p2 being 0 or 1;
R$^1$, R$^2$, and R$^4$, R$^5$, R$^8$, R$^9$, R$^{11}$, and R$^{12}$ are each independently hydrogen;
R$^3$ represents —OR$^{16}$; —NR$^{23}$S(═O)$_2$R$^{24}$;
or a member selected from the group consisting of —CF$_3$, isopropyl, sec-butyl, isobutyl, and tert-butyl;
R$^6$ and R$^7$ are each hydrogen, or
R$^6$ and R$^7$, together with the interconnecting C—C bridge, form an unsubstituted phenylene group;
R$^{10}$ represents —NR$^{23}$S(═O)$_2$R$^{24}$;
R$^{10}$ represents a member selected from the group consisting of —CF$_3$, —C$_2$F$_5$, and —CH$_2$—CF$_3$;
R$^{23}$ is hydrogen, and
R$^{24}$ represents a member selected from the group consisting of methyl, ethyl, n-propyl, isopropyl, n-butyl, sec-butyl, isobutyl, tert-butyl, n-pentyl, sec-pentyl, neopentyl, and n-hexyl;
or a physiologically acceptable salt thereof.

16. A compound according to claim 1, wherein said compound is selected from the group consisting of:
[1] N-[4-[3-(4-tert-butylbenzyl)-2-thioxo-imidazolidinylmethyl]phenyl]methanesulfonamide,
[2] N—[4-[3-(4-tert-butylbenzyl)-2-thioxo-2,3-dihydrobenzoimidazol-1-ylmethyl]phenyl]methanesulfonamide,
[3] N-[4-[3-(4-tert-butylbenzyl)-2-thioxotetrahydropyrimidin-1-ylmethyl]phenyl]methanesulfonamide,
[4] N-[4-[3-(4-tert-butylbenzyl)-2-oxo-imidazolidin-1-ylmethyl]phenyl]methanesulfonamide,

[5] N-[4-[3-(4-tert-butylbenzyl)-2-oxotetrahydropyrimidin-1-ylmethyl]phenyl]methanesulfonamide,
[6] N-[4-[3-(4-tert-butylbenzyl)-2-oxo-2,3-dihydrobenzoimidazol-1-ylmethyl]phenyl]methanesulfonamide,
[7] N-[4-[3-(4-trifluoromethoxybenzyl)-2-oxo-2,3-dihydrobenzimidazol-1-yl-methyl]phenyl]methanesulfonamide,
[8] N-[4-[3-(4-trifluoromethoxybenzyl)-2-thioxo-2,3-dihydrobenzimidazol-1-yl-methyl]phenyl]methanesulfonamide,
[9] N-[4-[3-(4-methanesulfonylaminobenzyl)-2-oxo-2,3-dihydrobenzimidazol-1-ylmethyl]phenyl]methanesulfonamide, and
[10] N-{4-[2-oxo3-(4-trifluoromethylbenzyl)-2,3-dihydrobenzimidazol-1-yl-methyl]phenyl}methanesulfonamide,
or a physiologically acceptable salt thereof.

17. A process for preparing a cyclic urea compound according to claim 1, comprising the steps of:
reacting at least one compound corresponding to formula II,

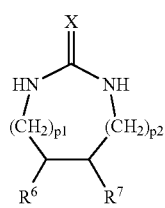

II in a reaction medium, optionally in the presence of at least one base and optionally in the presence of at least one alkali metal iodide, with at least one compound corresponding to formula III,

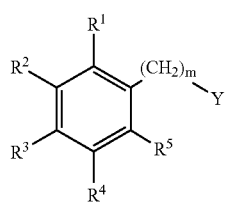

III wherein Y represents a leaving group, to produce at least one compound corresponding to formula IV,

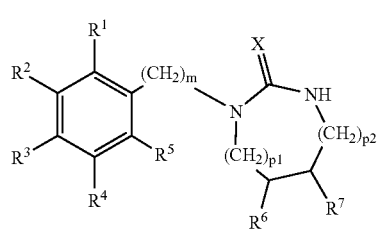

IV and optionally purifying and/or isolating this compound,
or
reacting at least one compound corresponding to formula V,

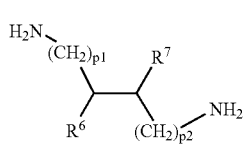

V in a reaction medium, optionally in the presence of at least one base, with at least one compound corresponding to formula III to form at least one compound of the general formula VI,

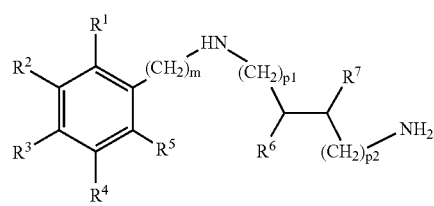

VI and optionally purifying and/or isolating this compound, and
reacting at least one compound corresponding to formula VI, in a reaction medium, optionally in the presence of at least one base, with at least one compound corresponding to the formula Z—C(=X)—Z wherein X stands for an oxygen atom or sulfur atom and Z in each case for a leaving group, to form at least one compound corresponding to formula IV and optionally purifying and/or isolating this compound,
or
reacting at least one compound corresponding to formula VII,

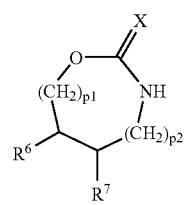

VII in a reaction medium, with at least one compound corresponding to formula VIII,

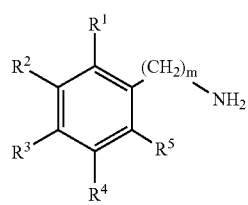

VIII to produce at least one compound corresponding to formula IV, and optionally purifying and/or isolating this compound, and reacting at least one compound corresponding to formula IV, in a reaction medium, in the presence of at least one base, and optionally at least one alkali metal iodide, with at least one compound corresponding to formula IX,

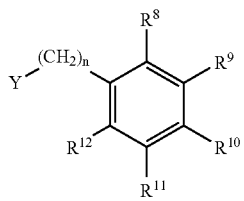

IX provided that at least one of the substituents $R^8$ to $R^{12}$ stands for an —N(PG)$_2$ group, wherein PG is a protective group, or two PG groups, together with the interconnecting nitrogen atom, form a cyclic protective group, and Y is a leaving group, to produce at least one compound corresponding to formula XI,

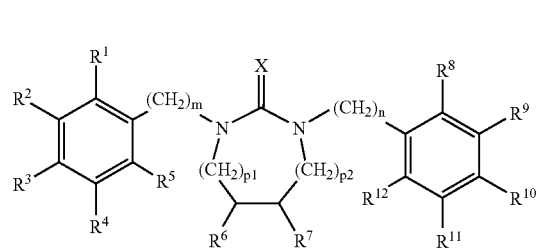

XI and optionally purifying and/or isolating this compound, and converting at least one compound corresponding to formula XI, in a reaction medium, in the presence of at least one base, or in the presence of at least one acid, or in the presence of an alkali metal boron hydride, to form at least one compound corresponding to formula XII,

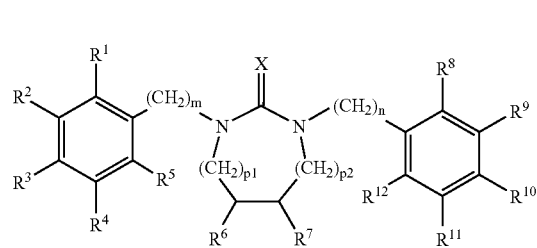

XII provided that at least one of the $R^8$ to $R^{12}$ stands for —NH$_2$, and optionally purifying and/or isolating this compound, or reacting at least one compound corresponding to formula IV in a reaction medium, in the presence of at least one base, optionally in the presence of least one alkali metal iodide, with at least one compound corresponding to formula XIII,

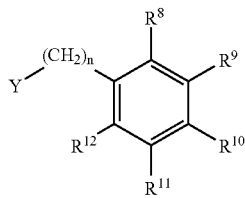

XIII provided that at least one $R^8$ to $R^{12}$ is —NO$_2$, and Y is a leaving group, to form at least one compound corresponding to formula XIV,

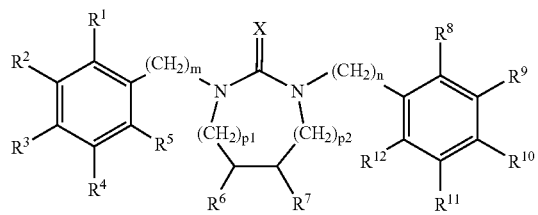

XIV provided that at least one of $R^8$ to $R^{12}$ is —NO$_2$, and optionally purifying and/or isolating this compound, and converting at least one compound corresponding to formula XIV in a reaction medium, in the presence of hydrogen and in the presence of a catalyst, to produce at least one compound corresponding to formula XII, provided that at least one of $R^8$ to $R^{12}$ is —NH$_2$, and optionally purifying and/or isolating this compound, and reacting at least one compound corresponding to formula XII in a reaction medium, optionally in the presence of at least one base, with at least one compound corresponding to formula $R^{24}$—S(=O)$_2$—Z, wherein Z is a leaving group, to form at least one compound corresponding to formula Ia,

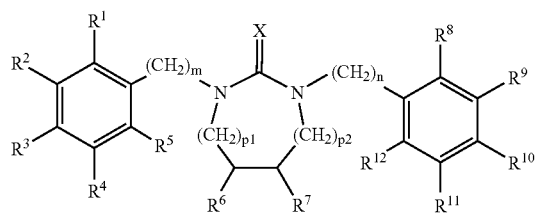

Ia provided that at least one of $R^8$ to $R^{12}$ is an —NH—S(=O)$_2$—$R^{24}$ group, and optionally purifying and/or isolating this compound, or reacting at least one compound corresponding to formula IV, in a reaction medium, in the presence of at least one base, or in the presence of at least one alkali metal carbonate salt, and optionally at least one alkali metal iodide, with at least one compound corresponding to formula XV,

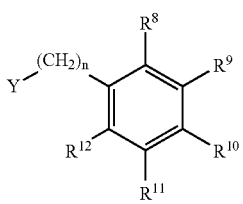

XV provided that at least one of $R^8$ to $R^{12}$ is an —NH—S(=O)$_2$—$R^{24}$ group, to produce at least one compound corresponding to formula Ia, and optionally purifying and/or isolating this compound, and optionally reacting at least one compound corresponding to formula Ia in a reaction medium, optionally in the presence of at least one base, with at least one compound corresponding to formula $R^{23}$—Z, wherein $R^{23}$ is not hydrogen, and Z is a chlorine atom, halogen atom or other leaving group, to produce at least one compound corresponding to formula Ib,

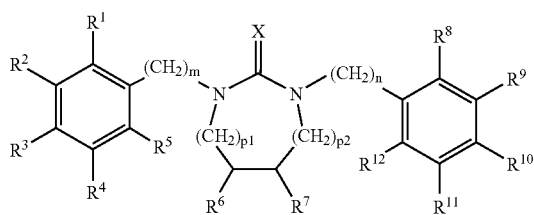

Ib provided that at least one of $R^8$ to $R^{12}$ represents an —$NR^{23}$—S(=O)$_2$—$R^{24}$ group, and optionally purifying and/or isolating this compound, and optionally reacting at least one compound corresponding to formula Ib, wherein X is an oxygen atom, and at least one of the substituents $R^8$ to $R^{12}$ is an —$NR^{23}$—S(=O)$_2$—$R^{24}$ group, in a reaction medium, with at least one compound corresponding to formula XVI

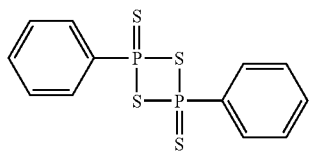

XVI wherein the phenyl groups are each para-substituted by 1 or 2 substituents independently selected from the group consisting of methoxy, phenoxy, Cl, methyl, and Br, or with phosphorus pentasulfide, to produce at least one compound corresponding to formula Ib wherein X is a sulfur atom, provided that at least one of $R^8$ to $R^{12}$ is an —$NR^{23}$—S(=O)$_2$—$R^{24}$ group, and optionally purifying and/or isolating this compound.

18. The process of claim 17, wherein said step of reacting at least one compound corresponding to formula II with at least one compound corresponding to formula III is performed in the presence of at least one metal hydride salt, or in the presence of potassium and/or sodium hydride, or in the presence of at least one alkali metal carbonate salt, or in the presence of potassium carbonate and/or sodium carbonate, and optionally in the presence of potassium iodide and/or sodium iodide, or Y represents a halogen which may be a bromium atom or chlorine atom, or said step of reacting at least one compound corresponding to formula V with least one compound corresponding to formula III is performed in the presence of at least one base selected from the group consisting of pyridine, triethylamine, and diisopropylethylamine, or said step of reacting at least one compound corresponding to formula VI with at least one compound corresponding to the formula Z—C(=X)—Z, is performed in the presence of at least one base selected from the group consisting of pyridine, triethylamine, and diisopropylethylamine, and Z is a chlorine atom or other halogen, or said step of reacting at least one compound corresponding to formula IV with least one compound corresponding to formula IX is performed in the presence of at least one metal hydride salt, or in the presence of potassium hydride and/or sodium hydride, or in the presence of at least one alkali metal carbonate salt, and optionally in the presence of potassium carbonate and/or sodium carbonate or PG is a tert-butoxycarbonyl group or benzyloxycarbonyl group, or the cyclic protective group is a phthalimide group or Y is chlorine or bromine or another halogen atom, or said step of converting at least one compound corresponding to formula XI is performed in the presence of dimethylamine or hydrazine and/or phenylhydrazine or sodium tetrahydridoborate, or said step of reacting at least one compound corresponding to formula IV with at least one compound corresponding to formula XIII is performed in the presence of at least one metal hydride salt, or potassium hydride and/or sodium hydride, or in the presence of at least one alkali metal carbonate salt, or potassium carbonate and/or sodium carbonate, and optionally in the presence of potassium iodide and/or sodium iodide, or Y is chlorine or bromine or another halogen atom, or said step of reacting at least one compound corresponding to formula XII with at least one compound corresponding to formula $R^{24}$—S(=O)$_2$—Z, is performed in the presence of at least one base selected from the group consisting of pyridine, triethylamine, and diisopropylethylamine, and wherein Z is chlorine or another halogen atom, or said step of reacting at least one compound corresponding to formula IV with at least one compound corresponding to formula XV is performed in the presence of at least one metal hydride salt, or potassium hydride and/or sodium hydride, or in the presence of potassium carbonate and/or sodium carbonate, or optionally potassium iodide and/or sodium iodide, or in said step of reacting at least one compound corresponding to formula Ib with at least one compound corresponding to formula XVI, the phenyl groups are substituted by a phenoxy group or methoxy group.

19. A process for preparing a cyclic urea compound according to claim 1, comprising the steps of:

reacting at least one compound corresponding to formula II,

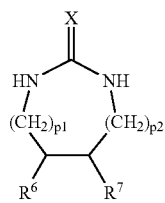

II in a reaction medium, in the presence of at least one base, or in the presence of at least one alkali metal carbonate salt, or optionally at least one alkali metal iodide, with at least one compound corresponding to formula XVII,

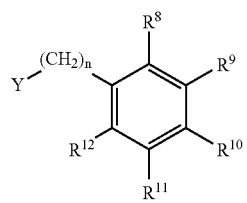

XVII provided that at least one of $R^8$ to $R^{12}$ is an —$N(PG)_2$ group, wherein PG in each case is a protective group, or two PG groups, together with the interconnecting nitrogen atom, form a phthalimide group, or at least one of $R^8$ to $R^{12}$ is an —$NO_2$ group, and Y is a leaving group, to produce at least one compound corresponding to formula XVIII,

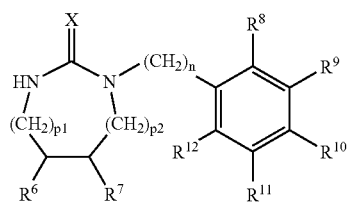

XVIII provided that at least one of $R^8$ to $R^{12}$ is an —$N(PG)_2$ group or an —$NO_2$ group, and optionally purifying and/or isolating this compound, or reacting at least one compound corresponding to formula XIX,

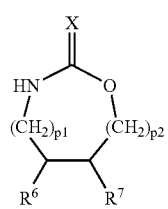

XIX in a reaction medium, with at least one compound corresponding to formula XX,

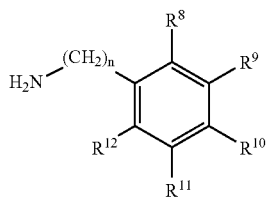

XX provided that at least one of $R^8$ to $R^{12}$ is an —$N(PG)_2$ group, wherein PG in each case is a protective group, or two PG groups, together with the interconnecting nitrogen atom, form a cyclic protective group, or two PG groups, together with the interconnecting nitrogen atom, form a phthalimide group or at least one of $R^8$ to $R^{12}$ is an —$NO_2$ group, to produce at least one compound corresponding to formula XVIII, and optionally purifying and/or isolating this compound, or reacting at least one compound corresponding to formula V,

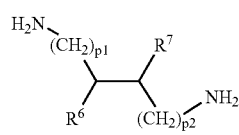

V in a reaction medium, optionally in the presence of at least one base, with at least one compound corresponding to formula XVII to produce at least one compound of the general formula XXI,

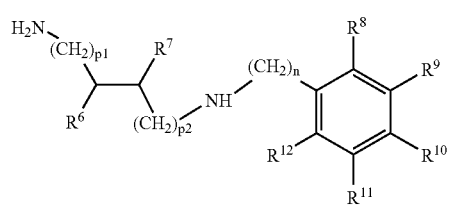

XXI provided that at least one of $R^8$ to $R^{12}$ is an —$N(PG)_2$ group or an —$NO_2$ group, and optionally purifying and/or isolating this compound, and reacting at least one compound corresponding to formula XXI, in a reaction medium, optionally in the presence of at least one base, with at least one compound corresponding to formula Z—C(=X)—Z, wherein X is an oxygen atom or sulfur atom and Z is a chlorine, halogen or other leaving group, to produce at least one compound corresponding to formula XVIII, and optionally purifying and/or isolating this compound, and reacting at least one compound corresponding to formula XVIII, in a reaction medium, in the presence of at least one base, or in the presence of at least one alkali metal carbonate salt, or optionally at least one alkali metal iodide, with at least one compound corresponding to formula III,

III

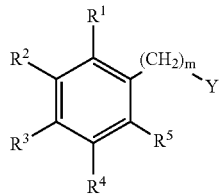

wherein Y is chlorine or bromine or halogen or a leaving group, to produce at least one compound corresponding to formula XXII,

XXII

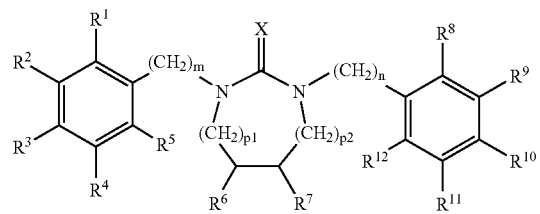

provided that at least one of $R^8$ to $R^{12}$ is an —N(PG)$_2$ group or —NO$_2$ group, and optionally purifying and/or isolating this compound, and reacting at least one compound corresponding to formula XXII, in a reaction medium, in the presence of at least one base, or in the presence of at least one acid, or in the presence of hydrazine and/or phenylhydrazine or in the presence of at least one alkali metal boron hydride, or in the presence of hydrogen and a catalyst, to produce at least one compound of the general formula XII,

XII

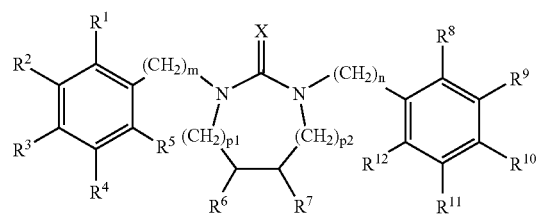

provided that at least one of $R^8$ to $R^{12}$ is an —NH$_2$ group, and optionally purifying and/or isolating this compound, and reacting at least one compound corresponding to formula XII, in a reaction medium, optionally in the presence of at least one base, with at least one compound corresponding to formula $R^{24}$—S($=$O)$_2$—Z, wherein Z is chlorine, halogen or a leaving group, to produce at least one compound corresponding to formula Ia, Ia

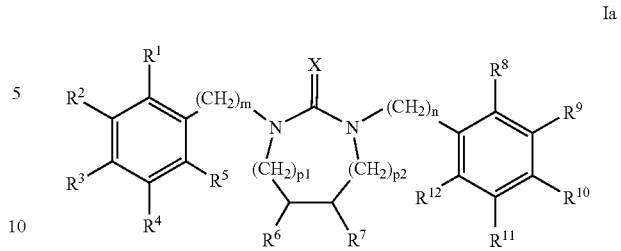

provided that at least one of $R^8$ to $R^{12}$ is an —NH—S($=$O)$_2$—$R^{24}$ group, and optionally purifying and/or isolating this compound, and optionally reacting at least one compound corresponding to formula Ia, in a reaction medium, optionally in the presence of at least one base, with at least one compound corresponding to formula $R^{23}$—Z wherein $R^{23}$ is not hydrogen and Z is chlorine, halogen or a leaving group, to produce at least one compound corresponding to formula Ib, Ib

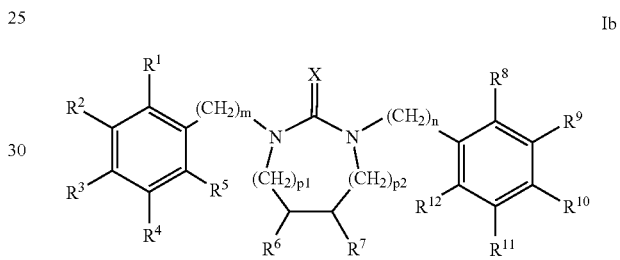

provided that at least one of $R^8$ to $R^{12}$ is an —NR$^{23}$—S($=$O)$_2$—$R^{24}$ group, and optionally purifying and/or isolating this compound, and optionally reacting at least one compound corresponding to formula Ib wherein X is oxygen, provided that at least one of the substituents $R^8$ to $R^{12}$ is an —NR$^{23}$—S($=$O)$_2$—$R^{24}$ group, in a reaction medium, with at least one compound corresponding to formula XVI,

XVI

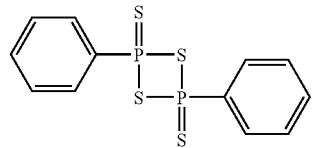

wherein the phenyl groups are each para-substituted by 1 or 2 substituents independently selected from the group consisting of methoxy, phenoxy, Cl, methyl, and Br, or with phosphorus pentasulfide, to produce at least one compound corresponding to formula Ib wherein X is a sulfur atom, provided that at least one of $R^8$ to $R^{12}$ is an —NR$^{23}$—S($=$O)$_2$—$R^{24}$ group, and optionally purifying and/or isolating this compound.

20. The process of claim 19, wherein
said step of reacting at least one compound corresponding to formula II, with at least one compound corresponding to formula XVII is performed in the presence of at least one metal hydride salt, or potassium hydride and/or sodium hydride, or in the presence of potassium carbonate and/or sodium carbonate or optionally potassium iodide and/or sodium iodide or Y is chlorine or bromine or another halogen, or in said step of reacting at least one compound corresponding to formula XIX with at least one compound corresponding to formula XX at least one of $R^8$ to $R^{12}$ is an —N(PG)$_2$ group, or said step of reacting at least one compound corresponding to formula XVIII with at least one compound corresponding to formula III is performed in the presence of at least one metal hydride salt, or in the presence of potassium hydride and/or sodium hydride, or in the presence of potassium carbonate and/or sodium carbonate, or optionally potassium iodide and/or sodium iodide, or said step of reacting at least one compound corresponding to formula XXII with at least one compound corresponding to formula XII is performed in the presence of sodium tetrahydridoborate, or in said step of reacting at least one compound corresponding to formula Ib with at least one compound corresponding to formula XVI, the phenyl groups of the compound corresponding to formula XVI are substituted by a phenoxy group or methoxy group.

21. A process for preparing a cyclic urea compound according to claim 1, comprising the steps of:

reacting at least one compound corresponding to formula II,

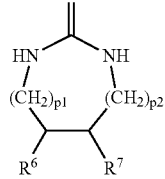

II in a reaction medium, in the presence of at least one base, or in the presence of at least one alkali metal carbonate salt, with at least one compound corresponding to formula XXIII

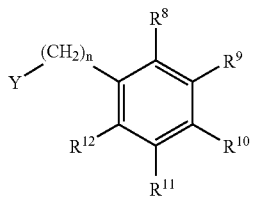

XXIII provided that at least one $R^8$ to $R^{12}$ is an —NR$^{23}$—S(=O)$_2$—R$^{24}$ group and Y is chlorine or bromine or halogen or a leaving group, to produce at least one compound corresponding to formula XXIV,

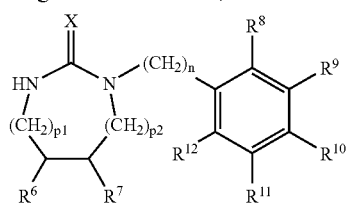

XXIV provided that at least one of $R^8$ to $R^{12}$ is an —NR$^{23}$—S(=O)$_2$—R$^{24}$ group, and optionally purifying and/or isolating this compound, and reacting at least one compound corresponding to formula XXIV, in a reaction medium, in the presence of at least one base, or in the presence of at least one alkali metal carbonate salt, and optionally at least one alkali metal iodide, or optionally potassium iodide and/or sodium iodide, with at least one compound corresponding to formula III,

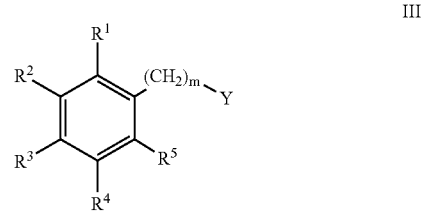

III wherein Y is chlorine or bromine or halogen or a leaving group, to produce at least one compound corresponding to formula Ib,

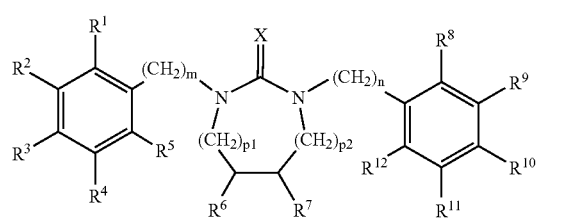

Ib provided that at least one of $R^8$ to $R^{12}$ is an —NR$^{23}$—S(=O)$_2$—R$^{24}$ group, and optionally purifying and/or isolating this compound, and optionally reacting at least one compound corresponding to formula Ib wherein X is an oxygen atom, provided that at least one of $R^8$ to $R^{12}$ is an —NR$^{23}$—S(=O)$_2$—R$^{24}$ group, in a reaction medium, with at least one compound corresponding to formula XVI,

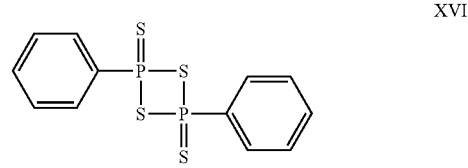

XVI wherein the phenyl groups are each para-substituted by 1 or 2 substituents independently selected from the group consisting of methoxy, phenoxy, Cl, methyl, and Br, or with phosphorus pentasulfide, to produce at least one compound corresponding to formula Ib wherein X is a sulfur atom, provided that at least one of $R^8$ to $R^{12}$ is an —NR$^{23}$—S(=O)$_2$—R$^{24}$ group, and optionally purifying and/or isolating this compound.

22. The process of claim 21, wherein said step of reacting least one compound corresponding to formula II with at least one compound corresponding to formula XXIII is performed in the presence of at least one metal hydride salt, or in the presence of potassium hydride and/or sodium hydride, or in the presence of potassium carbonate and/or sodium carbonate, or the step of reacting reacting at least one compound corresponding to formula XXIV with at least one compound corresponding to formula III is performed in the presence of at least one metal hydride salt, or in the presence of potassium hydride and/or sodium hydride, or in the presence of potassium carbonate and/or sodium carbonate, or in said step of reacting at least one compound corresponding to formula Ib with at least one compound corresponding to formula XVI, the phenyl groups of the compound corresponding to formula XVI are substituted by a phenoxy group or methoxy group.

23. A pharmaceutical formulation comprising a compound according claim 1 and at least physiologically acceptable adjuvent.

24. A method of treating pain, said method comprising administering to a patient a pharmaceutically effective amount of a compound according to claim 1.

25. The method of claim 24 wherein said pain is selected from the group consisting of acute pain, chronic pain, neuropathic pain, and visceral pain.

* * * * *